(12) United States Patent
Krawczyk

(10) Patent No.: US 7,579,332 B2
(45) Date of Patent: Aug. 25, 2009

(54) NUCLEOBASE PHOSPHONATE ANALOGS FOR ANTIVIRAL TREATMENT

(75) Inventor: Steven H. Krawczyk, Palo Alto, CA (US)

(73) Assignee: Gilead Sciences, Inc., Palo Alto, CA (US)

( * ) Notice: Subject to any disclaimer, the term of this patent is extended or adjusted under 35 U.S.C. 154(b) by 197 days.

(21) Appl. No.: 10/903,288

(22) Filed: Jul. 30, 2004

(65) Prior Publication Data

US 2005/0059637 A1    Mar. 17, 2005

Related U.S. Application Data

(60) Provisional application No. 60/491,123, filed on Jul. 30, 2003.

(51) Int. Cl.
   *C07F 9/6561*    (2006.01)
   *C07F 9/6512*    (2006.01)
   *A61K 31/675*    (2006.01)
   *A61P 31/18*     (2006.01)

(52) U.S. Cl. .......................... 514/81; 544/244; 544/243

(58) Field of Classification Search ................ 514/81; 544/244

See application file for complete search history.

(56) References Cited

U.S. PATENT DOCUMENTS

| | | | |
|---|---|---|---|
| 4,808,716 A * | 2/1989 | Holy et al. ................. | 544/244 |
| 4,968,788 A | 11/1990 | Farquhar | |
| 5,013,829 A * | 5/1991 | Nair et al. ................. | 514/46 |
| 5,650,510 A * | 7/1997 | Webb et al. ............... | 544/244 |
| 5,663,159 A | 9/1997 | Starrett, Jr. et al. | |
| 5,817,647 A * | 10/1998 | Casara et al. ............. | 514/81 |
| 5,854,228 A | 12/1998 | Martin et al. | |
| 5,922,696 A | 7/1999 | Casara et al. | |
| 6,018,049 A | 1/2000 | Hajima et al. | |
| 6,127,121 A | 10/2000 | Meyer, Jr. et al. | |
| 6,143,877 A | 11/2000 | Meyer et al. | |
| 2002/0103378 A1 | 8/2002 | Ellis | |
| 2003/0004345 A1 | 1/2003 | Casara et al. | |
| 2004/0014722 A1* | 1/2004 | Babu et al. ............... | 514/81 |

FOREIGN PATENT DOCUMENTS

| | | |
|---|---|---|
| EP | 0 269 947 A1 | 6/1988 |
| EP | 0 532 423 | 3/1993 |
| EP | 0 618 214 A1 | 10/1994 |
| EP | 0 701 562 B1 | 6/1997 |
| JP | 07048374 A * | 2/1995 |
| WO | WO 91/19721 | 12/1991 |
| WO | WO 94/21604 | 9/1994 |
| WO | WO 94/22882 | 10/1994 |
| WO | WO 95/07920 | 3/1995 |
| WO | WO 96/15111 | 5/1996 |
| WO | WO 01/38584 | 5/2001 |
| WO | WO 03/087298 | 10/2003 |
| WO | WO 2005054269 A1 * | 6/2005 |

OTHER PUBLICATIONS

Kim, et al., J. Med. Chem.; 1990; 33(4) pp. 1207-1213.*
Carara et al, Bioorganic & Medicinal Chemistry Letters vol. 5, Issue 12, Jun. 22, 1995, pp. 1275-1280.*
Zhang et al., European Journal of Inorganic Chemistry vol. 2003, Issue 13, Date: Jul. 2003, pp. 2426-2437 (Published Online: Jun. 24, 2003).*
Julian-Ortiz et. at., J. Med. Chem. 1999, vol. 42, pp. 3308.*
Olgilvie, Can. J. Chem. vol. 62, 1984, pp. 241-252.*
Rosenberg, Collection of Czechoslovak Chemical Communications (1988), 53(11B), 2753-77.*
Translation of JP 07048374A (1995).*
Alexander et al. "Investigation of (Oxodioxolenyl)methyl Carbamates as Nonchiral Bioreversible Prodrug Moieties for Chiral Amines." 39:480-486; J Med Chem, 1996.
Anan'eva et al. "(2-Iodoethyl)Phosphonic Derivatives." 53(4):480-483; J. Gen. Chem. USSR, 1983.
Anderson et al. "2-Chloro-4(R),5(R)-dimethyl-2-oxo-1,3,2-dioxaphospholane, a New Chiral Derivatizing Agent." 49:1304-1305; J Org Chem, 1984.
Asante-Appiah et al. "HIV-1 Integrase: Structural Organization, Conformational Changes, and Catalysis." 52:351-363; Advances in Virus Research, 1999.
Bai et al. "Structural Specificity of Mucosal-Cell Transport and Metabolism of Peptide Drugs: Implication for Oral Peptide Drug Delivery." 9:969-978: Pharm Res, 1992.
Barre-Sinoussi, Francoise "HIV as the cause of AIDS." 348:31-35; Lancet, 1996.

(Continued)

Primary Examiner—Mark L Berch
(74) Attorney, Agent, or Firm—Allan N. Kutzenco; Gilead Sciences, Inc.

(57) ABSTRACT

The invention provides compounds with activity against infectious diseases. The compounds of the invention may inhibit retroviral reverse transcriptases and thus inhibit the replication, of the virus. The compounds of the invention may be useful for treating human patients infected with a human retrovirus, such as human immunodeficiency virus (strains of HIV-1 or HIV-2) or human T-cell leukemia virus (HTLV-1 or HTLV-II) which results in acquired immunodeficiency syndrome (AIDS) and/or related diseases. Representative of the invention is a compound of the following formula, with the substituents defined herein:

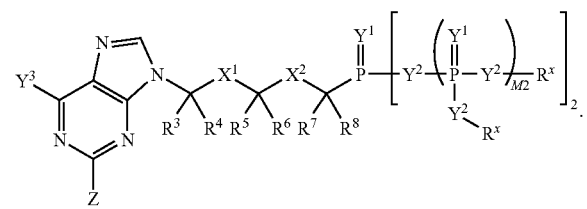

9 Claims, No Drawings

Balsiger et al. "Synthesis of Potential Anticancer Agents. XVIII. Analogs of Carbamoyl Phosphate." 24:434-436 ; J Org Chem, 1959.

Balthazor et al. "Nickel-Catalyzed Arbuzov Reaction: Mechanistic Observations." 45:5425-5426; J Org Chem, 1980.

Benzaria et al. "Synthesis, In Vitro Antiviral Evaluation, and Stability Studies of Bis(S-acyl-2-thioethyl) Ester Derviatives of . . . " 39:4958-4965; J Med Chem, 1996.

Beusen et al. "Solid-State Nuclear Magnetic Resonance Anlysis of the Conformation of an Inhibitor Bound to Thermolysin." 38:2742-2747; J Med Chem, 1995.

Bhuta et al. "Analogs of Chloramphenicol: Circular Dichroism Spectra, Inhibition of Ribosomal Peptidyltransferase, and Possible Mechanis." 23(12):1299-1305;J Med Chem, 1980.

Bundgaard et al. "Design and Application of Prodrugs." pp. 113-191; Textbook of Drug Design and Development, 1991.

Burger et al. "Monoesters and Ester-amidates of Aromatic Phosphonic Acids." 79:3575-3579; J Am Chem Soc, 1957.

Campagne et al. "(1H-Benzotriazol-1-yloxy)tris(dimethylamino)phosphonium Hexafluorophosphate-and . . . " 60(16):5214-5223; J Org Chem, 1995.

Campagne et al. "Synthesis of Mixed Phosphonate Diester Analogues of Dipeptides Using BOP or P yBOP Reagents." 34:6743-6744; Tet Lett, 1993.

Campbell et al. "The Synthesis of Phosphonate Esters, an Extension of the Mitsunobu Reaction." 57:6331-6335; J Org Chem, 1992.

Casara et al. "Synthesis of Acid Stable 5'-O-Fluoromethyl Phosphonates of Nucleosides, Evaluation as Inhibitors of Reverse Transcriptase" 2:145-148; Bioorg Med Chem Lett, 1992.

Casteel et al. "Steric and Electronics Effects in the Aryl Phosphate to Arylphosphonate Rearrangement" 691-693; Synthesis , 1991.

Chen et al. "Design, Synthesis, and Biochemical Evaluation of Phosphonate and Phosphonamidate Analogs of Glutathionylspermidine . . . " 40(23):3842-3850; J Med Chem, 1997.

Clayton et al. "BRL.8988 (Talampicillin), a Well-Absorbed Oral Form of Ampicillin." 5(6):670-671; Antimicro Ag & Chemo, 1974.

Coe et al. "Synthesis of Some Mimics of Nucleoside Triphophates." pp. 312-314; J. Chem. Soc. Chem. Commun., 1991.

Corey et al. "Selective Cleavage of Allyl Ethers Under Mild Conditions By Transition Metal Reagants." 38(18):3224;J Org Chem., 1973.

Davies et al. "Dinucleotide Analogues as Inhibitors of Thymidine Kinase, Thyidylate Kinase, and Ribonucleotide Reductase." 31(7) 1305-1308; J Med Chem, 1988.

De Clercq, Erick. "New Developments in the Chemotherapy of Lentivirus (Human Immunodeficiency Virus) Infections.." 724:438-456; Annals of the NY Acad of Sciences, 1994.

De Lombaert et al. "N-Phosphonomethyl Dipeptides and heir Phosphonate Prodrugs, a New Generation of Neutral Endopeptidase . . . " 37:498-511; J Med Chem., 1994.

Efimov et al. "Synthesis of DNA Analogues with Novel Carboxamidomethyl Phosphonamide and Glycinamide Internucleoside Linkages." 8:1013-1018; Bioorg Med Chem Lett., 1998.

Eliel et al. pp. 322-381; Stereochem Org Comp, 1994.

Esposito et al. "HIV Integrase Structures and Function." 52:319-333; Advances in Virus Research, 1999.

Farquhar et al. "Biologically Reversible Phosphate-Protective Groups." 72(3):324-325; J Pharm Sci., 1983.

Fasman et al., "Alkyl Bases, Nucleosides, and Nucleotides, UV Spectral Characteristic . . . " pp. 385-394; Practical Handbook of Biochem and Molec Biol, 1989.

Frankel et al. "HIV-1 Fifteen Proteins and an RNA." 67:1-25; Ann Rev Biochem, 1998.

Freeman et al. "3 Prodrug Design for Phosphantes and Phosphonates." 34:112-147; Progress in Medicinal Chemistry, 1997.

Galeotti et al. "A Straightforward Synthesis of -Amino Phosphonate Monoesters Using BroP or TPyClU." 37(23):3997-3998; Tet Lett., 1996.

Griffin et al. "D-Glucopyranose 5-Deoxy-6-phosphonic Acid." 78(10):2336-2338; J Am Chem Soc., 1956.

Hakimelahi et al., "Design, Synthesis, and Structure—Activity Relationship of Novel Dinucleotide Analogs As Agents Against Herpes . . . " 38:4648-4659; J Med Chem., 1995.

Hottiger et al., "Human Immunodeficiency Virus Type 1 Reverse Transcriptase." 377:97-120; Biol Chem., 1996.

Jacob III, Peyton "Resolution of ( )-5-Bromonomicotine. Synthesis of (R)- and (S)- Nornicotine of High Enantiomeric Purity." 47:4165-4167; J Org Chem,, 1982.

Katz et al. "The Retroviral Enzymes." 63:133-173; Ann Rev Biochem, 1994.

Khamnei et al,. "Neighboring Group Catalysis in the Design of Nucleotide Prodrugs." 39:4109-4115; J Med Chem., 1996.

Khandazhinskaya et al. "Carbocyclic Dinucleoside Polyphosphonates: Interactions with HIV reverse Transcriptase and Antiviral Activity." 45:1284-1291; J Med Chem., 2002.

Kim et al. "Synthesis and Antiviral Activity of (S)-9-[4-Hydroxy-3-(phosphonomethoxy)butly]guanine." 33:1797-1800; J Med Chem., 1990.

Kunz et al. "71. Synthesis of the Glycopeptide Partial Sequence A 80-A84 of Human Fibroblast Interferon." 68:618-622; Helvetica Chimica Acta., 1985.

Lochmuller et al. "Chromatographic Resolution of Enantiomers Selective Review." 113:283-302; J Chromatog., 1975.

Lu et al. "Palladium-Catalyzed Reaction of Aryl Polyfluoroalkanesulfonates with 0,0-Dialkyl Phosphonates." pp. 726-727; Synthesis, 1987.

Maffre-Lafon et al. "Solid Phase Synthesis of Phosphonopeptides from Fmoc Phosphonodipeptides." 35(24):4097-4098; Tet Lett., 1994.

McKenna et al.. "Functional Selectivity in Phosphonate Ester Dealkylation with Bromotrimethylsilane." p. 739; JCS Chem Com., 1979.

Melvin, L.S "An Efficient Synthesis of 2-Hydroxyphenylphosphonates." 22(35):3375-3376; Tet Lett., 1981.

Mikhailopulo et al.. "Pyrophosphoryl Derivatives of 1-(2-Deoxy-3-O-Phosphonomethyl-B- and—D-erythro-Pentofuranosyl) . . . " 19(10-12):1885-1909; Nucls & Nuclt., 2000.

Mitchell et al. "Bioreversible Protection for the Phospho Group: Bioactivation of the Di(4 acyloxybenzyl) and Mono . . . " pp. 2345-2353; J Chem Soc Perkin Trans I., 1992.

Mitsunobu, Oyo " The use of Diethyl Azodicarboxylate and Triphenlyphospine in Synthesis and Transformation of Natural Products." p. 1-28 ; Synthesis, 1981.

Morgan et al. "Structure-Based Design of an Inhibitor of the Zinc Peptidase Thermolysin." 116(8):3251-3260; J Am Chem Soc., 1994.

Morr et al. "Formation of Phostonic Acids During The Reduction of Azidonucleosidephosphonic Acids ." 42:8841-8843 ; Tet Lett., 2001.

Muesing et al. "Nucleic acid structure and expression of the human AIDS/lymphadenopathy retrovirus." 313(7):450-458; Nature, 1985.

Musiol et al. "On the Synthesis of Phosphonamidates Peptides." 59(21):6144-6146;J Org Chem., 1994.

Ohashi et al. "Synthesis of Phosphonosphingoglycolipid Found in Marine Snail *Turbo Cornutus*." 29(10):1189-1192; Tet Lett., 1988.

Okamoto "Optical resolution of dihydropyridine enantiomers by High-performance liquid chromatography using phenylcarbamates ." 513:375-378; Journal of Chromatography, 1990.

Paquette, Leo A. "The Four-Membered Heterocycles." vol. 3; Principals of Modern Heterocyclic Chemistry, 1968.

Paquette, Leo A. "Furan, Pyrrole, and Thiophene." Chptr:4; Principals of Modern Heterocyclic Chemistry, 1968.

Paquette, Leo A. "The Azoles." Chptr:6; Principals of Modern Heterocyclic Chemistry, 1968.

Paquette, Leo A. "The Diazines and S-Triazine." Chptr:9, Principals of Modern Heterocylic Chemistry, 1968.

Patois et al. "2-Alkyl-5,5-dimethyl-1,3,2-dioxaphosphorinan-2-ones—Lithiated Carbanions Synthesis, Stability, and . . . " p. 1577-1581; J Chem Soc Perkin Trans 1, 1990.

Petrakis et al. "Palladium-Catalyzed Substitutions of Triflates Derived from Tyrosine-Containing Peptides and Simpler Hydroxyarenes . . . " 109:2831-2833; J Am Chem Soc., 1987.

Porche, Demetrius James "State of the Art: Antiretroviral and Prophylactic Treatments in HIV/AIDS," 34(1):95-112; Nursing Clin of North Amer., 1999.

Puech et al. "Intracellular delivery of nucleoside monophosphates through a reuctase-mediated activation process." 22:155-174; Antiviral Res., 1993.

Pungente, Weiler "Synthesis and Stereochemical Elucidation of a 14-Membered Ring Phosphonate." 3(5):643-646; Org Lett.,2001.

Quast et al. "Herstellung von Methylphosphonsaure-dichlorid." 490; Synthesis, 1974.

Raner et al. "Reactions of Epoxides Derived from 2'-(3"-Methylbut-s"-enyl)trifluoroacetanilides" 43:609-616; Aust J Chem., 1990.

Ratner et al. "Complete Nucleotide Sequence of the Acquired Immune Deficiency Syndrome Virus Human T-Cell Leukemia Virus Type III." 313:277-284; Nature., 1985.

Redmore, Derek "Phosphorus Derivatives of Nitrogen Heterocycles, 2. Pyridinephosphonic Acid Derivatives." 35(12):4114-4117; J Org Chem., 1970.

Roach et al. "Fluorescence Detection of Alkylphosphonic Acids Using p-(9-Anthroyloxy)phenacyl Bromide." 59:1056-1059; Anal Chem., 1987.

Rosenberg et al. "Synthesis of Potential Prodrugs and Metabolites of 9-(S)-(3-Hydroxy-2-Phosphonylmethoxypropyl)Adenines." 52:2792-2800; Collect Czech Chem Commun., 1987.

Saady et al. "Selective Monodeprotection of Phosphate, Phosphite, Phosphonate, and Phosphoramide Benzyl Esters." 60:2946-2947; J Org Chem., 1995.

Serafinowska et al. "Synthesis and in Vivo Evaluation of Prodrugs of 9-[2-(Phosphonomethoxy)ethoxy]adenine." 38:1372-1379;J Med Chem., 1995.

Silverberg et al. "A Simple, Rapid and Efficient Protocol for the Selective Phophorylation of Phenols with Dibenzyl Phosphite." 37(16):771-774; Tet Lett., 1996.

Skwarczynski et al. "Alkylation of Potassium 1-(N-Benzloxycarbonyl-Amino) Alkylphosphonates and Phosphinates in the Presence of 18-Crown-6." Syn Comm.; 25:3565-3571, 1995.

Smith et al. "Development and significance of nucleoside drug resistance in infection caused by the human immunodeficiency virus type 1." 17:226-243; Clin Invest Med., 1994.

Stuttgart "Protecting Groups: An Overview." pp. 1-20; Protecting Groups, 1994.

Stuttgart "Carbonyl Protecting Groups." pp. 155-184; Protecting Groups, 1994.

Stuttgart "Carboxyl Protecting Groups." pp. 118-154;Protecting Groups,1994.

Sun et al. "A General Synthesis of Dioxolenone Prodrug Moieties." 43:1161-1164; Tet Lett.,2002.

Thomson et al. "Synthesis and Bioactivation of Bis(aroyloxymethyl)and Mono(aroyloxymethyl) Esters of Benzylphosphonate . . . " 1:2303-2308; J Chem Soc Perkin Comm I., 1993.

Van Der Laan et al. "Optimization of the Binding Properties of PNA-(5')-DNA Chimerae." 8:663-668; Bioorg Med Chem Lett., 1998.

Van Der Laan et al. "An Approach Towards the Synthesis of Oligomers Containing a N-2 Hydroxyethyl-aminomethylphosphonate . . . " 37(43):7857-7860; Tet Lett., 1996.

Vieira de Almeida et al. "Synthesis of Deoxy Phosphatidylinositol Analogues and Phosphonate Isosters . . . " 55:12997-13010; Tetrahedron., 1999.

Von Der Helm, Klaus "Retroviral Proteases: Structure, Function and Inhibition From a Non-Anticipated Viral Enzyme To The Target . . . " 377:765-774; Biol Chem., 1996.

Watanabe et al. "Dibenzyl Phosphorofluoridate, A New Phosphorylating Agent." 29(45):5763-5764; Tet Lett., 1988.

Wissner et al."Analogues of Platelet Activating Factor. 6 Mono-and bis-aryl Phosphate Antagonists of Platelet Activating Factor." 35:1650-1662; J Med Chem., 1992.

Yamauchi et al. "Synthesis of Peptides Analogs Containing(2-aminoethyl)phosphonic acid (cilliatine)." 49(7):1158-1163;J Org Chem., 1984.

Guanti, G. et al. (1995) "Synthesis of optically pure "open-chain" nucleotide Derivatives of Asymmetrized Tris (hydroxymethyl) methane" Tetrahedron 51 (35): 9737-9746.

Holy, A. et al. (1988) "Synthesis and Evaluation of Acyclic Nucleotide Analogs" Nucleosides & Nucleotides 7(5-6):667-670.

* cited by examiner

NUCLEOBASE PHOSPHONATE ANALOGS FOR ANTIVIRAL TREATMENT

CROSS-REFERENCE TO RELATED APPLICATION

The application claims the benefit of U.S. Provisional Application No. 60/491,123, filed Jul. 30, 2003.

FIELD OF THE INVENTION

The invention relates generally to compounds with antiviral activity and more specifically with anti-reverse transcriptase properties.

BACKGROUND OF THE INVENTION

Human immunodeficiency virus (HIV) infection and related disease is a major public health problem worldwide. The retrovirus human immunodeficiency virus type 1 (HIV-1), a member of the primate lentivirus family (DeClercq E (1994) *Annals of the New York Academy of Sciences*, 724: 438-456; Barre-Sinoussi F (1996) *Lancet*, 348:31-35), is generally accepted to be the causative agent of acquired immunodeficiency syndrome (AIDS) Tarrago etal *FASEB Journal* 1994, 8:497-503). AIDS is the result of repeated replication of HIV-1 and a decrease in immune capacity, most prominently a fall in the number of CD4+ lymphocytes. The mature virus has a single stranded RNA genome that encodes 15 proteins (Frankel etal (1998) *Annual Review of Biochemistry*, 67:1-25; Katz etal (1994) *Annual Review of Biochemistry*, 63:133-173), including three key enzymes: (i) protease (Prt) (von der Helm K (1996) *Biological Chemistry*, 377:765-774); (ii) reverse transcriptase (RT) (Hottiger etal (1996) *Biological Chemistry Hoppe-Seyler*, 377:97-120), an enzyme unique to retroviruses; and (iii) integrase (Asante etal (1999) *Advances in Virus Research* 52:351-369; Wlodawer A (1999) *Advances in Virus Research* 52:335-350; Esposito etal (1999) *Advances in Virus Research* 52:319-333). Protease is responsible for processing the viral precursor polyproteins, integrase is responsible for the integration of the double stranded DNA form of the viral genome into host DNA and RT is the key enzyme in the replication of the viral genome. In viral replication, RT acts as both an RNA- and a DNA-dependent DNA polymerase, to convert the single stranded RNA genome into double stranded DNA. Since virally encoded Reverse Transcriptase (RT) mediates specific reactions during the natural reproduction of the virus, inhibition of HIV RT is an important therapeutic target for treatment of HIV infection and related disease.

Sequence analysis of the complete genomes from several infective and non-infective HIV-isolates has shed considerable light on the make-up of the virus and the types of molecules that are essential for its replication and maturation to an infective species. The HIV protease is essential for the processing of the viral gag and gag-pol polypeptides into mature virion proteins. L. Ratner, et al., Nature, 313:277-284 (1985); L. H. Pearl and W. R. Taylor, Nature, 329:351 (1987). HIV exhibits the same gag/pol/env organization seen in other retroviruses. L. Ratner, et al., above; S. Wain-Hobson, et al., Cell, 40:9-17 (1985); R. Sanchez-Pescador, et al., Science, 227:484-492 (1985); and M. A. Muesing, et al., Nature, 313: 450-458 (1985).

Drugs approved in the United States for AIDS therapy include nucleoside inhibitors of RT (Smith et al (1994) *Clinical Investigator*, 17:226-243), protease inhibitors and non-nucleoside RT inhibitors (NNRTI), (Johnson et al (2000) *Advances in Internal Medicine*, 45 (1-40; Porche D J (1999) *Nursing Clinics of North America*, 34:95-112).

Unsaturated linker phosphonate derivatives purine and pyrmidine compounds have been reported to be useful as antiviral agents (US 2003/0004345A1; EP 0532423A1; EP 0618214A1; EP 0701562B1; U.S. Pat. No. 5,817,647; U.S. Pat. No. 5,922,696; WO 94/22882).

There is a need for anti-HIV therapeutic agents, i.e. drugs having improved antiviral and pharmacokinetic properties with enhanced activity against development of HIV resistance, improved oral bioavailability, greater potency and extended effective half-life in vivo.

Combination therapy of PI and RT inhibitors has proven to be highly effective in suppressing viral replication to unquantifiable levels for a sustained period of time. Also, combination therapy with RT and protease inhibitors have shown synergistic effects in suppressing HIV replication. Unfortunately, many patients currently fail combination therapy due to the development of drug resistance, non-compliance with complicated dosing regimens, pharmacokinetic interactions, toxicity, and lack of potency. Therefore, there is a need for new HIV reverse transcriptase inhibitors that are synergistic in combination with other HIV inhibitors.

Improving the delivery of drugs and other agents to target cells and tissues has been the focus of considerable research for many years. Though many attempts have been made to develop effective methods for importing biologically active molecules into cells, both in vivo and in vitro, none has proved to be entirely satisfactory. Optimizing the association of the inhibitory drug with its intracellular target, while minimizing intercellular redistribution of the drug, e.g. to neighboring cells, is often difficult or inefficient.

Most agents currently administered to a patient parenterally are not targeted, resulting in systemic delivery of the agent to cells and tissues of the body where it is unnecessary, and often undesirable. This may result in adverse drug side effects, and often limits the dose of a drug (e.g., cytotoxic agents and other anti-cancer or anti-viral drugs) that can be administered. By comparison, although oral administration of drugs is generally recognized as a convenient and economical method of administration, oral administration can result in either (a) uptake of the drug through the cellular and tissue barriers, e.g. blood/brain, epithelial, cell membrane, resulting in undesirable systemic distribution, or (b) temporary residence of the drug within the gastrointestinal tract. Accordingly, a major goal has been to develop methods for specifically targeting agents to cells and tissues. Benefits of such treatment includes avoiding the general physiological effects of inappropriate delivery of such agents to other cells and tissues, such as uninfected cells. Intracellular targeting may be achieved by methods and compositions which allow accumulation or retention of biologically active agents, i.e. active metabolites, inside cells.

SUMMARY OF THE INVENTION

The present invention provides novel compounds with activity against infectious viruses. The compounds of the invention may inhibit retroviral reverse transcriptases and thus inhibit the replication of the virus. They are useful for treating human patients infected with a human retrovirus, such as human immunodeficiency virus (strains of HIV-1 or HIV-2) or human T-cell leukemia viruses (HTLV-I or HTLV-II) which results in acquired immunodeficiency syndrome (AIDS) and/or related diseases.

The present invention relates generally to the accumulation or retention of therapeutic compounds inside cells. The invention is more particularly related to attaining high concentrations of active metabolite molecules in HIV infected cells. Intracellular targeting may be achieved by methods and compositions which allow accumulation or retention of biologically active agents inside cells. Such effective targeting may be applicable to a variety of therapeutic formulations and procedures.

In one aspect, the invention includes compounds having Formula I:

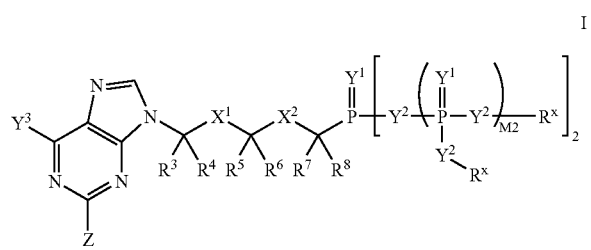

Formula I compounds are substituted with one or more covalently attached phosphonate groups.

Another aspect of the invention includes Formula II compounds where NUCLEOBASE can be any naturally-occurring nucleobase, e.g. purine, pyrimidine, or other synthetic nucleobase analog capable of Watson-Crick type base-pairing, according to the formula:

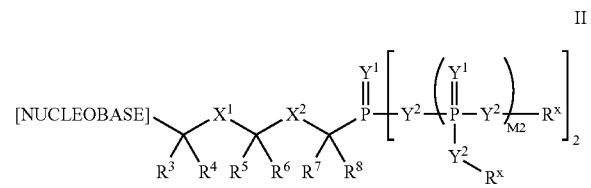

Another aspect of the invention provides a pharmaceutical combination comprising an effective amount of a compound selected from Formula I or II, and a second composition having anti-HIV properties.

Another aspect of the invention provides a method for the treatment or prevention of the symptoms or effects of an HIV infection in an infected animal which comprises administering to, i.e. treating, said animal with a pharmaceutical composition or formulation comprising an effective amount of a Formula I or II compound.

Another aspect of the invention provides a method for the treatment or prevention of the symptoms or effects of an HIV infection in an infected animal which comprises administering to, i.e. treating, said animal with a pharmaceutical combination composition or formulation comprising an effective amount of a Formula I or II compound, and a second compound having anti-HIV properties.

The invention provides a pharmaceutical composition comprising an effective amount of a Formula I or II compound, or a pharmaceutically acceptable salt thereof, in combination with a pharmaceutically acceptable diluent or carrier.

This invention pertains to a method of increasing cellular accumulation and retention of drug compounds, thus improving their therapeutic and diagnostic value.

The invention also provides a method of inhibiting HIV, comprising administering to a mammal infected with HIV (HIV positive) an amount of a Formula I or II compound, effective to inhibit the growth of said HIV infected cells.

The invention also provides a Formula I or II compound for use in medical therapy (preferably for use in treating cancer, e.g. solid tumors), as well as the use of a Formula I or II compound for the manufacture of a medicament useful for the treatment of cancer, e.g. solid tumors.

The invention also provides processes and novel intermediates disclosed herein which are useful for preparing Formula I or II compounds of the invention.

In another aspect of the invention, the activity of HIV reverse transcriptase is inhibited by a method comprising the step of treating a sample suspected of containing HIV virus with a Formula I or II compound.

Another aspect of the invention provides a method for inhibiting the activity of HIV reverse transcriptase comprising the step of contacting a sample suspected of containing HIV virus with a Formula I or II compound.

In other aspects, novel methods for synthesis analysis, separation, isolation, purification, characterization, and testing of the compounds of this invention are provided.

DETAILED DESCRIPTION OF EXEMPLARY EMBODIMENTS

Reference will now be made in detail to certain embodiments of the invention, examples of which are illustrated in the accompanying description, structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims.

Definitions

Unless stated otherwise, the following terms and phrases as used herein are intended to have the following meanings:

The terms "phosphonate" and "phosphonate group" mean a functional group or moiety within a molecule that comprises at least one phosphorus-carbon bond, and at least one phosphorus-oxygen double bond. The phosphorus atom is further substituted with oxygen, sulfur, or nitrogen substituents. These substituents may be part of a prodrug moiety. As defined herein, "phosphonate" and "phosphonate group" include molecules with phosphonic acid, phosphonic monoester, phosphonic diester, phosphonamidate, phosphondiamidate and phosphonthioate functional groups.

The term "prodrug" as used herein refers to any compound that when administered to a biological system generates the drug substance, i.e. active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically-active compound.

"Pharmaceutically acceptable prodrug" refers to a compound that is metabolized in the host, for example hydrolyzed or oxidized, by either enzymatic action or by general acid or base solvolysis, to form an active ingredient. Typical examples of prodrugs of the compounds of the invention have biologically labile protecting groups on a functional moiety of the compound. Prodrugs include compounds that can be oxidized, reduced, aminated, deaminated, esterified, deesterified, alkylated, dealkylated, acylated, deacylated, phosphorylated, dephosphorylated, photolyzed, hydrolyzed, or other functional group change or conversion involving forming or breaking chemical bonds on the prodrug.

"Prodrug moiety" means a labile functional group which separates from the active inhibitory compound during metabolism, systemically, inside a cell, by hydrolysis, enzymatic cleavage, or by some other process (Bundgaard, Hans, "Design and Application of Prodrugs" in *Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the phosphonate prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy.

A prodrug moiety includes an active metabolite or drug itself.

Exemplary prodrug moieties include the hydrolytically sensitive or labile acyloxymethyl esters —$CH_2C(=O)R^9$ and acyloxymethyl carbonates —$CH_2C(=O)OR^9$ where $R^9$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al (1983) *J. Pharm. Sci.* 72: 324; also U.S. Pat. Nos. 4,816,570, 4,968,788, 5663159 and 5792756. In certain compounds of the invention, a prodrug moiety is part of a phosphonate group. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —$CH_2C(=O)C(CH_3)_3$. An exemplary acyloxymethyl carbonate prodrug moiety is pivaloyloxymethylcarbonate (POC) —$CH_2C(=O)OC(CH_3)_3$.

The phosphonate group may be a phosphonate prodrug moiety. The prodrug moiety may be sensitive to hydrolysis, such as, but not limited to a pivaloyloxymethyl carbonate (POC) or POM group. Alternatively, the prodrug moiety may be sensitive to enzymatic potentiated cleavage, such as a lactate ester or a phosphonamidate-ester group.

Aryl esters of phosphorus groups, especially phenyl esters, are reported to enhance oral bioavailability (DeLambert et al (1994) *J. Med. Chem.* 37: 498). Phenyl esters containing a carboxylic ester ortho to the phosphate have also been described (Khamnei and Torrence, (1996) *J. Med. Chem.* 39:4109-4115). Benzyl esters are reported to generate the parent phosphonic acid. In some cases, substituents at the ortho-orpara-position may accelerate the hydrolysis. Benzyl analogs with an acylated phenol or an alkylated phenol may generate the phenolic compound through the action of enzymes, e.g. esterases, oxidases, etc., which in turn undergoes cleavage at the benzylic C—O bond to generate the phosphoric acid and the quinone methide intermediate. Examples of this class of prodrugs are described by Mitchell et al (1992) *J. Chem. Soc. Perkin Trans.* 12345; Brook et al WO 91/19721. Still other benzylic prodrugs have been described containing a carboxylic ester-containing group attached to the benzylic methylene (Glazier et al WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al (1993) *Antiviral Res.*, 22: 155-174; Benzaria et al (1996) *J. Med. Chem.* 39: 4958). Cyclic phosphonate esters have also been described as prodrugs of phosphorus-containing compounds (Erion et al, U.S. Pat. No. 6,312,662).

"Protecting group" refers to a moiety of a compound that masks or alters the properties of a functional group or the properties of the compound as a whole. The chemical substructure of a protecting group varies widely. One function of a protecting group is to serve as intermediates in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g. alcohols, be physiologically acceptable, although in general it is more desirable if the products are pharmacologically innocuous.

Any reference to any of the compounds of the invention also includes a reference to a physiologically acceptable salt thereof. Examples of physiologically acceptable salts of the compounds of the invention include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound of an hydroxy group include the anion of said compound in combination with a suitable cation such as Na+ and $NX_4^+$ (wherein X is independently selected from H or a $C_1$-$C_4$ alkyl group).

For therapeutic use, salts of active ingredients of the compounds of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

"Alkyl" is $C_1$-$C_{18}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$).

"Alkenyl" is $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to: ethylene or vinyl (—$CH=CH_2$), allyl (—$CH_2CH=CH_2$), cyclopentenyl (—$C_5H_7$), and 5-hexenyl (—$CH_2CH_2CH_2CH_2CH=CH_2$)

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to: acetylenic (—C≡CH) and propargyl (—$CH_2$C≡CH), "Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—$CH_2$—) 1,2-ethyl (—$CH_2CH_2$—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene (—C≡C—), propargyl (—$CH_2$C≡C—), and 4-pentynyl (—$CH_2CH_2CH_2$C≡CH—).

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms.

R is $C_1$-$C_8$ alkyl, $C_1$-$C_8$ substituted alkyl, $C_1$-$C_8$ alkenyl, $C_1$-$C_8$, $C_1$-$C_8$ alkynyl, $C_1$-$C_8$, $C_6$-$C_{20}$ aryl, $C_6$-$C_{20}$ substituted aryl, $C_2$-$C_{20}$ heteroaryl, $C_2$-$C_{20}$;

"Substituted alkyl", "substituted alkenyl", "substituted alkynyl", "substituted aryl", "substituted heteroaryl", and "substituted arylalkyl" mean alkyl, alkenyl, alkynyl, aryl, heteroaryl, and arylalkyl respectively, in which one or more hydrogen atoms are each independently replaced with a substituent. Typical substituents include, but are not limited to, —X, —R, —O—, —OR, —SR, —S⁻, —$NR_2$, —$NR_3$, =NR, —$CX_3$, —CN, —OCN, —SCN, —N=C=O, —NCS, —NO, —$NO_2$, =$N_2$, —$N_3$, NC(=O)R, —C(=O)R, —C(=O)NRR —S(=O)$_2$O⁻, —S(=O)$_2$OH, —S(=O)$_2$R, —OS(=O)$_2$OR, —S(=O)$_2$NR, —S(=O)R, —OP(=O)O$_2$RR, —P(=O)O$_2$RR —P(=O)(O⁻)$_2$, —P(=O)(OH)$_2$, —C(=O)R, —C(=O)X, —C(S)R, —C(O)OR, —C(O)O⁻, —C(S)OR, —C(O)SR, —C(S)SR, —C(O)NRR, —C(S)NRR, —C(NR)NRR, where each X is independently a halogen: F, Cl, Br, or I; and each R is independently —H, alkyl, aryl, heterocycle, protecting group or prodrug moiety. Alkylene, alkenylene, and alkynylene groups may also be similarly substituted.

"Heterocycle" as used herein includes by way of example and not limitation these heterocycles described in Paquette, Leo A.; "Principles of Modem Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566.

Examples of heterocycles include by way of example and not limitation, pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

One embodiment of the bis-tetrahydrofuranyl group is:

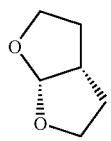

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or 0-carboline. Still more typically, nitrogen bonded heterocycles include I-aziridyl, 1-azetedyl, 1-pyrrolyl, 1-imidazolyl, 1-pyrazolyl, and 1-piperidinyl.

"Carbocycle" means a saturated, unsaturated or aromatic ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl.

"Nucleobase" means any nitrogen-containing heterocyclic moiety capable of forming Watson-Crick hydrogen bonds in pairing with a complementary nucleobase or nucleobase analog, e.g. a purine, a 7-deazapurine, or a pyrimidine. Typical nucleobases are the naturally occurring nucleobases: adenine, guanine, cytosine, uracil, thymine, and analogs of the naturally occurring nucleobases, e.g. 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, pyrazolo[3,4-D]pyrimidines (U.S. Pat. Nos. 6,143,877 and 6,127,121; WO 01/38584), and ethenoadenine (Fasman (1989) in *Practical Handbook of Biochemistry and Molecular Biology*, pp. 385-394, CRC Press, Boca Raton, Fla.).

"Linker" or "link" means a chemical moiety comprising a covalent bond or a chain of atoms. Linkers include repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and 1, D and L, or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

HIV Reverse transcriptase Inhibitor Compounds

The compounds of the invention include those with HIV reverse transcriptase inhibitory activity. In particular, the compounds include HIV reverse transcriptase inhibitors. The compounds of the inventions bear a phosphonate group, which may be a prodrug moiety.

Whenever a compound described herein is substituted with more than one of the same designated group, e.g., "R" or "$R^1$", then it will be understood that the groups may be the same or different, i.e., each group is independently selected. Wavy lines indicate the site of covalent bond attachments to the adjoining substructures, groups, moieties, or atoms.

Compounds of the invention are set forth in the schemes, examples, descriptions and claims below and include the invention includes compounds having Formulas I and II:

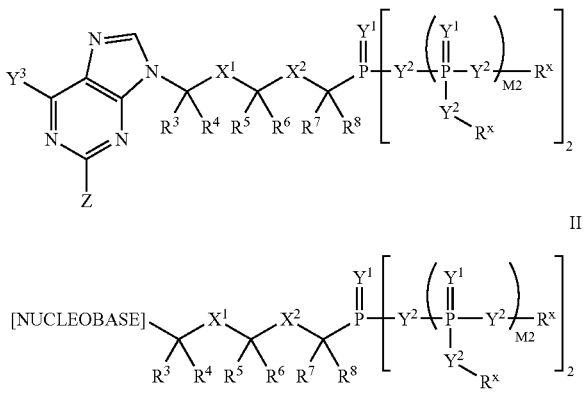

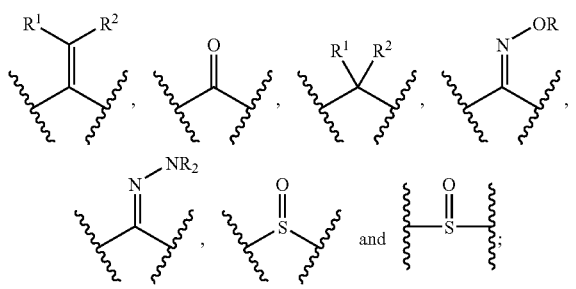

wherein:
X$^1$ is selected from:

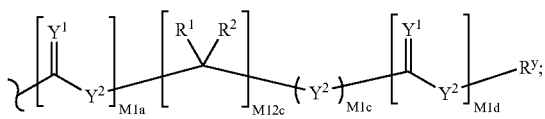

X$^2$ is selected from O, NR and S;
Y$^1$ is independently O, S, NR, $^+$N(O)(R), $^+$N(OR), $^+$N(O)(OR), or N—NR$_2$;
Y$^2$ is independently a bond, O, NR, $^+$N(O)(R), $^+$N(OR), $^+$N(O)(OR), N—NR$_2$, —S(O)$_{M2}$—, or —S(O)$_{M2}$—S(O)$_{M2}$—;
Y$^3$ and Z are independently selected from H, OH, OR, NR$_2$, CN, NO$_2$, F, Cl, Br, and I;
R$^x$ is independently H, W$^3$, a protecting group, or the formula:

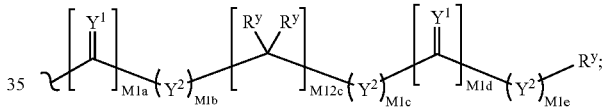

wherein:
M1a, M1c, and M1d are independently 0 or 1;
M12c is 0, 1, 2, 3, 4, 5, 6, 7, 8, 9, 10, 11 or 12; and
R$^y$ is independently H, W$^3$, or a protecting group;
M2 is 0, 1 or 2;
R$^1$, R$^2$, R$^3$, R$^4$, R$^5$, R$^6$, R$^7$, and R$^8$ are independently selected from H, F, Cl, Br, I, OH, —C(=Y$^1$)R, —C(=Y$^1$)OR or —C(=Y$^1$)N(R)$_2$, —N(R)$_2$, —$^+$N(R)$_3$, —SR, —S(O)R, —S(O)$_2$R, —S(O)(OR$^x$), —S(O)$_2$(OR$^x$), —OC(=Y$^1$)R$^x$, —OC(=Y$^1$)OR$^x$, —OC(=Y$^1$)(N(R$^x$)$_2$), —SC(=Y$^1$)R$^x$, —SC(=Y$^1$)OR$^x$, —SC(=Y$^1$)(N(R$^x$)$_2$), —N(R$^x$)C(=Y$^1$)R$^x$, —N(R$^x$)C(=Y$^1$)OR$^x$, or —N(R$^x$)C(=Y$^1$)N(R$^x$)$_2$, amino (—NH$_2$), ammonium (—NH$_3$+), alkylamino, dialkylamino, trialkylammonium, C$_1$-C$_8$ alkyl, C$_1$-C$_8$ alkylhalide, carboxylate, sulfate, sulfamate, sulfonate, 5-7 membered ring sultam, C$_1$-C$_8$ alkylsulfonate, C$_1$-C$_8$ alkylamino, 4-dialkylaminopyridinium, C$_1$-C$_8$ alkylhydroxyl, C$_1$-C$_8$ alkylthiol, alkylsulfone (—SO$_2$R), arylsulfone (—SO$_2$Ar), arylsulfoxide (—SOAr), arylthio (—SAr), sulfonamide (—SO$_2$NR$_2$), alkylsulfoxide (—SOR), ester (—C(=O)OR), amido (—C(=O)NR$_2$), 5-7 membered ring lactam, 5-7 membered ring lactone, nitrile (—CN), azido (—N$_3$), nitro (—NO$_2$), C$_1$-C$_8$ alkoxy (—OR), C$_1$-C$_8$ alkyl, C$_1$-C$_8$ substituted alkyl, C$_1$-C$_8$ alkenyl, C$_1$-C$_8$ substituted alkenyl, C$_1$-C$_8$ alkynyl, C$_1$-C$_8$ substituted alkynyl, C$_6$-C$_{20}$ aryl, C$_6$-C$_{20}$ substituted aryl, C$_2$-C$_{20}$ heteroaryl, C$_2$-C$_{20}$ substituted heteroaryl, polyethyleneoxy, and W3; or
when taken together, two of R$^1$, R$^2$, R$^3$, R$^4$, R$^5$, R$^6$, R$^7$, and R$^8$ form a carbocyclic ring of 3 to 7 carbon atoms;
R is C$_1$-C$_8$ alkyl, C$_1$-C$_8$ substituted alkyl, C$_1$-C$_8$ alkenyl, C$_1$-C$_8$ substituted alkenyl, C$_1$-C$_8$ alkynyl, C$_1$-C$_8$ substituted alkynyl, C$_6$-C$_{20}$ aryl, C$_6$-C$_{20}$ substituted aryl, C$_2$-C$_{20}$ heteroaryl, C$_2$-C$_{20}$ substituted heteroaryl;
W$^3$ is W$^4$ or W$^5$;
W$^4$ is R, —C(Y$^1$)R, —C(Y$^1$)W$^5$, —SO$_2$R, or —SO$_2$W$^5$; and
W$^5$ is a carbocycle or heterocycle wherein W$^5$ is independently substituted with 0 to 3 R groups.
Formula I and II compounds where R$^3$, R$^4$, R$^5$, R$^6$, R$^7$, and R$^8$ are each H, Y$^1$ and Y$^2$ are O, M2 is 0, and R$^x$ is H are excluded from the invention.
Alternatively, R$^x$ is a group of the formula:

wherein:
m1a, m1b, m1c, m1d and m1e are independently 0 or 1;
m12c is 0, 1, 2, 3, 4, 5, 6, 7, 8, 9, 10, 11 or 12;
R$^y$ is H, W$^3$, R$^2$ or a protecting group;

provided that:
if m1a, m12c, and m1d are 0, then m1b, m1c and m1e are 0;
if m1a and m12c are 0 and m1d is not 0, then m1b and m1c are 0;
if m1a and m1d are 0 and m12c is not 0, then m1b and at least one of m1c and m1e are 0;
if m1a is 0 and m12c and m1d are not 0, then m1b is 0;
if m12c and m1d are 0 and m1a is not 0, then at least two of m1b, m1c and m1e are 0;
if m12c is 0 and m1a and m1d are not 0, then at least one of m1b and m1c are 0; and
if m1d is 0 and m1a and m12c are not 0, then at least one of m1c and m1e are 0.
M2 is 0, 1 or 2;
M12a is 1, 2, 3, 4, 5, 6, 7, 8, 9, 10, 11 or 12; and
M12b is 0, 1, 2, 3, 4, 5, 6, 7, 8, 9, 10, 11 or 12.
W$^5$ carbocycles and W$^5$ heterocycles may be independently substituted with 0 to 3 R$^2$ groups. W$^5$ may be a saturated, unsaturated or aromatic ring comprising a mono- or bicyclic carbocycle or heterocycle. W$^5$ may have 3 to 10 ring atoms, e.g., 3 to 7 ring atoms. The W$^5$ rings are saturated when containing 3 ring atoms, saturated or mono-unsaturated when containing 4 ring atoms, saturated, or mono- or di-unsaturated when containing 5 ring atoms, and saturated, mono- or di-unsaturated, or aromatic when containing 6 ring atoms.

A $W^5$ heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). $W^5$ heterocyclic monocycles may have 3 to 6 ring atoms (2 to 5 carbon atoms and 1 to 2 heteroatoms selected from N, O, and S); or 5 or 6 ring atoms (3 to 5 carbon atoms and 1 to 2 heteroatoms selected from N and S). $W^5$ heterocyclic bicycles have 7 to 10 ring atoms (6 to 9 carbon atoms and 1 to 2 heteroatoms selected from N, O, and S) arranged as a bicyclo [4,5], [5,5], [5,6], or [6,6] system; or 9 to 10 ring atoms (8 to 9 carbon atoms and 1 to 2 hetero atoms selected from N and S) arranged as a bicyclo [5,6] or [6,6] system. The $W^5$ heterocycle may be bonded to $Y^2$ through a carbon, nitrogen, sulfur or other atom by a stable covalent bond.

$W^5$ heterocycles include for example, pyridyl, dihydropyridyl isomers, piperidine, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl. $W^5$ also includes, but is not limited to, examples such as:

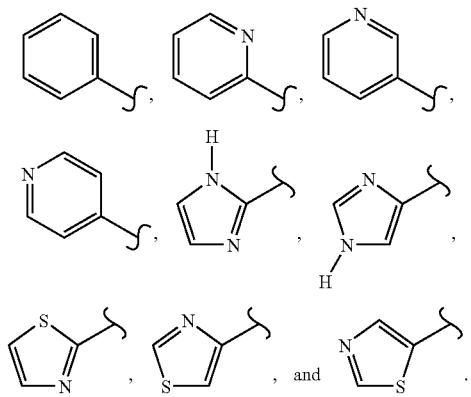

$W^5$ carbocycles and heterocycles may be independently substituted with 0 to 3 R groups, as defined above. For example, substituted $W^5$ carbocycles include:

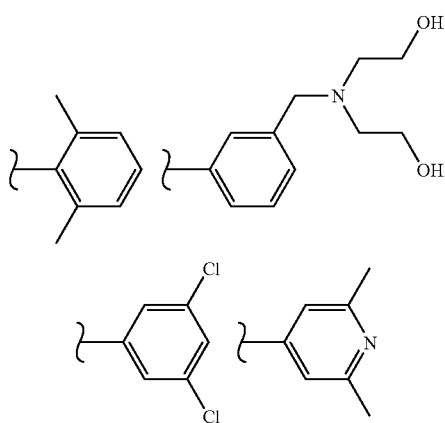

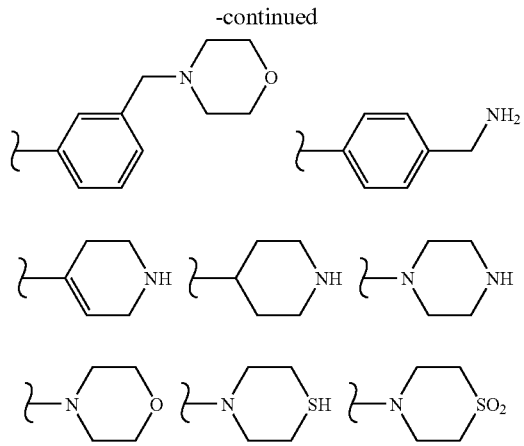

Examples of substituted phenyl carbocycles include:

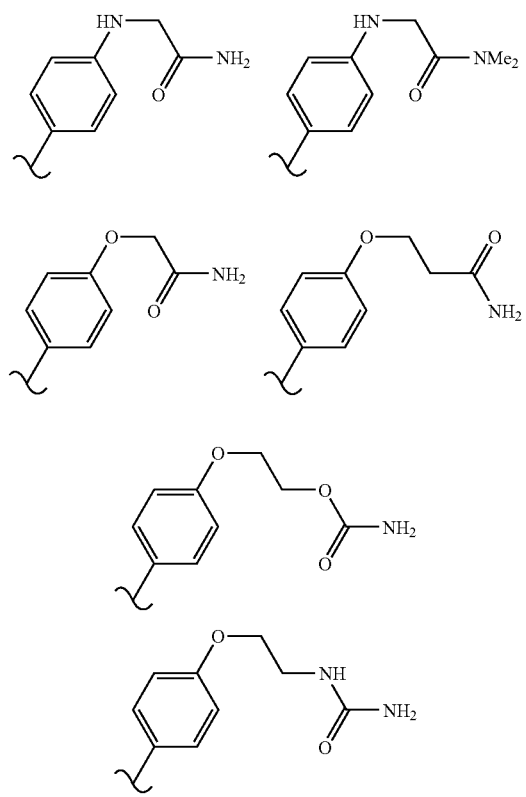

Embodiments of Formula I and II compounds include substructures where M2 is 0, such as:

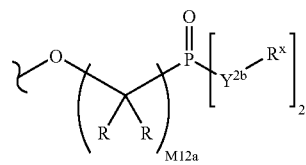

Another embodiment of Formula I and II include the substructures:

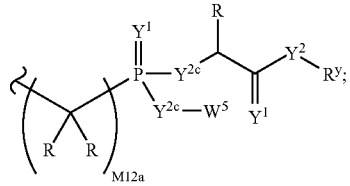

where $Y^{2c}$ is O, $N(R^y)$ or S. For example, $R^1$ may be H and n may be 1.

Another embodiment of Formula I and II compounds include the substructures:

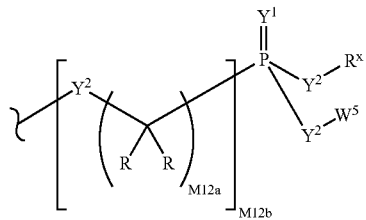

where $W^5$ is a carbocycle such as phenyl or substituted phenyl. Such embodiments include:

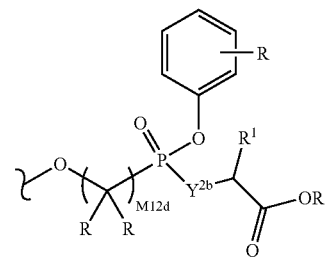

where $Y^{2b}$ is O or $N(R^x)$; M12d is 1, 2, 3, 4, 5, 6, 7 or 8; and the phenyl carbocycle is substituted with 0 to 3 $R^2$ groups. Such embodiments of Formula I include phenyl phosphonamidate amino acid, e.g. alanate esters and phenyl phosphonate-lactate esters:

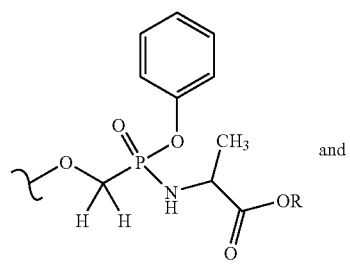

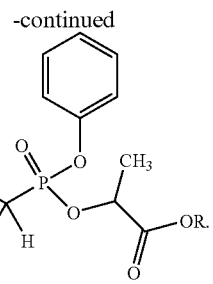

The chiral carbon of the amino acid and lactate moieties may be either the R or S configuration or the racemic mixture.

Embodiments of $R^x$ include esters, carbamates, carbonates, thioesters, amides, thioamides, and urea groups:

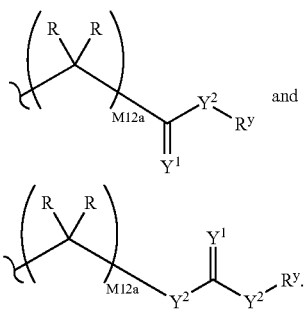

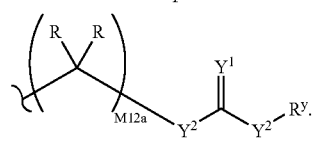

Exemplary embodiments of Formula I compounds include, but are not limited to, structures:

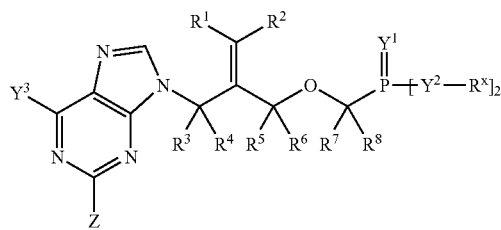

Cellular Accumulation

One aspect of the invention is HIV reverse transcriptase (RT) inhibitor compounds capable of accumulating in human PBMC (peripheral blood monocyte cells).

Optionally, the compounds of the invention demonstrate improved intracellular half-life of the compounds or intracellular metabolites of the compounds in human PBMC when compared to analogs of the compounds not having the phosphonate or phosphonate prodrug. Typically, the half-life is improved by at least about 50%, more typically at least in the range 50-100%, still more typically at least about 100%, more typically yet greater than about 100%.

In one embodiment, the intracellular half-life of a metabolite of the compound in human PBMC is improved when compared to an analog of the compound not having the phosphonate or phosphonate prodrug. In such embodiments, the metabolite is typically generated intracellularly, more typically, it is generated within human PBMC. Still more typically, the metabolite is a product of the cleavage of a phosphonate prodrug within human PBMCs. More typically yet, the phosphonate prodrug is cleaved to form a metabolite having at least one negative charge at physiological pH. Most typically, the phosphonate prodrug is enzymatically cleaved within human PBMC to form a phosphonate having at least one active hydrogen atom of the form P—OH.

Exemplary Enumerated Compounds—Linker Diversity

The following exemplary enumerated compounds include phosphonic acid moieties and demonstrate a non-limiting range of structural diversity in the linker between the nucleobase and phosphonate group. The compounds of the invention include structural diversity within the definitions of nucleobase and phosphonate group, as well.

The compounds of the invention indicating linker diversity include:

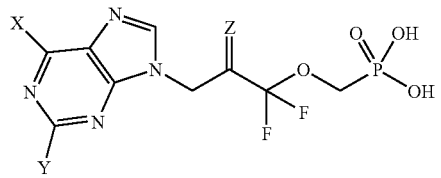

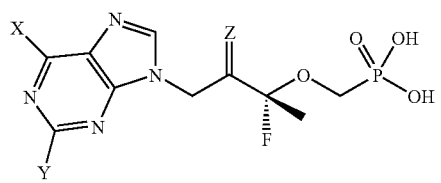

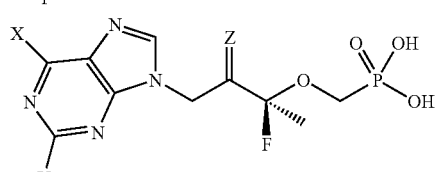

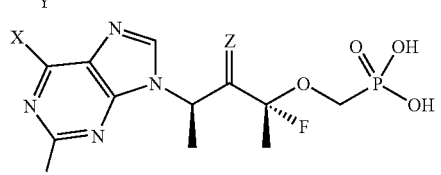

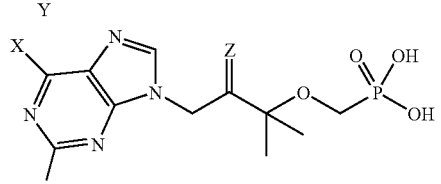

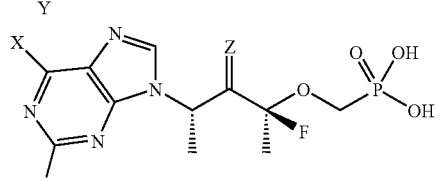

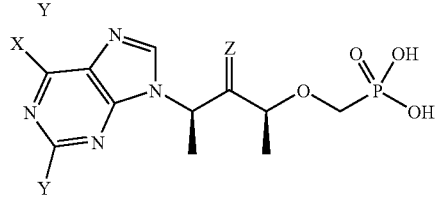

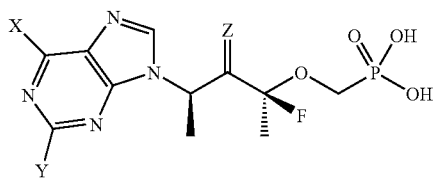

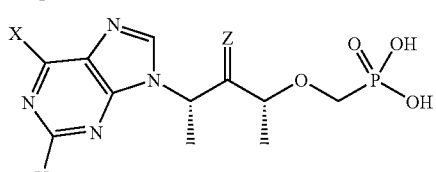

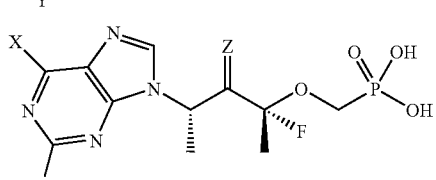

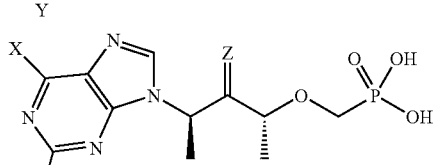

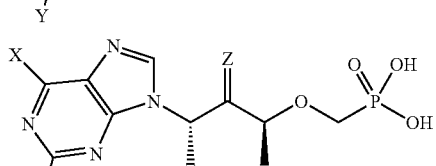

where Z = $R_1\frown R_2$ and $R_1$, $R_2$ are independently H, Me
and where X and Y are independently H, $C_1$, $NH_2$, OH, F The compounds of the invention also include:

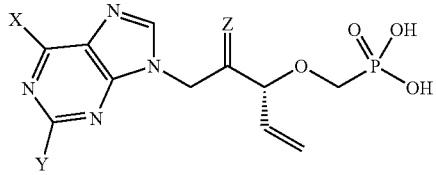

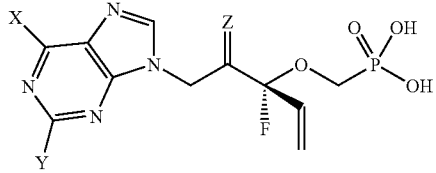

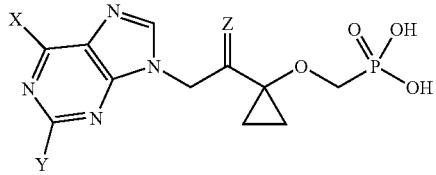

-continued
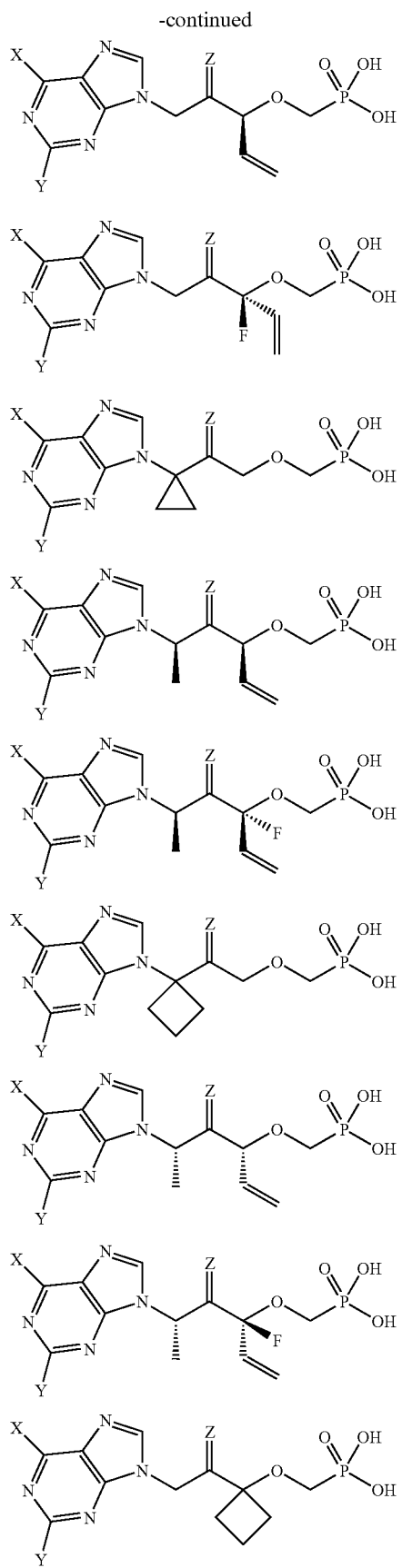
-continued
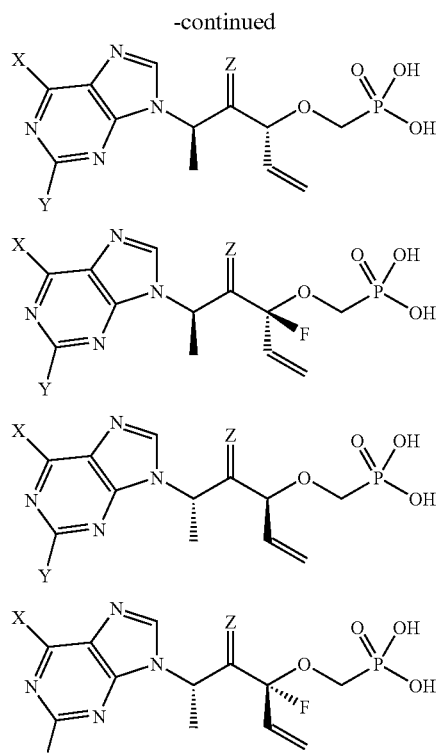
where Z = R₁———R₂
and $R_1$, $R_2$ are independently H, Me
and where X and Y are independently H, Cl, $NH_2$, OH, F
The compounds of the invention also include:
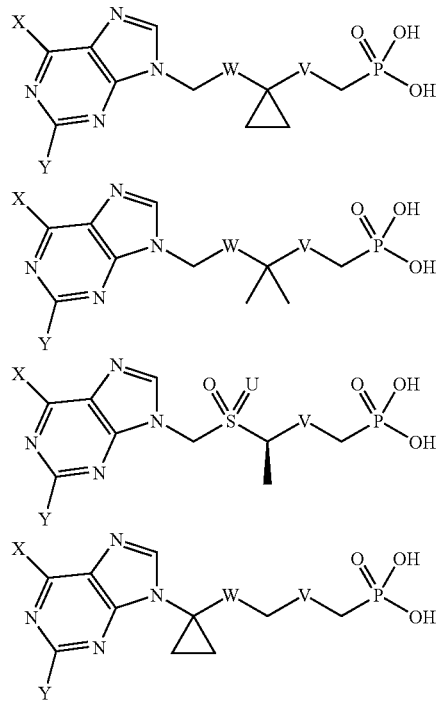

-continued
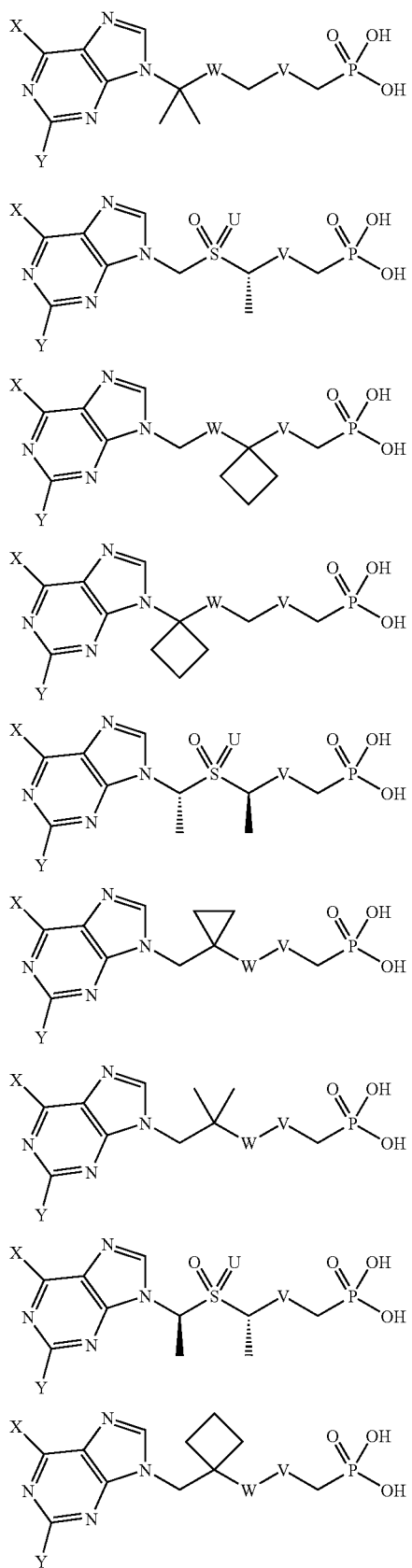
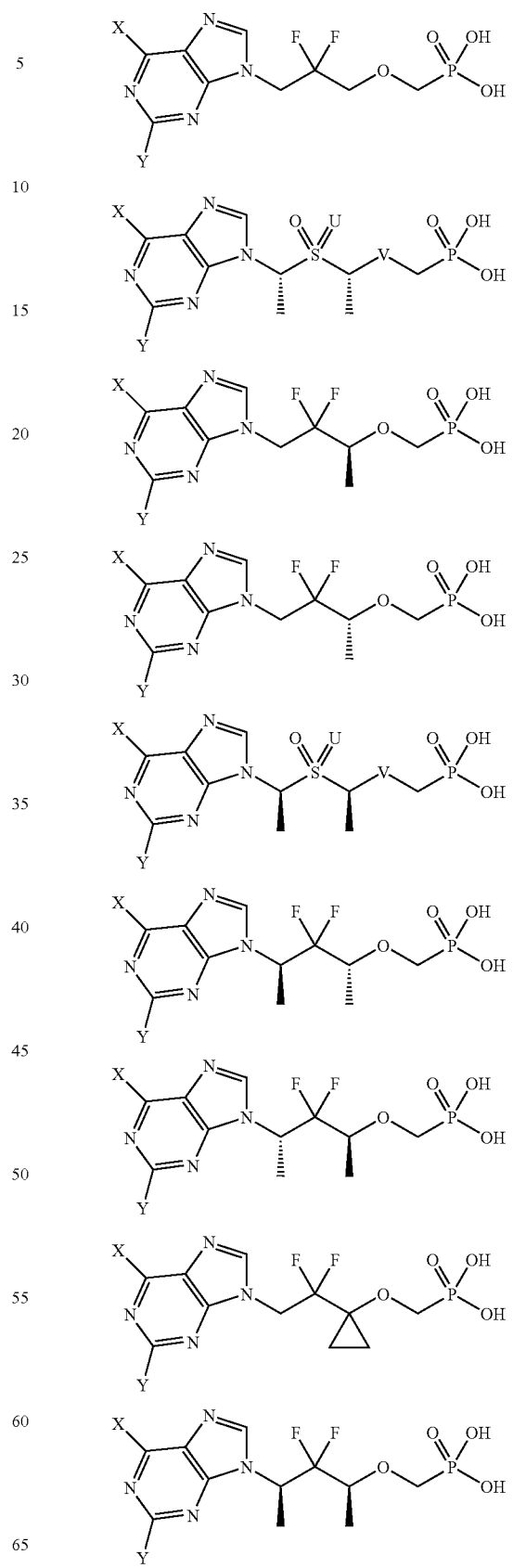

-continued

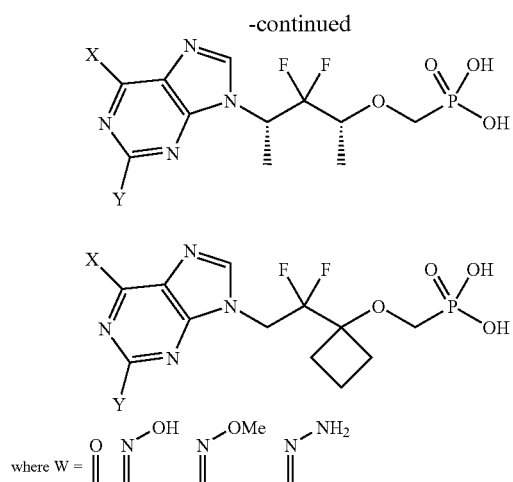

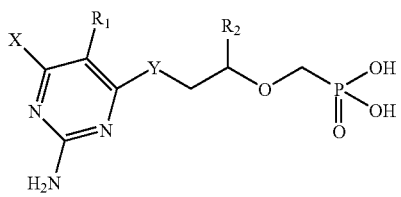

and where X and Y are independently H, Cl, NH$_2$, OH, F, and V=O, NH or NHMe and U=O or Null, W is only O if W and V are adjacent.

The compounds of the invention also include:

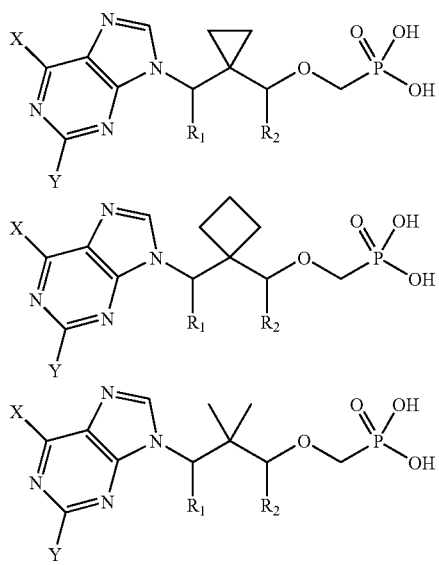

X = OH, OMe, SH, SMe, OCH$_2$CH$_2$CN, OCH$_2$CH$_2$SSMe
Y = O, NH, NMe, S, SO, SO$_2$
R$_1$ = H, Me, CH=CH$_2$, C(triplebond)CH
R$_2$ = H, Me, CH=CH$_2$, F R and S isomers The compounds of the invention also include:

R$_1$ is independently H, Me
R$_2$ is independently H, Me, CH=CH$_2$

Recursive Substituents

Selected substituents within the compounds of the invention are present to a recursive degree. In this context, "recursive substituent" means that a substituent may recite another instance of itself. Because of the recursive nature of such substituents, theoretically, a large number of compounds may be present in any given embodiment. For example, $R^x$ contains a $R^y$ substituent. $R^y$ can be R. One of ordinary skill in the art of medicinal chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

By way of example and not limitation, $W^3$ and $R^y$ are recursive substituents in certain embodiments. Typically, each of these may independently occur 20, 19, 18, 17, 16, 15, 14, 13, 12, 11, 10, 9, 8, 7, 6, 5, 4, 3, 2, 1, or 0, times in a given embodiment. More typically, each of these may independently occur 12 or fewer times in a given embodiment. More typically yet, $W^3$ will occur 0 to 8 times, $R^y$ will occur 0 to 6 times in a given embodiment. Even more typically, $W^3$ will occur 0 to 6 times, $R^y$ will occur 0 to 4 times and $R^3$ will occur 0 to 8 times in a given embodiment.

Recursive substituents are an intended aspect of the invention. One of ordinary skill in the art of medicinal chemistry understands the versatility of such substituents. To the degree that recursive substituents are present in an embodiment of the invention, the total number will be determined as set forth above.

Protecting Groups

In the context of the present invention, embodiments of protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PRT" will be dependent upon the chemistry of the reaction to be protected against (e.g., acidic, basic, oxidative, reductive or other conditions) and the intended direction of the synthesis. The PRT groups do not need to be, and generally are not, the same if the compound is substituted with multiple PRT. In general, PRT will be used to protect functional groups such as carboxyl, hydroxyl or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protection. For example, protecting groups for —OH groups (whether hydroxyl, carboxylic acid, phosphonic acid, or other functions) are embodiments of "ether- or ester-forming groups". Ether- or ester-forming groups are capable of functioning as chemical protecting groups in the synthetic schemes set forth herein. However, some hydroxyl and thio protecting groups are neither ether-nor ester-forming groups, as will be understood by those skilled in the art, and are included with amides, discussed below.

A very large number of hydroxylprotecting groups and amide-forming groups and corresponding chemical cleavage reactions are described in "Protective Groups in Organic Chemistry", Theodora W. Greene (John Wiley & Sons, Inc., New York, 1991, ISBN 0-471-62301-6) ("Greene"). See also Kocienski, Philip J.; "Protecting Groups" (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

The phosphonate moieties of the compounds of the invention may or may not be prodrug moieties, i.e. they may or may not be susceptible to hydrolytic or enzymatic cleavage or modification. Certain phosphonate moieties are stable under most or nearly all metabolic conditions. For example, a dialkylphosphonate, where the alkyl groups are two or more carbons, may have appreciable stability in vivo due to a slow rate of hydrolysis.

Within the context of phosphonate prodrug moieties, a large number of structurally-diverse prodrugs have been described for phosphonic acids (Freeman and Ross in *Progress in Medicinal Chemistry* 34: 112-147 (1997) and are included within the scope of the present invention. An exemplary embodiment of a phosphonate ester-forming group is the phenyl carbocycle in a substructure having the formula:

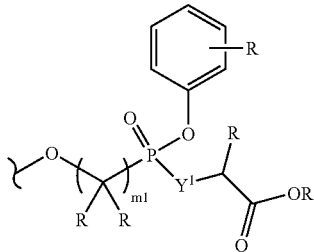

wherein m1 is 1, 2, 3, 4, 5, 6, 7 or 8, and the phenyl carbocycle is substituted with 0 to 3 R groups. Also, in this embodiment, where $Y^1$ is O, a lactate ester is formed. Alternatively, where $Y^1$ is NR, N—OR or N—N(R)$_2$, then phosphonamidate esters result. R may be H or $C_1$-$C_{12}$ alkyl.

In its ester-forming role, a protecting group typically is bound to any acidic group such as, by way of example and not limitation, a —CO$_2$H or —C(S)OH group, thereby resulting in —CO$_2$R$^x$ where R$^x$ is defined herein. Also, R$^x$ for example includes the enumerated ester groups of WO 95/07920.

Examples of protecting groups include:

$C_3$-$C_{12}$ heterocycle (described above) or aryl. These aromatic groups optionally are polycyclic or monocyclic. Examples include phenyl, spiryl, 2- and 3-pyrrolyl, 2- and 3-thienyl, 2- and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 1-, 2-, 3- and 4-pyridinyl, and 1-, 2-, 4- and 5-pyrimidinyl, $C_3$-$C_{12}$ heterocycle or aryl substituted with halo, $R^1$, $R^1$—O—$C_1$-$C_{12}$ alkylene, $C_1$-$C_{12}$ alkoxy, CN, NO$_2$, OH, carboxy, carboxyester, thiol, thioester, $C_1$-$C_{12}$ haloalkyl (1-6 halogen atoms), $C_2$-$C_{12}$ alkenyl or $C_2$-$C_{12}$ alkynyl. Such groups include 2-, 3- and 4-alkoxyphenyl ($C_1$-$C_{12}$ alkyl), 2-, 3- and 4-methoxyphenyl, 2-, 3- and 4-ethoxyphenyl, 2,3-, 2,4-, 2,5-, 2,6-, 3,4- and 3,5-diethoxyphenyl, 2- and 3-carboethoxy-4-hydroxyphenyl, 2- and 3-ethoxy-4-hydroxyphenyl, 2- and 3-ethoxy-5-hydroxyphenyl, 2- and 3-ethoxy-6-hydroxyphenyl, 2-, 3- and 4-O-acetylphenyl, 2-, 3- and 4-dimethylaminophenyl, 2-, 3- and 4-methylmercaptophenyl, 2-, 3- and 4-halophenyl (including 2-, 3- and 4-fluorophenyl and 2-, 3- and 4-chlorophenyl), 2,3-, 2,4-, 2,5-, 2,6-, 3,4- and 3,5-dimethylphenyl, 2,3-, 2,4-, 2,5-, 2,6-, 3,4- and 3,5-biscarboxyethylphenyl, 2,3-, 2,4-, 2,5-, 2,6-, 3,4- and 3,5-dimethoxyphenyl, 2,3-, 2,4-, 2,5-, 2,6-, 3,4- and 3,5-dihalophenyl (including 2,4-difluorophenyl and 3,5-difluorophenyl), 2-, 3- and 4-haloalkylphenyl (1 to 5 halogen atoms, $C_1$-$C_{12}$ alkyl including 4-trifluoromethylphenyl), 2-, 3- and 4-cyanophenyl, 2-, 3- and 4-nitrophenyl, 2-, 3- and 4-haloalkylbenzyl (1 to 5 halogen atoms, $C_1$-$C_{12}$ alkyl including 4-trifluoromethylbenzyl and 2-, 3- and 4-trichloromethylphenyl and 2-, 3- and 4-trichloromethylphenyl), 4-N-methylpiperidinyl, 3-N-methylpiperidinyl, 1-ethylpiperazinyl, benzyl, alkylsalicylphenyl ($C_1$-$C_4$ alkyl, including 2-, 3- and 4-ethylsalicylphenyl), 2-,3- and 4-acetylphenyl, 1,8-dihydroxynaphthyl (—$C_{10}H_6$—OH) and aryloxy ethyl [$C_6$-$C_9$ aryl (including phenoxy ethyl)], 2,2'-dihydroxybiphenyl, 2-, 3- and 4-N, N-dialkylaminophenol, —$C_6H_4CH_2$—N(CH$_3$)$_2$, trimethoxybenzyl, triethoxybenzyl, 2-alkyl pyridinyl ($C_{1-4}$ alkyl);

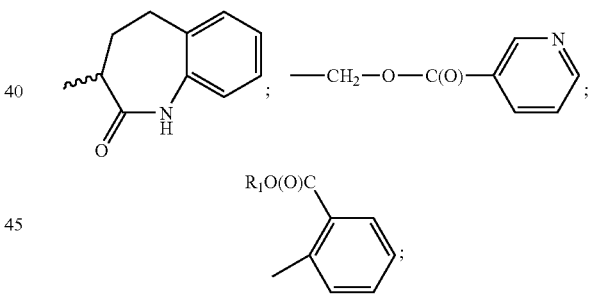

$C_4$-$C_8$ esters of 2-carboxyphenyl; and $C_1$-$C_4$ alkylene-$C_3$-$C_6$ aryl (including benzyl, —CH$_2$-pyrrolyl, —CH$_2$-thienyl, —CH$_2$-imidazolyl, —CH$_2$-oxazolyl, —CH$_2$-isoxazolyl, —CH$_2$-thiazolyl, —CH$_2$-isothiazolyl, —CH$_2$-pyrazolyl, —CH$_2$-pyridinyl and —CH$_2$-pyrimidinyl) substituted in the aryl moiety by 3 to 5 halogen atoms or 1 to 2 atoms or groups selected from halogen, $C_1$-$C_{12}$ alkoxy (including methoxy and ethoxy), cyano, nitro, OH, $C_1$-$C_{12}$ haloalkyl (1 to 6 halogen atoms; including —CH$_2$CCl$_3$), $C_1$-$C_{12}$ alkyl (including methyl and ethyl), $C_2$-$C_{12}$ alkenyl or $C_2$-$C_{12}$ alkynyl; alkoxy ethyl [$C_1$-$C_6$ alkyl including —CH$_2$—CH$_2$—O—CH$_3$ (methoxy ethyl)]; alkyl substituted by any of the groups set forth above for aryl, in particular OH or by 1 to 3 halo atoms (including —CH$_3$, —CH(CH$_3$)$_2$, —C(CH$_3$)$_3$, —CH$_2$CH$_3$, —(CH$_2$)$_2$CH$_3$, —(CH$_2$)$_3$CH$_3$, —(CH$_2$)$_4$CH$_3$, —(CH$_2$)$_5$CH$_3$, CH$_2$CH$_2$F, —CH$_2$CH$_2$Cl, —CH$_2$CF$_3$, and —CH$_2$CCl$_3$);

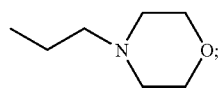

—N-2-propylmorpholino, 2,3-dihydro-6-hydroxyindene, sesamol, catechol monoester, —CH$_2$—C(O)—N(R$^1$)$_2$, —CH$_2$—S(O)(R$^1$), —CH$_2$—S(O)$_2$(R$^1$), —CH$_2$—CH(OC(O)CH$_2$R$^1$)—CH$_2$(OC(O)CH$_2$R$^1$), cholesteryl, enolpyruvate (HOOC—C(=CH$_2$)—), glycerol;

a 5 or 6 carbon monosaccharide, disaccharide or oligosaccharide (3 to 9 monosaccharide residues);

triglycerides such as α-D-β-diglycerides (wherein the fatty acids composing glyceride lipids generally are naturally occurring saturated or unsaturated C$_{6-26}$, C$_{6-8}$ or C$_{6-10}$ fatty acids such as linoleic, lauric, myristic, palmitic, stearic, oleic, palmitoleic, linolenic and the like fatty acids) linked to acyl of the parental compounds herein through a glyceryl oxygen of the triglyceride;

phospholipids linked to the carboxyl group through the phosphate of the phospholipid;

phthalidyl (shown in FIG. 1 of Clayton et al., *Antimicrob. Agents Chemo.* (1974) 5(6):670-671;

cyclic carbonates such as (5-R$_d$-2-oxo-1,3-dioxolen-4-yl) methyl esters (Sakamoto et al., *Chem. Pharm. Bull.* (1984) 32(6)2241-2248) where R$_d$ is R$_1$, R$_4$ or aryl; and

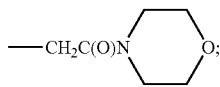

The hydroxyl groups of the compounds of this invention optionally are substituted with one of groups III, IV or V disclosed in WO 94/21604, or with isopropyl.

As further embodiments, Table A lists examples of protecting group ester moieties that for example can be bonded via oxygen to —C(O)O— and —P(O)(O—)$_2$ groups. Several amidates also are shown, which are bound directly to —C(O)— or —P(O)$_2$. Esters of structures 1-5,8-10 and 16, 17, 19-22 are synthesized by reacting the compound herein having a free hydroxyl with the corresponding halide (chloride or acyl chloride and the like) and N,N-dicyclohexyl-N-morpholine carboxamidine (or another base such as DBU, triethylamine, CsCO$_3$, N,N-dimethylaniline and the like) in DMF (or other solvent such as acetonitrile or N-methylpyrrolidone). When the compound to be protected is a phosphonate, the esters of structures 5-7, 11, 12, 21, and 23-26 are synthesized by reaction of the alcohol or alkoxide salt (or the corresponding amines in the case of compounds such as 13, 14 and 15) with the monochlorophosphonate or dichlorophosphonate (or another activated phosphonate).

TABLE A

| 1. | —CH$_2$—C(O)—N(R$_1$)$_2$* |
| 2. | —CH$_2$—S(O)(R$_1$) |
| 3. | —CH$_2$—S(O)$_2$(R$_1$) |
| 4. | —CH$_2$—O—C(O)—CH$_2$—C$_6$H$_5$ |
| 5. | 3-cholesteryl |
| 6. | 3-pyridyl |
| 7. | N-ethylmorpholino |
| 8. | —CH$_2$—O—C(O)—C$_6$H$_5$ |
| 9. | —CH$_2$—O—C(O)—CH$_2$CH$_3$ |
| 10. | —CH$_2$—O—C(O)—C(CH$_3$)$_3$ |

TABLE A-continued

| 11. | —CH$_2$—CCl$_3$ |
| 12. | —C$_6$H$_5$ |
| 13. | —NH—CH$_2$—C(O)O—CH$_2$CH$_3$ |
| 14. | —N(CH$_3$)—CH$_2$—C(O)O—CH$_2$CH$_3$ |
| 15. | —NHR$_1$ |
| 16. | —CH$_2$—O—C(O)—C$_{10}$H$_{15}$ |
| 17. | —CH$_2$—O—C(O)—CH(CH$_3$)$_2$ |
| 18. | —CH$_2$—C#H(OC(O)CH$_2$R$_1$)—CH$_2$—(OC(O)CH$_2$R$_1$)* |
| 19. |  |
| 20. | 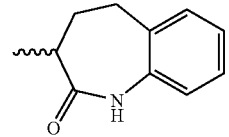 |
| 21. | 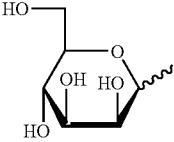 |
| 22. | 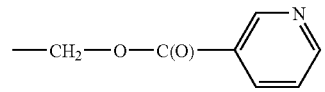 |
| 23. | 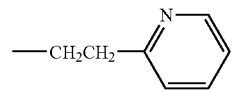 |
| 24. | 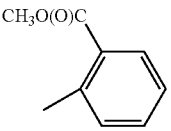 |
| 25. | 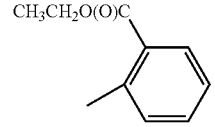 |
| 26. | 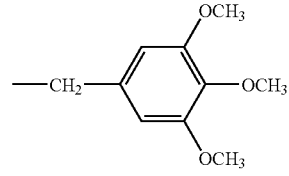 |

—chiral center is (R), (S) or racemate.

Other esters that are suitable for use herein are described in EP 632048.

Protecting groups also includes "double ester" forming profunctionalities such as —CH$_2$OC(O)OCH$_3$,

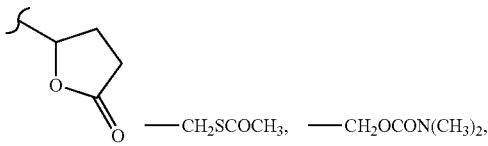, —CH$_2$SCOCH$_3$, —CH$_2$OCON(CH$_3$)$_2$, or alkyl- or aryl-acyloxyalkyl groups of the structure —CH (R$^1$ or W$^5$)O((CO)R$^{37}$) or —CH(R$^1$ or W$^5$)((CO)OR$^{38}$) (linked to oxygen of the acidic group) wherein R$^{37}$ and R$^{38}$ are alkyl, aryl, or alkylaryl groups (see U.S. Pat. No. 4,968, 788). Frequently R$^{37}$ and R$^{38}$ are bulky groups such as branched alkyl, ortho-substituted aryl, meta-substituted aryl, or combinations thereof, including normal, secondary, iso- and tertiary alkyls of 1-6 carbon atoms. An example is the pivaloyloxymethyl group. These are of particular use with prodrugs for oral administration. Examples of such useful protecting groups are alkylacyloxymethyl esters and their derivatives, including —

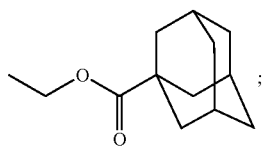

—CH$_2$OC(O)C$_{10}$OH$_{15}$, —CH$_2$OC(O)C(CH$_3$)$_3$, —CH(CH$_2$OCH$_3$)OC(O)C(CH$_3$)$_3$, —CH(CH(CH$_3$)$_2$)OC(O)C(CH$_3$)$_3$, —CH$_2$OC(O)CH$_2$CH(CH$_3$)$_2$, —CH$_2$OC(O)C$_6$H$_{11}$, —CH$_2$OC(O)C$_6$H$_5$, —CH$_2$OC(O)C$_{10}$H$_{15}$, —CH$_2$OC(O)CH$_2$CH$_3$, —CH$_2$OC(O)CH(CH$_3$)$_2$, —CH$_2$OC(O)C(CH$_3$)$_3$ and —CH$_2$OC(O)CH$_2$C$_6$H$_5$.

For prodrug purposes, the ester typically chosen is one heretofore used for antibiotic drugs, in particular the cyclic carbonates, double esters, or the phthalidyl, aryl or alkyl esters.

In some embodiments the protected acidic group is an ester of the acidic group and is the residue of a hydroxyl-containing functionality. In other embodiments, an amino compound is used to protect the acid functionality. The residues of suitable hydroxyl or amino-containing functionalities are set forth above or are found in WO 95/07920. Of particular interest are the residues of amino acids, amino acid esters, polypeptides, or aryl alcohols. Typical amino acid, polypeptide and carboxyl-esterified amino acid residues are described on pages 11-18 and related text of WO 95/07920 as groups L1 or L2. WO 95/07920 expressly teaches the amidates of phosphonic acids, but it will be understood that such amidates are formed with any of the acid groups set forth herein and the amino acid residues set forth in WO 95/07920.

Typical esters for protecting acidic functionalities are also described in WO 95/07920, again understanding that the same esters can be formed with the acidic groups herein as with the phosphonate of the '920 publication. Typical ester groups are defined at least on WO 95/07920 pages 89-93 (under R$^{31}$ or R$^{35}$), the table on page 105, and pages 21-23 (as R). Of particular interest are esters of unsubstituted aryl such as phenyl or arylalkyl such benzyl, or hydroxy-, halo-, alkoxy-, carboxy- and/or alkylestercarboxy-substituted aryl or alkylaryl, especially phenyl, ortho-ethoxyphenyl, or C$_1$-C$_4$ alkylestercarboxyphenyl (salicylate C I—C$_{1-2}$ alkylesters).

The protected acidic groups, particularly when using the esters or amides of WO 95/07920, are useful as prodrugs for oral administration. However, it is not essential that the acidic group be protected in order for the compounds of this invention to be effectively administered by the oral route. When the compounds of the invention having protected groups, in particular amino acid amidates or substituted and unsubstituted aryl esters are administered systemically or orally they are capable of hydrolytic cleavage in vivo to yield the free acid.

One or more of the acidic hydroxyls are protected. If more than one acidic hydroxyl is protected then the same or a different protecting group is employed, e.g., the esters may be different or the same, or a mixed amidate and ester may be used.

Typical hydroxy protecting groups described in Greene (pages 14-118) include substituted methyl and alkyl ethers, substituted benzyl ethers, silyl ethers, esters including sulfonic acid esters, and carbonates. For example:

Ethers (methyl, t-butyl, allyl);
Substituted Methyl Ethers (Methoxymethyl, Methylthiomethyl, t-Butylthiomethyl, (Phenyldimethylsilyl)methoxymethyl, Benzyloxymethyl, p-Methoxybenzyloxymethyl, (4-Methoxyphenoxy)methyl, Guaiacolmethyl, t-Butoxymethyl, 4-Pentenyloxymethyl, Siloxymethyl, 2-Methoxyethoxymethyl, 2,2,2-Trichloroethoxymethyl, Bis(2-chloroethoxy)methyl, 2-(Trimethylsilyl)ethoxymethyl, Tetrahydropyranyl, 3-Bromotetrahydropyranyl, Tetrahydropthiopyranyl, 1-Methoxycyclohexyl, 4-Methoxytetrahydropyranyl, 4-Methoxytetrahydrothiopyranyl, 4-Methoxytetrahydropthiopyranyl S,S-Dioxido, 1-[(2-Chloro-4-methyl)phenyl]-4-methoxypiperidin-4-yl, 1,4-Dioxan-2-yl, Tetrahydrofuranyl, Tetrahydrothiofuranyl, 2,3,3a,4,5,6,7,7a-Octahydro-7,8,8-trimethyl-4,7-methanobenzofuran-2-yl));
Substituted Ethyl Ethers (1-Ethoxyethyl, 1-(2-Chloroethoxy)ethyl, 1-Methyl-1-methoxyethyl, 1-Methyl-1-benzyloxyethyl, 1-Methyl-1-benzyloxy-2-fluoroethyl, 2,2,2-Trichloroethyl, 2-Trimethylsilylethyl, 2-(Phenylselenyl)ethyl,
p-Chlorophenyl, p-Methoxyphenyl, 2,4-Dinitrophenyl, Benzyl);
Substituted Benzyl Ethers (p-Methoxybenzyl, 3,4-Dimethoxybenzyl, o-Nitrobenzyl, p-Nitrobenzyl, p-Halobenzyl, 2,6-Dichlorobenzyl, p-Cyanobenzyl, p-Phenylbenzyl, 2- and 4-Picolyl, 3-Methyl-2-picolyl N-Oxido, Diphenylmethyl, pp'-Dinitrobenzhydryl, 5-Dibenzosuberyl, Triphenylmethyl, α-Naphthyldiphenylmethyl, p-methoxyphenyldiphenylmethyl, Dipmethoxyphenyl)phenylmethyl, Tri(p-methoxyphenyl)methyl, 4-(4'-Bromophenacyloxy)phenyldiphenylmethyl, 4,4',4"-Tris(4,5-dichlorophthalimidophenyl)methyl, 4,4',4"-Tris(levulinoyloxyphenyl)methyl, 4,4',4"-Tris(benzoyloxyphenyl)methyl, 3-(Imidazol-1-ylmethyl)bis(4',4"-dimethoxyphenyl)methyl, 1,1-Bis(4-methoxyphenyl)-1'-pyrenylmethyl, 9-Anthryl, 9-(9-Phenyl)xanthenyl, 9-(9-Phenyl-10-oxo)anthryl, 1,3-Benzodithiolan-2-yl, Benzisothiazolyl S,S-Dioxido);
Silyl Ethers (Trimethylsilyl, Triethylsilyl, Triisopropylsilyl, Dimethylisopropylsilyl, Diethylisopropylsilyl, Dimethylthexylsilyl, t-Butyldimethylsilyl, t-Butyldiphenylsilyl, Tribenzylsilyl, Tri-p-xylylsilyl, Triphenylsilyl, Diphenylmethylsilyl, t-Butylmethoxyphenylsilyl);
Esters (Formate, Benzoylformate, Acetate, Choroacetate, Dichloroacetate, Trichloroacetate, Trifluoroacetate, Methoxyacetate, Triphenylmethoxyacetate, Phenoxyacetate, p-Chlorophenoxyacetate, p-poly-Phenylacetate, 3-Phenylpropionate, 4-Oxopentanoate (Levulinate), 4,4-(Ethylenedithio)pentanoate, Pivaloate, Adamantoate, Crotonate, 4-Methoxycrotonate, Benzoate, p-Phenylbenzoate, 2,4,6-Trimethylbenzoate (Mesitoate));

Carbonates (Methyl, 9-Fluorenylmethyl, Ethyl, 2,2,2-Trichloroethyl, 2-(Trimethylsilyl)ethyl, 2-(Phenylsulfonyl)ethyl, 2-(Triphenylphosphonio)ethyl, Isobutyl, Vinyl, Allyl, p-Nitrophenyl, Benzyl, p-Methoxybenzyl, 3,4-Dimethoxybenzyl, o-Nitrobenzyl, p-Nitrobenzyl, S-Benzyl Thiocarbonate, 4-Ethoxy-1-naphthyl, Methyl Dithiocarbonate);

Groups With Assisted Cleavage (2-Iodobenzoate, 4-Azidobutyrate, 4-Nitro-4-methylpentanoate, o-(Dibromomethyl)benzoate, 2-Formylbenzenesulfonate, 2-(Methylthiomethoxy)ethyl Carbonate, 4-(Methylthiomethoxy)butyrate, 2-(Methylthiomethoxymethyl)benzoate); Miscellaneous Esters (2,6-Dichloro-4-methylphenoxyacetate, 2,6-Dichloro-4-(1,1,3,3 tetramethylbutyl)phenoxyacetate, 2,4-Bis(1,1-dimethylpropyl)phenoxyacetate, Chlorodiphenylacetate, Isobutyrate, Monosuccinate, (E)-2-Methyl-2-butenoate (Tigloate), o-(Methoxycarbonyl)benzoate, p-poly-Benzoate, α-Naphthoate, Nitrate, Alkyl N,N,N',N'-Tetramethylphosphorodiamidate, N-Phenylcarbamate, Borate, Dimethylphosphinothioyl, 2,4-Dinitrophenylsulfenate); and Sulfonates (Sulfate, Methanesulfonate (Mesylate), Benzylsulfonate, Tosylate).

Typical 1,2-diol protecting groups (thus, generally where two OH groups are taken together with the protecting functionality) are described in Greene at pages 118-142 and include Cyclic Acetals and Ketals (Methylene, Ethylidene, 1-t-Butylethylidene, 1-Phenylethylidene, (4-Methoxyphenyl)ethylidene, 2,2,2-Trichloroethylidene, Acetonide (Isopropylidene), Cyclopentylidene, Cyclohexylidene, Cycloheptylidene, Benzylidene, p-Methoxybenzylidene, 2,4-Dimethoxybenzylidene, 3,4-Dimethoxybenzylidene, 2-Nitrobenzylidene); Cyclic Ortho Esters (Methoxymethylene, Ethoxymethylene, Dimethoxymethylene, 1-Methoxyethylidene, 1-Ethoxyethylidine, 1,2-Dimethoxyethylidene, α-Methoxybenzylidene, 1-(N,N-Dimethylamino)ethylidene Derivative, α-(N,N-Dimethylamino)benzylidene Derivative, 2-Oxacyclopentylidene); Silyl Derivatives (Di-t-butylsilylene Group, 1,3-(1,1,3,3-Tetraisopropyldisiloxanylidene), and Tetra-t-butoxydisiloxane-1,3-diylidene), Cyclic Carbonates, Cyclic Boronates, Ethyl Boronate and Phenyl Boronate.

More typically, 1,2-diol protecting groups include those shown in Table B, still more typically, epoxides, acetonides, cyclic ketals and aryl acetals.

TABLE B

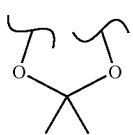

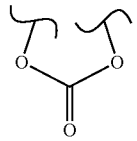

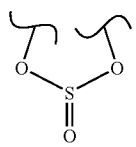

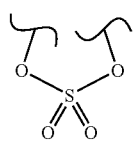

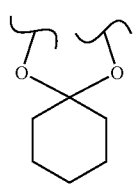

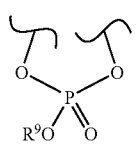

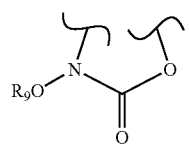

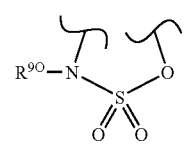

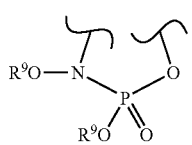

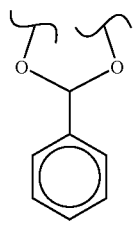

wherein $R^9$ is $C_1$-$C_6$ alkyl.

Amino Protecting Groups

Another set of protecting groups include any of the typical amino protecting groups described by Greene at pages 315-385. They include:

Carbamates: (methyl and ethyl, 9-fluorenylmethyl, 9(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, 4-methoxyphenacyl);

Substituted Ethyl: (2,2,2-trichoroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl, diphenylmethyl);

Groups With Assisted Cleavage: (2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-choro-p-acyloxybenzyl, p-(dihydroxyboryl)benzyl, 5-benzisoxazolylmethyl, 2-(trifluoromethyl)-6-chromonylmethyl);

Groups Capable of Photolytic Cleavage: (m-nitrophenyl, 3,5-dimethoxybenzyl, o-nitrobenzyl, 3,4-dimethoxy-6-nitrobenzyl, phenyl(o-nitrophenyl)methyl); Urea-Type Derivatives (phenothiazinyl-(10)-carbonyl, N'-p-toluenesulfonylaminocarbonyl, N'-phenylaminothiocarbonyl);

Miscellaneous Carbamates: (t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl)methyl, 2-furanylmethyl, 2-Iodoethyl, Isobornyl, Isobutyl, Isonicotinyl, p-(p-Methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, 2,4,6-trimethylbenzyl);

Amides: (N-formyl, N-acetyl, N-choroacetyl, N-trichoroacetyl, N-trifluoroacetyl, N-phenylacetyl, N-3-phenylpropionyl, N-picolinoyl, N-3-pyridylcarboxamide, N-benzoylphenylalanyl, N-benzoyl, N-p-phenylbenzoyl);

Amides With Assisted Cleavage: (N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine, N-o-nitrobenzoyl, N-o-(benzoyloxymethyl)benzoyl, 4,5-diphenyl-3-oxazolin-2-one);

Cyclic Imide Derivatives: (N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridonyl);

N-Alkyl and N-Aryl Amines: (N-methyl, N-allyl, N-[2-(trimethylsilyl)ethoxy]methyl, N-3-acetoxypropyl, N-(1-isopropyl-4-nitro-2-oxo-3-pyrrolin-3-yl), Quaternary Ammonium Salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, N-2-picolylamine N'-oxide);

Imine Derivatives: (N-1,1-dimethylthiomethylene, N-benzylidene, N-p-methoxybenylidene, N-diphenylmethylene, N-[(2-pyridyl)mesityl]methylene, N,(N',N'-dimethylaminomethylene, N,N'-isopropylidene, N-p-nitrobenzylidene, N-salicylidene, N-5-chlorosalicylidene, N-(5-chloro-2-hydroxyphenyl)phenylmethylene, N-cyclohexylidene);

Enamine Derivatives: (NT-(5,5-dimethyl-3-oxo-1-cyclohexenyl));

N-Metal Derivatives (N-borane derivatives, N-diphenylborinic acid derivatives, N-[phenyl(pentacarbonylchromium- or -tungsten)]carbenyl, N-copper or N-zinc chelate);

N—N Derivatives: (N-nitro, N-nitroso, N-oxide);

N—P Derivatives: (N-diphenylphosphinyl, N-dimethylthiophosphinyl, N-diphenylthiophosphinyl, N-dialkyl phosphoryl, N-dibenzyl phosphoryl, N-diphenyl phosphoryl);

N-Si Derivatives, N—S Derivatives, and N-Sulfenyl Derivatives: (N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl, N-triphenylmethylsulfenyl, N-3-nitropyridinesulfenyl); and N-sulfonyl Derivatives (N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6,-tetramethyl-4-methoxybenzenesulfonyl, N-4-methoxybenzenesulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N-β-trimethylsilyethanesulfonyl, N-9-anthracenesulfonyl, N-4-(4',8'-dimethoxynaphthylmethyl)benzenesulfonyl, N-benzylsulfonyl, N-trifluoromethylsulfonyl, N-phenacylsulfonyl).

Protected amino groups include carbamates, amides and amidines, e.g. —NHC(O)OR$^1$, —NHC(O)R$^1$ or —N=CR$^1$N(R$^1$)$_2$. Another protecting group, also useful as a prodrug for amino or —NH(R$^5$), is:

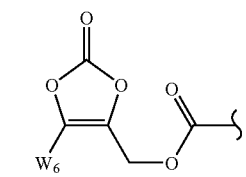

See for example Alexander, J. et al (1996) *J. Med. Chem.* 39:480-486.

Amino Acid and Polypeptide Protecting Group and Conjugates

An amino acid or polypeptide protecting group of a compound of the invention has the structure R$^{15}$NHCH(R$^{16}$)C(O)—, where R$^{15}$ is H, an amino acid or polypeptide residue, or R$^5$, and R$^{16}$ is defined below.

$R^{16}$ is lower alkyl or lower alkyl ($C_1$-$C_6$) substituted with amino, carboxyl, amide, carboxyl ester, hydroxyl, $C_6$-$C_7$ aryl, guanidinyl, imidazolyl, indolyl, sulfhydryl, sulfoxide, and/or alkylphosphate. $R^{16}$ also is taken together with the amino acid α-N to form a proline residue ($R^{16}$=—$CH_2)_3$—). However, $R^{16}$ is generally the side group of a naturally-occurring amino acid such as H, —$CH_3$, —$CH(CH_3)_2$, —$CH_2$—$CH(CH_3)_2$, —$CHCH_3$—$CH_2$—$CH_3$, —$CH_2$—$C_6H_5$, —$CH_2CH_2$—S—$CH_3$, —$CH_2OH$, —$CH(OH)$—$CH_3$, —$CH_2$—SH, —$CH_2$—$C_6H_4OH$, —$CH_2$—CO—$NH_2$, —$CH_2$—$CH_2$—CO—$NH_2$, —$CH_2$—COOH, —$CH_2$—$CH_2$—COOH, —$(CH_2)_4$—$NH_2$ and —$(CH_2)_3$—NH—$C(NH_2)$—$NH_2$. $R^{16}$ also includes 1-guanidinoprop-3-yl, benzyl, 4-hydroxybenzyl, imidazol-4-yl, indol-3-yl, methoxyphenyl and ethoxyphenyl.

Another set of protecting groups include the residue of an amino-containing compound, in particular an amino acid, a polypeptide, a protecting group, —$NHSO_2R$, NHC(O)R, —$N(R)_2$, $NH_2$ or —NH(R)(H), whereby for example a carboxylic acid is reacted, i.e. coupled, with the amine to form an amide, as in $C(O)NR_2$. A phosphonic acid may be reacted with the amine to form a phosphonamidate, as in —P(O)(OR)($NR_2$).

Amino acids have the structure $R^{17}C(O)CH(R^{16})NH$—, where $R^{17}$ is —OH, —OR, an amino acid or a polypeptide residue. Amino acids are low molecular weight compounds, on the order of less than about 1000 MW and which contain at least one amino or imino group and at least one carboxyl group. Generally the amino acids will be found in nature, i.e., can be detected in biological material such as bacteria or other microbes, plants, animals or man. Suitable amino acids typically are alpha amino acids, i.e. compounds characterized by one amino or imino nitrogen atom separated from the carbon atom of one carboxyl group by a single substituted or unsubstituted alpha carbon atom. Of particular interest are hydrophobic residues such as mono- or di-alkyl or aryl amino acids, cycloalkylamino acids and the like. These residues contribute to cell permeability by increasing the partition coefficient of the parental drug. Typically, the residue does not contain a sulfhydryl or guanidino substituent.

Naturally-occurring amino acid residues are those residues found naturally in plants, animals or microbes, especially proteins thereof. Polypeptides most typically will be substantially composed of such naturally-occurring amino acid residues. These amino acids are glycine, alanine, valine, leucine, isoleucine, serine, threonine, cysteine, methionine, glutamic acid, aspartic acid, lysine, hydroxylysine, arginine, histidine, phenylalanine, tyrosine, tryptophan, proline, asparagine, glutamine and hydroxyproline. Additionally, unnatural amino acids, for example, valanine, phenylglycine and homoarginine are also included. Commonly encountered amino acids that are not gene-encoded may also be used in the present invention. All of the amino acids used in the present invention may be either the D- or L-optical isomer. In addition, other peptidomimetics are also useful in the present invention. For a general review, see Spatola, A. F., in *Chemistry and Biochemistry of Amino Acids, Peptides and Proteins*, B. Weinstein, eds., Marcel Dekker, New York, p. 267 (1983).

When protecting groups are single amino acid residues or polypeptides they optionally are substituted with substituents. These conjugates are generally produced by forming an amide bond between a carboxyl group of the amino acid (or C-terminal amino acid of a polypeptide for example). Generally, only one of any site in the scaffold drug-like compound is amidated with an amino acid as described herein, although it is within the scope of this invention to introduce amino acids at more than one permitted site. Usually, a carboxyl group of $R^3$ is amidated with an amino acid. In general, the α-amino or α-carboxyl group of the amino acid or the terminal amino or carboxyl group of a polypeptide are bonded to the scaffold, parental functionalities. Carboxyl or amino groups in the amino acid side chains generally may be used to form the amide bonds with the parental compound or these groups may need to be protected during synthesis of the conjugates as described further below.

With respect to the carboxyl-containing side chains of amino acids or polypeptides it will be understood that the carboxyl group optionally will be blocked, e.g. esterified or amidated with R.

Such ester or amide bonds with side chain amino or carboxyl groups, like the esters or amides with the parental molecule, optionally are hydrolyzable in vivo or in vitro under acidic (pH<3) or basic (pH>10) conditions. Alternatively, they are substantially stable in the gastrointestinal tract of humans but are hydrolyzed enzymatically in blood or in intracellular environments. The esters or amino acid or polypeptide amidates also are useful as intermediates for the preparation of the parental molecule containing free amino or carboxyl groups. The free acid or base of the parental compound, for example, is readily formed from the esters or amino acid or polypeptide conjugates of this invention by conventional hydrolysis procedures.

When an amino acid residue contains one or more chiral centers, any of the D, L, meso, threo or erythro (as appropriate) racemates, scalemates or mixtures thereof may be used. In general, if the intermediates are to be hydrolyzed non-enzymatically (as would be the case where the amides are used as chemical intermediates for the free acids or free amines), D isomers are useful. On the other hand, L isomers are more versatile since they can be susceptible to both non-enzymatic and enzymatic hydrolysis, and are more efficiently transported by amino acid or dipeptidyl transport systems in the gastrointestinal tract.

Examples of suitable amino acids whose residues are represented by $R^x$ or $R^y$ include the following:

Glycine;

Aminopolycarboxylic acids, e.g., aspartic acid, β-hydroxyaspartic acid, glutamic acid, β-hydroxyglutamic acid, β-methylaspartic acid, β-methylglutamic acid, β, β-dimethylaspartic acid, γ-hydroxyglutamic acid, β, γ-dihydroxyglutamic acid, β-phenylglutamic acid, γ-methyleneglutamic acid, 3-aminoadipic acid, 2-aminopimelic acid, 2-aminosuberic acid and 2-aminosebacic acid;

Amino acid amides such as glutamine and asparagine;

Polyamino- or polybasic-monocarboxylic acids such as arginine, lysine, β-aminoalanine, γ-aminobutyrine, ormithine, citruline, homoarginine, homocitrulline, hydroxylysine, allohydroxylsine and diaminobutyric acid;

Other basic amino acid residues such as histidine;

Diaminodicarboxylic acids such as α, α'-diaminosuccinic acid, α, α'-diaminoglutaric acid, α, α'-diaminoadipic acid, α, α'-diaminopimelic acid, α, α'-diamino-β-hydroxypimelic acid, α, α'-diaminosuberic acid, α, α'-diaminoazelaic acid, and α, α'-diaminosebacic acid;

Imino acids such as proline, hydroxyproline, allohydroxyproline, γ-methylproline, pipecolic acid, 5-hydroxypipecolic acid, and azetidine-2-carboxylic acid;

A mono- or di-alkyl (typically $C_1$-$C_8$ branched or normal) amino acid such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ε-hydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, α-aminodiisoamyacetic acid, α-methylaspartic acid, α-methylglutamic acid, 1-aminocyclopropane-1-carboxylic acid, isoleucine, alloisoleucine, tert-leucine, β-methyltryptophan and α-amino-β-ethyl-β-phenylpropionic acid;

β-phenylserinyl;

Aliphatic α-amino-β-hydroxy acids such as serine, β-hydroxyleucine, β-hydroxynorleucine, β-hydroxynorvaline, and α-amino-β-hydroxystearic acid;

α-Amino, α-, γ-, δ- or ε-hydroxy acids such as homoserine, 6-hydroxynorvaline, γ-hydroxynorvaline and F-hydroxynorleucine residues; canavine and canaline; γ-hydroxyornithine;

2-hexosaminic acids such as D-glucosaminic acid or D-galactosaminic acid;

α-Amino-β-thiols such as penicillamine, '-thiolnorvaline or '3-thiolbutyrine;

Other sulfur containing amino acid residues including cysteine; homocystine, β-phenylmethionine, methionine, S-allyl-L-cysteine sulfoxide, 2-thiolhistidine, cystathionine, and thiol ethers of cysteine or homocysteine;

Phenylalanine, tryptophan and ring-substituted α-amino acids such as the phenyl- or cyclohexylamino acids α-aminophenylacetic acid, α-aminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-, 3,4-dichloro, o-, m- or p-methyl-, 2,4,6-trimethyl-, 2-ethoxy-5-nitro-, 2-hydroxy-5-nitro- and p-nitro-phenylalanine); furyl-, thienyl-, pyridyl-, pyrimidinyl-, purinyl- or naphthyl-alanines; and tryptophan analogues and derivatives including kynurenine, 3-hydroxykyriurenine, 2-hydroxytryptophan and 4-carboxytryptophan;

α-Amino substituted amino acids including sarcosine (N-methylglycine), N-benzylglycine, N-methylalanine, N-benzylalanine, N-methylphenylalanine, N-benzylphenylalanine, N-methylvaline and N-benzylvaline; and α-Hydroxy and substituted α-hydroxy amino acids including serine, threonine, allothreonine, phosphoserine and phosphothreonine.

Polypeptides are polymers of amino acids in which a carboxyl group of one amino acid monomer is bonded to an amino or imino group of the next amino acid monomer by an amide bond. Polypeptides include dipeptides, low molecular weight polypeptides (about 1500-5000 MW) and proteins. Proteins optionally contain 3, 5, 10, 50, 75, 100 or more residues, and suitably are substantially sequence-homologous with human, animal, plant or microbial proteins. They include enzymes (e.g., hydrogen peroxidase) as well as immunogens such as KLH, or antibodies or proteins of any type against which one wishes to raise an immune response. The nature and identity of the polypeptide may vary widely.

The polypeptide amidates are useful as immunogens in raising antibodies against either the polypeptide (if it is not immunogenic in the animal to which it is administered) or against the epitopes on the remainder of the compound of this invention.

Antibodies capable of binding to the parental non-peptidyl compound are used to separate the parental compound from mixtures, for example in diagnosis or manufacturing of the parental compound. The conjugates of parental compound and polypeptide generally are more immunogenic than the polypeptides in closely homologous animals, and therefore make the polypeptide more immunogenic for facilitating raising antibodies against it. Accordingly, the polypeptide or protein may be immunogenic in an animal typically used to raise antibodies, e.g., rabbit, mouse, horse, or rat. The polypeptide optionally contains a peptidolytic enzyme cleavage site at the peptide bond between the first and second residues adjacent to the acidic heteroatom. Such cleavage sites are flanked by enzymatic recognition structures, e.g. a particular sequence of residues recognized by a peptidolytic enzyme.

Peptidolytic enzymes for cleaving the polypeptide conjugates of this invention are well known, and in particular include carboxypeptidases, which digest polypeptides by removing C-terminal residues, and are specific in many instances for particular C-terminal sequences. Such enzymes and their substrate requirements in general are well known. For example, a dipeptide (having a given pair of residues and a free carboxyl terminus) is covalently bonded through its α-amino group to the phosphorus or carbon atoms of the compounds herein. In certain embodiments, a phosphonate group substituted with an amino acid or peptide will be cleaved by the appropriate peptidolytic enzyme, leaving the carboxyl of the proximal amino acid residue to autocatalytically cleave the phosphonoamidate bond.

Suitable dipeptidyl groups (designated by their single letter code) are AA, AR, AN, AD, AC, AE, AQ, AG, AH, Al, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, EC, EE, EQ, EG, EH, El, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, Fl, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY and VV.

Tripeptide residues are also useful as protecting groups. When a phosphonate is to be protected, the sequence —$X^4$-pro-$X^5$— (where $X^4$ is any amino acid residue and $X^5$ is an amino acid residue, a carboxyl ester of proline, or hydrogen) will be cleaved by luminal carboxypeptidase to yield $X^4$ with a free carboxyl, which in turn is expected to autocatalytically cleave the phosphonoamidate bond. The carboxy group of $X^5$ optionally is esterified with benzyl.

Dipeptide or tripeptide species can be selected on the basis of known transport properties and/or susceptibility to peptidases that can affect transport to intestinal mucosal or other cell types. Dipeptides and tripeptides lacking an α-amino group are transport substrates for the peptide transporter found in brush border membrane of intestinal mucosal cells (Bai, J. P. F., (1992) *Pharm Res.* 9:969-978. Transport competent peptides can thus be used to enhance bioavailability of the amidate compounds. Di- or tripeptides having one or more amino acids in the D configuration may be compatible with peptide transport. Amino acids in the D configuration can be used to reduce the susceptibility of a di- or tripeptide to hydrolysis by proteases common to the brush border such as aminopeptidase N. In addition, di- or tripeptides alternatively are selected on the basis of their relative resistance to hydrolysis by proteases found in the lumen of the intestine. For example, tripeptides or polypeptides lacking asp and/or glu are poor substrates for aminopeptidase A, di- or tripeptides lacking amino acid residues on the N-terminal side of hydrophobic amino acids (leu, tyr, phe, val, trp) are poor substrates for endopeptidase, and peptides lacking a pro residue at the penultimate position at a free carboxyl terminus are poor substrates for carboxypeptidase P. Similar considerations can also be applied to the selection of peptides that are either relatively resistant or relatively susceptible to hydrolysis by cytosolic, renal, hepatic, serum or other peptidases. Such poorly cleaved polypeptide amidates are immunogens or are useful for bonding to proteins in order to prepare immunogens.

Intracellular Targeting

The phosphonate group of Formula I compounds may cleave in vivo in stages after they have reached the desired site of action, i.e. inside a cell. One mechanism of action inside a cell may entail a first cleavage, e.g. by esterase, to provide a negatively-charged "locked in" intermediate. Cleavage of a terminal ester grouping in Formulas I or II compounds thus affords an unstable intermediate which releases a negatively charged "locked in" intermediate.

After passage inside a cell, intracellular enzymatic cleavage or modification of the phosphonate prodrug compound may result in an intracellular accumulation or retention of the cleaved or modified compound by a "trapping" mechanism. The cleaved or modified compound, i.e. active metabolite, may then be "locked-in" the cell, i.e. accumulate in the cell by a significant change in charge, polarity, or other physical property change which decreases the rate at which the cleaved or modified compound can exit the cell, relative to the rate at which it entered as the phosphonate prodrug. Other mechanisms by which a therapeutic effect is achieved may be operative as well. Enzymes which are capable of an enzymatic activation mechanism with the phosphonate prodrug compounds of the invention include, but are not limited to, amidases, esterases, microbial enzymes, phospholipases, cholinesterases, and phosphatases.

It is known that the drug is activated in vivo by phosphorylation. Such activation may occur in the present system by enzymatic conversion of the "locked-in" intermediate with phosphokinase to the active phosphonate diphosphate and/or by phosphorylation of the drug itself after its release from the "locked-in" intermediate as described above. In either case, the original nucleoside-type drug will be converted, via the derivatives of this invention, to the active phosphorylated species.

From the foregoing, it will be apparent that many structurally different known approved and experimental HIV reverse transcriptase inhibitor drugs can be derivatized in accord with the present invention. Numerous such drugs are specifically mentioned herein. However, it should be understood that the discussion of drug families and their specific members for derivatization according to this invention is not intended to be exhaustive, but merely illustrative.

As another example, when the selected drug contains multiple reactive hydroxyl functions, a mixture of intermediates and final products may again be obtained. In the unusual case in which all hydroxy groups are approximately equally reactive, there is not expected to be a single, predominant product, as each mono-substituted product will be obtained in approximate by equal amounts, while a lesser amount of multiply-substituted product will also result. Generally speaking, however, one of the hydroxyl groups will be more susceptible to substitution than the other(s), e.g. a primary hydroxyl will be more reactive than a secondary hydroxyl, an unhindered hydroxyl will be more reactive than a hindered one. Consequently, the major product will be a mono-substituted one in which the most reactive hydroxyl has been derivatized while other mono-substituted and multiply-substituted products may be obtained as minor products.

Stereoisomers

The compounds of the invention, exemplified by Formula I and II, may have chiral centers, e.g. chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. All though only one delocalized resonance structure may be depicted, all such forms are contemplated within the scope of the iinvention. For example, ene-amine tautomers can exist for purine, pyrimidine, imidazole, guanidine, amidine, and tetrazole systems and all their possible tautomeric forms are within the scope of the invention.

Salts and Hydrates

The compositions of this invention optionally comprise salts of the compounds herein, especially pharmaceutically acceptable non-toxic salts containing, for example, $Na^+$, $Li^+$, $K^+$, $Ca^{+2}$ and $Mg^{+2}$. Such salts may include those derived by combination of appropriate cations such as alkali and alkaline earth metal ions or ammonium and quaternary amino ions with an acid anion moiety, typically a carboxylic acid. Monovalent salts are preferred if a water soluble salt is desired.

Metal salts typically are prepared by reacting the metal hydroxide with a compound of this invention. Examples of metal salts which are prepared in this way are salts containing $Li^+$, $Na^+$, and $K^+$. A less soluble metal salt may be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the amino acids described above are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Methods of Inhibition of HIV Reverse Transcriptase

Another aspect of the invention relates to methods of inhibiting the activity of HIV reverse transcriptase comprising the step of treating a sample suspected of containing HIV with a composition of the invention.

Compositions of the invention may act as inhibitors of HIV reverse transcriptase, as intermediates for such inhibitors or have other utilities as described below. The inhibitors will bind to locations on the surface or in a cavity of HIV reverse transcriptase having a geometry unique to HIV reverse transcriptase. Compositions binding HIV reverse transcriptase may bind with varying degrees of reversibility. Those compounds binding substantially irreversibly are ideal candidates for use in this method of the invention. Once labeled, the substantially irreversibly binding compositions are useful as probes for the detection of HIV reverse transcriptase. Accordingly, the invention relates to methods of detecting HIV reverse transcriptase in a sample suspected of containing HIV reverse transcriptase comprising the steps of: treating a sample suspected of containing HIV reverse transcriptase with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl, carboxyl, sulfhydryl or amino.

Within the context of the invention, samples suspected of containing HIV reverse transcriptase include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which produces HIV reverse transcriptase, frequently a pathogenic organism such as HIV. Samples can be contained in any medium including water and organic solventwater mixtures. Samples include living organisms such as humans, and man made materials such as cell cultures.

The treating step of the invention comprises adding the composition of the invention to the sample or it comprises adding a precursor of the composition to the sample. The addition step comprises any method of administration as described above.

If desired, the activity of HIV reverse transcriptase after application of the composition can be observed by any method including direct and indirect methods of detecting HIV reverse transcriptase activity. Quantitative, qualitative, and semiquantitative methods of determining HIV reverse transcriptase activity are all contemplated. Typically one of the screening methods described above are applied, however, any other method such as observation of the physiological properties of a living organism are also applicable.

Organisms that contain HIV reverse transcriptase include the HIV virus. The compounds of this invention are useful in the treatment or prophylaxis of HIV infections in animals or in man.

However, in screening compounds capable of inhibiting human immunodeficiency viruses, it should be kept in mind that the results of enzyme assays may not correlate with cell culture assays. Thus, a cell based assay should be the primary screening tool.

Screens for HIV Reverse Transcriptase Inhibitors

Compositions of the invention are screened for inhibitory activity against HIV reverse transcriptase by any of the conventional techniques for evaluating enzyme activity. Within the context of the invention, typically compositions are first screened for inhibition of HIV reverse transcriptase in vitro and compositions showing inhibitory activity are then screened for activity in vivo. Compositions having in vitro Ki (inhibitory constants) of less then about $5\times10^{-6}$ M, typically less than about $1\times10^{-7}$ M and preferably less than about $5\times10^{-8}$ M are preferred for in vivo use.

Useful in vitro screens have been described in detail and will not be elaborated here. However, the examples describe suitable in vitro assays.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myTistate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise a combination according to the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of HIV infections as described below.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

Compositions of the invention are also used in combination with other active ingredients. Such combinations are selected based on the condition to be treated, cross-reactivities of ingredients and pharmaco-properties of the combination. For example, when treating viral infections the compositions of the invention may be combined with other antivirals such as other protease inhibitors, nucleoside reverse transcriptase inhibitors, non-nucleoside reverse transcriptase inhibitors or HIV integrase inhibitors.

It is possible to combine any compound of the invention with one or more other active ingredients in a unitary dosage form for simultaneous or sequential administration to an HIV infected patient. The combination therapy may be administered as a simultaneous or sequential regimen. When administered sequentially, the combination may be administered in two or more administrations. Second and third active ingredients in the combination may have anti-HIV activity. Exemplary active ingredients to be administered in combination with compounds of the invention are protease inhibitors, nucleoside reverse transcriptase inhibitors, non-nucleoside reverse transcriptase inhibitors, and HIV integrase inhibitors.

The combination therapy may provide "synergy" and "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-viral effect denotes an antiviral effect which is greater than the predicted purely additive effects of the individual compounds of the combination.

Metabolites of the Compounds of the Invention

Also falling within the scope of this invention are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabelled (e.g. $^{14}C$ or $^{3}H$) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no HIV reverse transcriptase inhibitory activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The phosphonate prodrugs of the invention typically will be stable in the digestive system but may be substantially hydrolyzed to the parental drug in the digestive lumen, liver or other metabolic organ, or within cells in general.

Exemplary Methods of Making the Compounds of the Invention

The invention provides many methods of making the compositions of the invention. The compositions are prepared by any of the applicable techniques of organic synthesis. Many such techniques are well known in the art, such as those elaborated in "Compendium of Organic Synthetic Methods" (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., "Advanced Organic Chemistry, Third Edition", (John Wiley & Sons, New York, 1985), "Comprehensive Organic Synthesis. Selectivity, Strategy & Efficiency in Modem Organic Chemistry. In 9 Volumes", Barry M. Trost, Editor-in-Chief (Pergamon Press, New York, 1993 printing).

Dialkyl phosphonates may be prepared according to the methods of: Quast et al (1974) *Synthesis* 490; Stowell et al (1990) *Tetrahedron Lett.* 3261; U.S. Pat. No. 5,663,159.

In general, synthesis of phosphonate esters is achieved by coupling a nucleophile amine or alcohol with the corresponding activated phosphonate electrophilic precursor. For example, chlorophosphonate addition on to 5'-hydroxy of nucleoside is a well known method for preparation of nucleoside phosphate monoesters. The activated precursor can be prepared by several well known methods. Chlorophosphonates useful for synthesis of the prodrugs are prepared from the substituted-1,3-propanediol (Wissner, et al, (1992) *J. Med Chem.* 35:1650). Chlorophosphonates are made by oxidation of the corresponding chlorophospholanes (Anderson, et al, (1984) *J. Org. Chem.* 49:1304) which are obtained by reaction of the substituted diol with phosphorus trichloride. Alternatively, the chlorophosphonate agent is made by treating substituted-1,3-diols with phosphorusoxychloride (Patois, et al, (1990) *J. Chem. Soc. Perkin Trans. I,* 1577). Chlorophosphonate species may also be generated in situ from corresponding cyclic phosphites (Silverburg, et al., (1996) *Tetrahedron Lett.,* 37:771-774), which in turn can be either made from chlorophospholane or phosphoramidate intermediate. Phosphoroflouridate intermediate prepared either from pyrophosphate or phosphoric acid may also act as precursor in preparation of cyclic prodrugs (Watanabe et al., (1988) *Tetrahedron Lett.,* 29:5763-66). Caution: fluorophosphonate compounds may be highly toxic!

Phosphonate prodrugs of the present invention may also be prepared from the precursor free acid by Mitsunobu reactions (Mitsunobu, (1981) *Synthesis,* 1; Campbell, (1992) *J. Org. Chem.,* 52:6331), and other acid coupling reagents including, but not limited to, carbodiimides (Alexander, et al, (1994) *Collect. Czech. Chem. Commun.* 59:1853; Casara, et al, (1992) *Bioorg. Med. Chem. Lett.,* 2:145; Ohashi, et al, (1988) *Tetrahedron Lett.,* 29:1189), and benzotriazolyloxytris-(dimethylamino)phosphonium salts (Campagne, et al, (1993) *Tetrahedron Lett.,* 34:6743).

Aryl halides undergo $Ni^{+2}$ catalyzed reaction with phosphite derivatives to give aryl phosphonate containing compounds (Balthazar, et al (1980) *J. Org. Chem.* 45:5425). Phosphonates may also be prepared from the chlorophosphonate in the presence of a palladium catalyst using aromatic triflates (Petrakis, et al, (1987) *J. Am. Chem. Soc.* 109:2831; Lu, et al, (1987) *Synthesis,* 726). In another method, aryl phosphonate esters are prepared from aryl phosphates under anionic rearrangement conditions (Melvin (1981) *Tetrahedron Lett.* 22:3375; Casteel, et al, (1991) *Synthesis,* 691). N-Alkoxy aryl salts with alkali metal derivatives of cyclic alkyl phosphonate provide general synthesis for heteroaryl-2-phosphonate linkers (Redmore (1970) *J. Org. Chem.* 35:4114). These above mentioned methods can also be extended to compounds where the $W^5$ group is a heterocycle. Cyclic-1,3-propanyl prodrugs of phosphonates are also synthesized from phosphonic diacids and substituted propane-1,3-diols using a coupling reagent such as 1,3-dicyclohexylcarbodiimide (DCC) in presence of a base (e.g., pyridine). Other carbodiimide based coupling agents like 1,3-disopropylcarbodiimide or water soluble reagent, 1-(3-dimethylaminopropyl)-3-ethyl-carbodiimide hydrochloride (EDCI) can also be utilized for the synthesis of cyclic phosphonate prodrugs.

The carbamoyl group may be formed by reaction of a hydroxy group according to the methods known in the art, including the teachings of Ellis, US 2002/0103378 A1 and Hajima, U.S. Pat. No. 6,018,049.

SCHEMES AND EXAMPLES

A number of exemplary methods for the preparation of the compositions of the invention are provided below. These methods are intended to illustrate the nature of such preparations are not intended to limit the scope of applicable methods.

These exemplary methods and examples are organized into two sections, "Examples: Section A", and "Examples: Section B". It is noted that the numbering convention for the preparations, schemes and examples taught in each section are independent of those taught in the other section. For example, Preparation 1 taught in "Examples: Section A" is an independent and distinct preparation from Preparation 1 taught in "Examples: Section B". General aspects of these exemplary methods are described below and in the Examples. Each of the products of the following processes is optionally separated, isolated, and/or purified prior to its use in subsequent processes.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be –100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to –100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to –100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g. inert gas environments) are common in the art and will be applied when applicable.

The terms "treated", "treating", "treatment", and the like, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two.

"Treating" indicates the reasonable and usual manner in which organic chemicals are allowed to react. Normal concentrations (0.01M to 10M, typically 0.1 M to 1 M), temperatures (–100° C. to 250° C., typically –78° C. to 150° C., more typically –78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis are used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modifications of each of the exemplary schemes above and in the examples (hereafter "exemplary schemes") leads to various analogs of the specific exemplary materials produce. The above cited citations describing suitable methods of organic synthesis are applicable to such modifications.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g. an enantiomer, substantially free of its stereoisomer may be obtained by resolution of the racemic mixture using a method such as formation of diastereomers using optically active resolving agents ("Stereochemistry of Carbon Compounds," (1962) by E. L. Eliel, McGraw Hill; Lochmuller, C. H., (1975) *J. Chromatogr.*, 113:(3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as brucine, quinine, ephedrine, strychnine, α- methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) *Stereochemistry of Organic Compounds*, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester, e.g. (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase (*Chiral Liquid Chromatography* (1989) W. J. Lough, Ed. Chapman and Hall, New York; Okamoto, (1990) *J of Chromatogr.* 513:375-378). Enriched or purified enantiomers can be distinguished by methods used to distinguish other chiral molecules with asymmetric carbon atoms, such as optical rotation and circular dichroism.

All literature and patent citations above are hereby, expressly incorporated by reference at the locations of their citation. Specifically cited sections or pages of the above cited works are incorporated by reference with specificity. The invention has been described in detail sufficient to allow one of ordinary skill in the art to make and use the subject matter of the following Embodiments. It is apparent that certain modifications of the methods and compositions of the following Embodiments can be made within the scope and spirit of the invention.

EXAMPLES

Section A

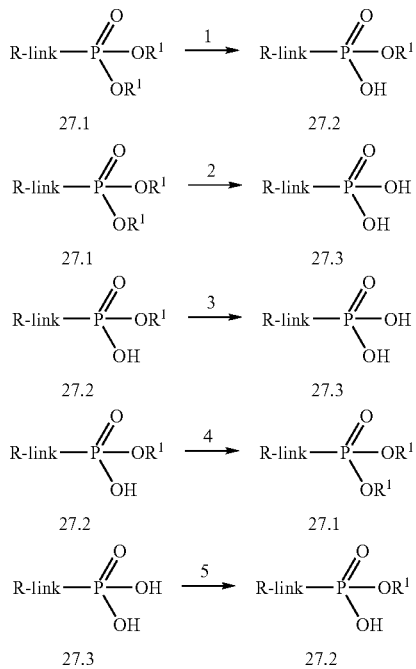

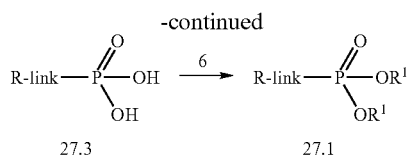

-continued 27.3 → 27.1 (step 6)

Scheme A shows the general interconversions of certain phosphonate compounds: acids —P(O)(OH)$_2$; mono-esters —P(O)(OR$_1$)(OH); and diesters —P(O)(OR$_1$)$_2$ in which the R$^1$ groups are independently selected, and defined herein before, and the phosphorus is attached through a carbon moiety (link, i.e. linker), which is attached to the rest of the molecule, e.g. drug or drug intermediate (R). The R$^1$ groups attached to the phosphonate esters in Scheme 1 may be changed using established chemical transformations. The interconversions may be carried out in the precursor compounds or the final products using the methods described below. The methods employed for a given phosphonate transformation depend on the nature of the substituent R$^1$. The preparation and hydrolysis of phosphonate esters is described in *Organic Phosphorus Compounds*, G. M. Kosolapoff, L. Maeir, eds, Wiley, 1976, p. 9ff.

The conversion of a phosphonate diester 27.1 into the corresponding phosphonate monoester 27.2 (Scheme A, Reaction 1) can be accomplished by a number of methods. For example, the ester 27.1 in which R$^1$ is an arylalkyl group such as benzyl, can be converted into the monoester compound 27.2 by reaction with a tertiary organic base such as diazabicyclooctane (DABCO) or quinuclidine, as described in *J. Org. Chem.*, 1995, 60:2946. The reaction is performed in an inert hydrocarbon solvent such as toluene or xylene, at about 110° C. The conversion of the diester 27.1 in which R$^1$ is an aryl group such as phenyl, or an alkenyl group such as allyl, into the monoester 27.2 can be effected by treatment of the ester 27.1 with a base such as aqueous sodium hydroxide in acetonitrile or lithium hydroxide in aqueous tetrahydrofuran. Phosphonate diesters 27.1 in which one of the groups R$^1$ is arylalkyl, such as benzyl, and the other is alkyl, can be converted into the monoesters 27.2 in which R$^1$ is alkyl, by hydrogenation, for example using a palladium on carbon catalyst. Phosphonate diesters in which both of the groups R$^1$ are alkenyl, such as allyl, can be converted into the monoester 27.2 in which R$^1$ is alkenyl, by treatment with chlorotris(triphenylphosphine)rhodium (Wilkinson's catalyst) in aqueous ethanol at reflux, optionally in the presence of diazabicyclooctane, for example by using the procedure described in *J. Org. Chem.*, 38:3224 1973 for the cleavage of allyl carboxylates.

The conversion of a phosphonate diester 27.1 or a phosphonate monoester 27.2 into the corresponding phosphonic acid 27.3 (Scheme A, Reactions 2 and 3) can effected by reaction of the diester or the monoester with trimethylsilyl bromide, as described in *J. Chem. Soc., Chem. Comm.*, 739, 1979. The reaction is conducted in an inert solvent such as, for example, dichloromethane, optionally in the presence of a silylating agent such as bis(trimethylsilyl)trifluoroacetamide, at ambient temperature. A phosphonate monoester 27.2 in which R$^1$ is arylalkyl such as benzyl, can be converted into the corresponding phosphonic acid 27.3 by hydrogenation over a palladium catalyst, or by treatment with hydrogen chloride in an ethereal solvent such as dioxane. A phosphonate monoester 27.2 in which R$^1$ is alkenyl such as, for example, allyl, can be converted into the phosphonic acid 27.3 by reaction with Wilkinson's catalyst in an aqueous organic solvent, for example in 15% aqueous acetonitrile, or in aqueous ethanol, for example using the procedure described in *Helv. Chim. Acta.*, 68:618, 1985. Palladium catalyzed hydrogenolysis of phosphonate esters 27.1 in which R$^1$ is benzyl is described in J. Org. Chem., 24:434, 1959. Platinum-catalyzed hydrogenolysis of phosphonate esters 27.1 in which R$^1$ is phenyl is described in *J. Amer. Chem. Soc.*, 78:2336, 1956.

The conversion of a phosphonate monoester 27.2 into a phosphonate diester 27.1 (Scheme A, Reaction 4) in which the newly introduced R$^1$ group is alkyl, arylalkyl, or haloalkyl such as chloroethyl, can be effected by a number of reactions in which the substrate 27.2 is reacted with a hydroxy compound R$^1$ OH, in the presence of a coupling agent. Suitable coupling agents are those employed for the preparation of carboxylate esters, and include a carbodiimide such as dicyclohexylcarbodiimide, in which case the reaction is preferably conducted in a basic organic solvent such as pyridine, or (benzotriazol-1-yloxy)tripyrrolidinophosphonium hexafluorophosphate (PYBOP, Sigma), in which case the reaction is performed in a polar solvent such as dimethylformamide, in the presence of a tertiary organic base such as diisopropylethylamine, or Aldrithiol-2 (Aldrich) in which case the reaction is conducted in a basic solvent such as pyridine, in the presence of a triaryl phosphine such as triphenylphosphine. Alternatively, the conversion of the phosphonate monoester 27.1 to the diester 27.1 can be effected by the use of the Mitsunobu reaction. The substrate is reacted with the hydroxy compound R$^1$ OH, in the presence of diethyl azodicarboxylate and a triarylphosphine such as triphenyl phosphine. Alternatively, the phosphonate monoester 27.2 can be transformed into the phosphonate diester 27.1, in which the introduced R$^1$ group is alkenyl or arylalkyl, by reaction of the monoester with the halide R$^1$Br, in which R$^1$ is as alkenyl or arylalkyl. The alkylation reaction is conducted in a polar organic solvent such as dimethylformamide or acetonitrile, in the presence of a base such as cesium carbonate. Alternatively, the phosphonate monoester can be transformed into the phosphonate diester in a two step procedure. In the first step, the phosphonate monoester 27.2 is transformed into the chloro analog —P(O)(OR$^1$)Cl by reaction with thionyl chloride or oxalyl chloride and the like, as described in Organic Phosphorus Compounds, G. M. Kosolapoff, L. Maeir, eds, Wiley, 1976, p. 17, and the thus-obtained product —P(O)(OR$^1$)Cl is then reacted with the hydroxy compound R$^1$ OH, in the presence of a base such as triethylamine, to afford the phosphonate diester 27.1.

A phosphonic acid —P(O)(OH)$_2$ can be transformed into a phosphonate monoester —P(O)(OR$^1$)(OH) (Scheme A, Reaction 5) by means of the methods described above of for the preparation of the phosphonate diester —P(O)(OR$^1$)$_2$ 27.1, except that only one molar proportion of the component R$^1$OH or R$^1$Br is employed.

A phosphonic acid —P(O)(OH)$_2$ 27.3 can be transformed into a phosphonate diester —P(O)(OR$^1$)$_2$ 27.1 (Scheme A, Reaction 6) by a coupling reaction with the hydroxy compound R$^1$ OH, in the presence of a coupling agent such as Aldrithiol-2 (Aldrich) and triphenylphosphine. The reaction is conducted in a basic solvent such as pyridine. Alternatively, phosphonic acids 27.3 can be transformed into phosphonic esters 27.1 in which R$^1$ is aryl, such as phenyl, by means of a coupling reaction employing, for example, phenol and dicyclohexylcarbodiimide in pyridine at about 70° C. Alternatively, phosphonic acids 27.3 can be transformed into phosphonic esters 27.1 in which R$^1$ is alkenyl, by means of an alkylation reaction. The phosphonic acid is reacted with the alkenyl bromide R$^1$Br in a polar organic solvent such as acetonitrile solution at reflux temperature, in the presence of a base such as cesium carbonate, to afford the phosphonic ester 27.1.

Phosphonate prodrugs of the present invention may also be prepared from the precursor free acid by Mitsunobu reactions (Mitsunobu, (1981) *Synthesis*, 1; Campbell, (1992) *J. Org. Chem.*, 52:6331), and other acid coupling reagents including, but not limited to, carbodiimides (Alexander, et al, (1994) *Collect. Czech. Chem. Commun.* 59:1853; Casara, et al, (1992) *Bioorg. Med. Chem. Lett.*, 2:145; Ohashi, et al, (1988) *Tetrahedron Lett.*, 29:1189), and benzotriazolyloxytris-(dimethylamino)phosphonium salts (Campagne, et al, (1993) *Tetrahedron Lett.*, 34:6743).

Preparation of Carboalkoxy-substituted Phosphonate Bisamidates, Monoamidates, Diesters and Monoesters.

A number of methods are available for the conversion of phosphonic acids into amidates and esters. In one group of methods, the phosphonic acid is either converted into an isolated activated intermediate such as a phosphoryl chloride, or the phosphonic acid is activated in situ for reaction with an amine or a hydroxy compound.

The conversion of phosphonic acids into phosphoryl chlorides is accomplished by reaction with thionyl chloride, for example as described in J. Gen. Chem. USSR, 1983, 53, 480, Zh. Obschei Khim., 1958, 28, 1063, or J. Org. Chem., 1994, 59, 6144, or by reaction with oxalyl chloride, as described in J. Am. Chem. Soc., 1994, 116, 3251, or J. Org. Chem., 1994, 59, 6144, or by reaction with phosphorus pentachloride, as described in J. Org. Chem., 2001, 66, 329, or in J. Med. Chem., 1995, 38, 1372. The resultant phosphoryl chlorides are then reacted with amines or hydroxy compounds in the presence of a base to afford the amidate or ester products.

Phosphonic acids are converted into activated imidazolyl derivatives by reaction with carbonyl diimidazole, as described in J. Chem. Soc., Chem. Comm., 1991, 312, or Nucleosides Nucleotides 2000, 19, 1885. Activated sulfonyloxy derivatives are obtained by the reaction of phosphonic acids with trichloromethylsulfonyl chloride, as described in J. Med. Chem. 1995, 38, 4958, or with triisopropylbenzenesulfonyl chloride, as described in Tet. Lett., 1996, 7857, or Bioorg. Med. Chem. Lett., 1998, 8, 663. The activated sulfonyloxy derivatives are then reacted with amines or hydroxy compounds to afford amidates or esters.

Alternatively, the phosphonic acid and the amine or hydroxy reactant are combined in the presence of a diimide coupling agent. The preparation of phosphonic amidates and esters by means of coupling reactions in the presence of dicyclohexyl carbodiimide is described, for example, in J. Chem. Soc., Chem. Comm., 1991, 312, or J. Med. Chem., 1980, 23, 1299 or Coll. Czech. Chem. Comm., 1987, 52, 2792. The use of ethyl dimethylaminopropyl carbodiimide for activation and coupling of phosphonic acids is described in Tet. Lett., 2001, 42, 8841, or Nucleosides Nucleotides, 2000, 19, 1885.

A number of additional coupling reagents have been described for the preparation of amidates and esters from phosphonic acids. The agents include Aldrithiol-2, and PYBOP and BOP, as described in J. Org. Chem., 1995, 60, 5214, and J. Med. Chem., 1997, 40, 3842, mesitylene-2-sulfonyl-3-nitro-1,2,4-triazole (MSNT), as described in J. Med. Chem., 1996, 39, 4958, diphenylphosphoryl azide, as described in J. Org. Chem., 1984, 49, 1158, 1-(2,4,6-triisopropylbenzenesulfonyl-3-nitro-1,2,4-triazole (TPSNT) as described in Bioorg. Med. Chem. Lett., 1998, 8, 1013, bromotris(dimethylamino)phosphonium hexafluorophosphate (BroP), as described in Tet. Lett., 1996, 37, 3997, 2-chloro-5,5-dimethyl-2-oxo-1,3,2-dioxaphosphinane, as described in Nucleosides Nucleotides 1995, 14, 871, and diphenyl chlorophosphate, as described in J. Med. Chem., 1988, 31, 1305.

Phosphonic acids are converted into amidates and esters by means of the Mitsonobu reaction, in which the phosphonic acid and the amine or hydroxy reactant are combined in the presence of a triaryl phosphine and a dialkyl azodicarboxylate. The procedure is described in Org. Lett., 2001, 3, 643, or J. Med. Chem., 1997, 40, 3842.

Phosphonic esters are also obtained by the reaction between phosphonic acids and halo compounds, in the presence of a suitable base. The method is described, for example, in Anal. Chem., 1987, 59, 1056, or J. Chem. Soc. Perkin Trans., I, 1993, 19, 2303, or J. Med. Chem., 1995, 38, 1372, or Tet. Lett., 2002, 43, 1161.

Schemes 1-4 illustrate the conversion of phosphonate esters and phosphonic acids into carboalkoxy-substituted phosphorobisamidates (Scheme 1), phosphoroamidates (Scheme 2), phosphonate monoesters (Scheme 3) and phosphonate diesters, (Scheme 4).

Scheme 1 illustrates various methods for the conversion of phosphonate diesters 1.1 into phosphorobisamidates 1.5. The diester 1.1, prepared as described previously, is hydrolyzed, either to the monoester 1.2 or to the phosphonic acid 1.6. The methods employed for these transformations are described above. The monoester 1.2 is converted into the monoamidate 1.3 by reaction with an aminoester 1.9, in which the group $R^2$ is H or alkyl, the group $R^4$ is an alkylene moiety such as, for example, $CHCH_3$, $CHPr^1$, $CH(CH_2Ph)$, $CH_2CH(CH_3)$ and the like, or a group present in natural or modified aminoacids, and the group $R^5$ is alkyl. The reactants are combined in the presence of a coupling agent such as a carbodiimide, for example dicyclohexyl carbodiimide, as described in J. Am. Chem. Soc., 1957, 79, 3575, optionally in the presence of an activating agent such as hydroxybenztriazole, to yield the amidate product 1.3. The amidate-forming reaction is also effected in the presence of coupling agents such as BOP, as described in J. Org. Chem., 1995, 60, 5214, Aldrithiol, PYBOP and similar coupling agents used for the preparation of amides and esters. Alternatively, the reactants 1.2 and 1.9 are transformed into the monoamidate 1.3 by means of a Mitsonobu reaction. The preparation of amidates by means of the Mitsonobu reaction is described in J. Med. Chem., 1995, 38, 2742. Equimolar amounts of the reactants are combined in an inert solvent such as tetrahydrofuran in the presence of a triaryl phosphine and a dialkyl azodicarboxylate. The thus-obtained monoamidate ester 1.3 is then transformed into amidate phosphonic acid 1.4. The conditions used for the hydrolysis reaction depend on the nature of the $R^1$ group, as described previously. The phosphonic acid amidate 1.4 is then reacted with an aminoester 1.9, as described above, to yield the bisamidate product 1.5, in which the amino substituents are the same or different.

An example of this procedure is shown in Scheme 1, Example 1. In this procedure, a dibenzyl phosphonate 1.14 is reacted with diazabicyclooctane (DABCO) in toluene at reflux, as described in J. Org. Chem., 1995, 60, 2946, to afford the monobenzyl phosphonate 1.15. The product is then reacted with equimolar amounts of ethyl alaninate 1.16 and dicyclohexyl carbodiimide in pyridine, to yield the amidate product 1.17. The benzyl group is then removed, for example by hydrogenolysis over a palladium catalyst, to give the monoacid product 1.18. This compound is then reacted in a Mitsonobu reaction with ethyl leucinate 1.19, triphenyl phosphine and diethylazodicarboxylate, as described in J. Med. Chem., 1995, 38, 2742, to produce the bisamidate product 1.20.

Using the above procedures, but employing, in place of ethyl leucinate 1.19 or ethyl alaninate 1.16, different aminoesters 1.9, the corresponding products 1.5 are obtained.

Alternatively, the phosphonic acid 1.6 is converted into the bisamidate 1.5 by use of the coupling reactions described above. The reaction is performed in one step, in which case the nitrogen-related substituents present in the product 1.5 are the same, or in two steps, in which case the nitrogen-related substituents can be different. An example of the method is shown in Scheme 1, Example 2. In this procedure, a phosphonic acid 1.6 is reacted in pyridine solution with excess ethyl phenylalaninate 1.21 and dicyclohexylcarbodiimide, for example as described in J. Chem. Soc., Chem. Comm., 1991, 1063, to give the bisamidate product 1.22.

Using the above procedures, but employing, in place of ethyl phenylalaninate, different aminoesters 1.9, the corresponding products 1.5 are obtained.

As a further alternative, the phosphonic acid 1.6 is converted into the mono or bis-activated derivative 1.7, in which Lv is a leaving group such as chloro, imidazolyl, triisopropylbenzenesulfonyloxy etc. The conversion of phosphonic acids into chlorides 1.7 (Lv=Cl) is effected by reaction with thionyl chloride or oxalyl chloride and the like, as described in Organic Phosphorus Compounds, G. M. Kosolapoff, L. Maeir, eds, Wiley, 1976, p. 17. The conversion of phosphonic acids into monoimidazolides 1.7 (Lv=imidazolyl) is described in J. Med. Chem., 2002, 45, 1284 and in J. Chem. Soc. Chem. Comm., 1991, 312. Alternatively, the phosphonic acid is activated by reaction with triisopropylbenzenesulfonyl chloride, as described in Nucleosides and Nucleotides, 2000, 10, 1885. The activated product is then reacted with the aminoester 1.9, in the presence of a base, to give the bisamidate 1.5. The reaction is performed in one step, in which case the nitrogen substituents present in the product 1.5 are the same, or in two steps, via the intermediate 1.11, in which case the nitrogen substituents can be different.

Examples of these methods are shown in Scheme 1, Examples 3 and 5. In the procedure illustrated in Scheme 1, Example 3, a phosphonic acid 1.6 is reacted with ten molar equivalents of thionyl chloride, as described in Zh. Obschei Khim., 1958, 28, 1063, to give the dichloro compound 1.23. The product is then reacted at reflux temperature in a polar aprotic solvent such as acetonitrile, and in the presence of a base such as triethylamine, with butyl serinate 1.24 to afford the bisamidate product 1.25.

Using the above procedures, but employing, in place of butyl serinate 1.24, different aminoesters 1.9, the corresponding products 1.5 are obtained.

In the procedure illustrated in Scheme 1, Example 5, the phosphonic acid 1.6 is reacted, as described in J. Chem. Soc. Chem. Comm., 1991, 312, with carbonyl diimidazole to give the imidazolide 1.32. The product is then reacted in acetonitrile solution at ambient temperature, with one molar equivalent of ethyl alaninate 1.33 to yield the monodisplacement product 1.34. The latter compound is then reacted with carbonyl diimidazole to produce the activated intermediate 1.35, and the product is then reacted, under the same conditions, with ethyl N-methylalaninate 1.33a to give the bisamidate product 1.36.

Using the above procedures, but employing, in place of ethyl alaninate 1.33 or ethyl N-methylalaninate 1.33a, different aminoesters 1.9, the corresponding products 1.5 are obtained.

The intermediate monoamidate 1.3 is also prepared from the monoester 1.2 by first converting the monoester into the activated derivative 1.8 in which Lv is a leaving group such as halo, imidazolyl etc, using the procedures described above.

The product 1.8 is then reacted with an aminoester 1.9 in the presence of a base such as pyridine, to give an intermediate monoamidate product 1.3. The latter compound is then converted, by removal of the $R^1$ group and coupling of the product with the aminoester 1.9, as described above, into the bisamidate 1.5.

An example of this procedure, in which the phosphonic acid is activated by conversion to the chloro derivative 1.26, is shown in Scheme 1, Example 4. In this procedure, the phosphonic monobenzyl ester 1.15 is reacted, in dichloromethane, with thionyl chloride, as described in Tet. Let., 1994, 35, 4097, to afford the phosphoryl chloride 1.26. The product is then reacted in acetonitrile solution at ambient temperature with one molar equivalent of ethyl 3-amino-2-methylpropionate 1.27 to yield the monoamidate product 1.28. The latter compound is hydrogenated in ethyl acetate over a 5% palladium on carbon catalyst to produce the monoacid product 1.29. The product is subjected to a Mitsonobu coupling procedure, with equimolar amounts of butyl alaninate 1.30, triphenyl phosphine, diethylazodicarboxylate and triethylamine in tetrahydrofuran, to give the bisamidate product 1.31.

Using the above procedures, but employing, in place of ethyl 3-amino-2-methylpropionate 1.27 or butyl alaninate 1.30, different aminoesters 1.9, the corresponding products 1.5 are obtained.

The activated phosphonic acid derivative 1.7 is also converted into the bisamidate 1.5 via the diamino compound 1.10. The conversion of activated phosphonic acid derivatives such as phosphoryl chlorides into the corresponding amino analogs 1.10, by reaction with ammonia, is described in Organic Phosphorus Compounds, G. M. Kosolapoff, L. Maeir, eds, Wiley, 1976. The diamino compound 1.10 is then reacted at elevated temperature with a haloester 1.12, in a polar organic solvent such as dimethylformamide, in the presence of a base such as dimethylaminopyridine or potassium carbonate, to yield the bisamidate 1.5.

An example of this procedure is shown in Scheme 1, Example 6. In this method, a dichlorophosphonate 1.23 is reacted with ammonia to afford the diamide 1.37. The reaction is performed in aqueous, aqueous alcoholic or alcoholic solution, at reflux temperature. The resulting diamino compound is then reacted with two molar equivalents of ethyl 2-bromo-3-methylbutyrate 1.38, in a polar organic solvent such as N-methylpyrrolidinone at ca. 150° C., in the presence of a base such as potassium carbonate, and optionally in the presence of a catalytic amount of potassium iodide, to afford the bisamidate product 1.39.

Using the above procedures, but employing, in place of ethyl 2-bromo-3-methylbutyrate 1.38, different haloesters 1.12 the corresponding products 1.5 are obtained.

The procedures shown in Scheme 1 are also applicable to the preparation of bisamidates in which the aminoester moiety incorporates different functional groups. Scheme 1, Example 7 illustrates the preparation of bisamidates derived from tyrosine. In this procedure, the monoimidazolide 1.32 is reacted with propyl tyrosinate 1.40, as described in Example 5, to yield the monoamidate 1.41. The product is reacted with carbonyl diimidazole to give the imidazolide 1.42, and this material is reacted with a further molar equivalent of propyl tyrosinate to produce the bisamidate product 1.43.

Using the above procedures, but employing, in place of propyl tyrosinate 1.40, different aminoesters 1.9, the corresponding products 1.5 are obtained. The aminoesters employed in the two stages of the above procedure can be the same or different, so that bisamidates with the same or different amino substituents are prepared.

Scheme 2 illustrates methods for the preparation of phosphonate monoamidates. In one procedure, a phosphonate monoester 1.1 is converted, as described in Scheme 1, into the activated derivative 1.8. This compound is then reacted, as described above, with an aminoester 1.9, in the presence of a base, to afford the monoamidate product 2.1. The procedure is illustrated in Scheme 2, Example 1. In this method, a monophenyl phosphonate 2.7 is reacted with, for example, thionyl chloride, as described in J. Gen. Chem. USSR., 1983, 32, 367, to give the chloro product 2.8. The product is then reacted, as described in Scheme 1, with ethyl alaninate 2.9, to yield the amidate 2.10.

Using the above procedures, but employing, in place of ethyl alaninate 2.9, different aminoesters 1.9, the corresponding products 2.1 are obtained.

Alternatively, the phosphonate monoester 1.1 is coupled, as described in Scheme 1, with an aminoester 1.9 to produce the amidate 2.1. If necessary, the $R^1$ substituent is then altered, by initial cleavage to afford the phosphonic acid 2.2. The procedures for this transformation depend on the nature of the $R^1$ group, and are described above. The phosphonic acid is then transformed into the ester amidate product 2.3, by reaction with the hydroxy compound $R^3OH$, in which the group $R^3$ is aryl, heteroaryl, alkyl, cycloalkyl, haloalkyl etc, using the same coupling procedures (carbodiimide, Aldrithiol-2, PYBOP, Mitsonobu reaction etc) described in Scheme 1 for the coupling of amines and phosphonic acids.

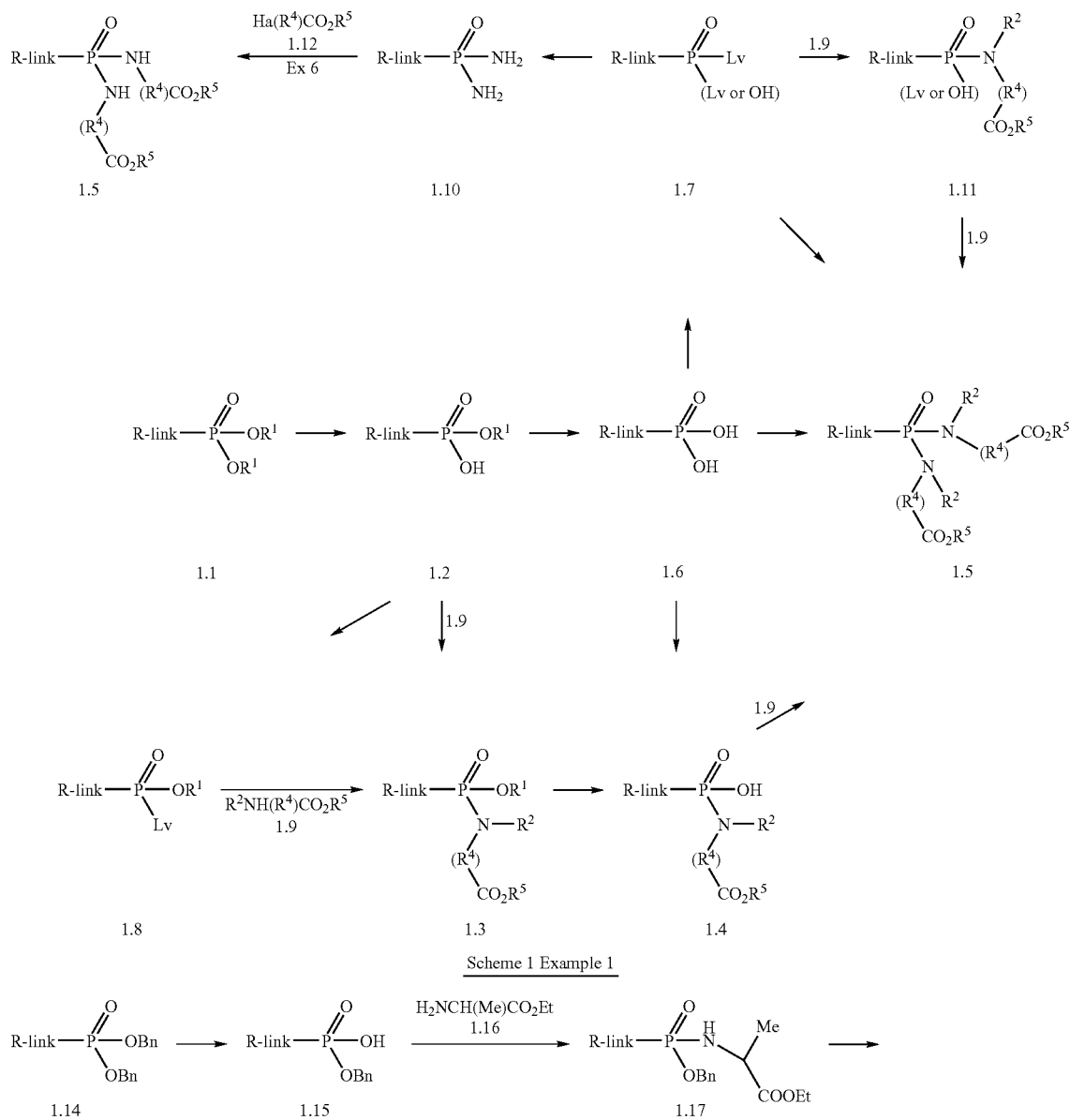

-continued
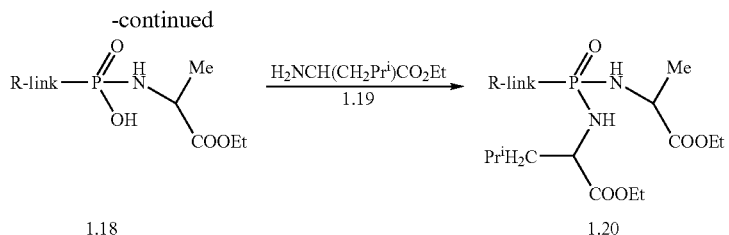
1.18 → 1.20
Scheme 1 Example 2
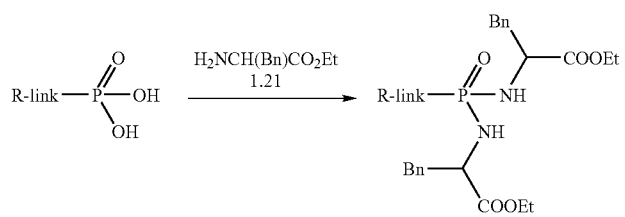
1.6 → 1.22
Scheme 1 Example 3
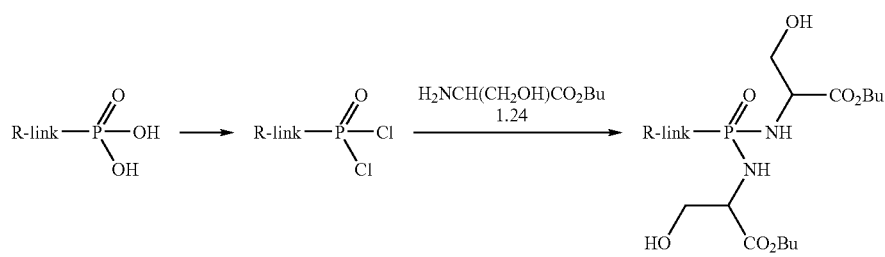
1.6 → 1.23 → 1.25
Scheme 1 Example 4
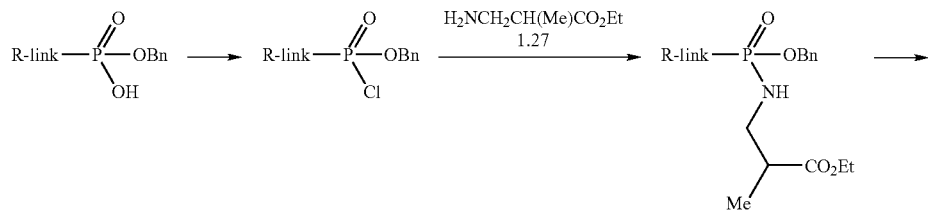
1.15 → 1.26 → 1.28
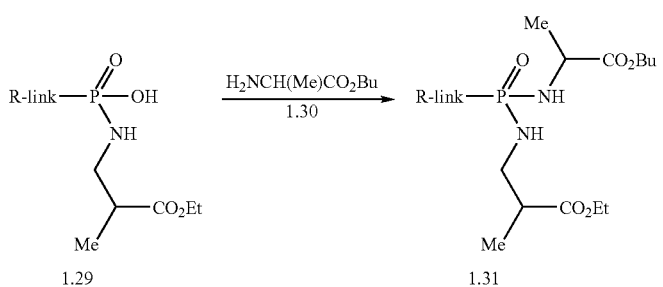
1.29 → 1.31
Scheme 1 Example 5
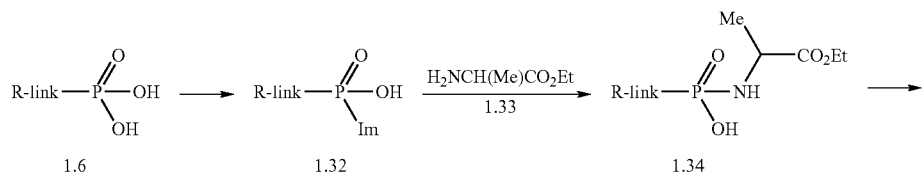
1.6 → 1.32 → 1.34

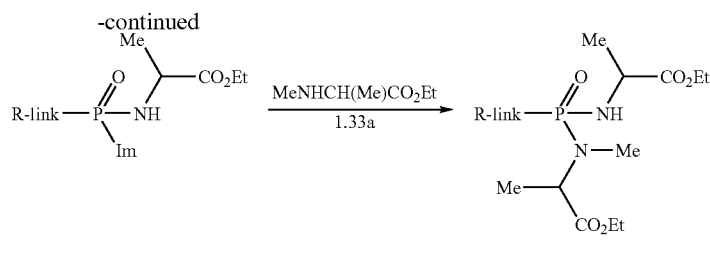

1.35                     1.36
Scheme 1 Example 6

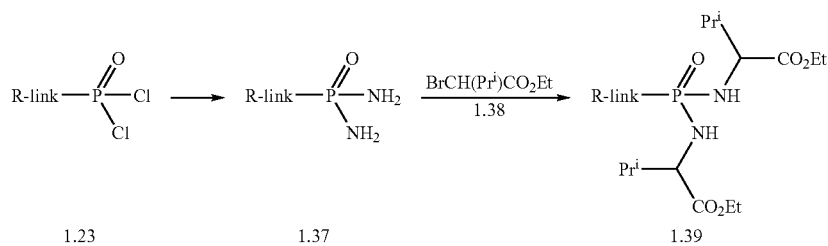

Scheme 1 Example 7

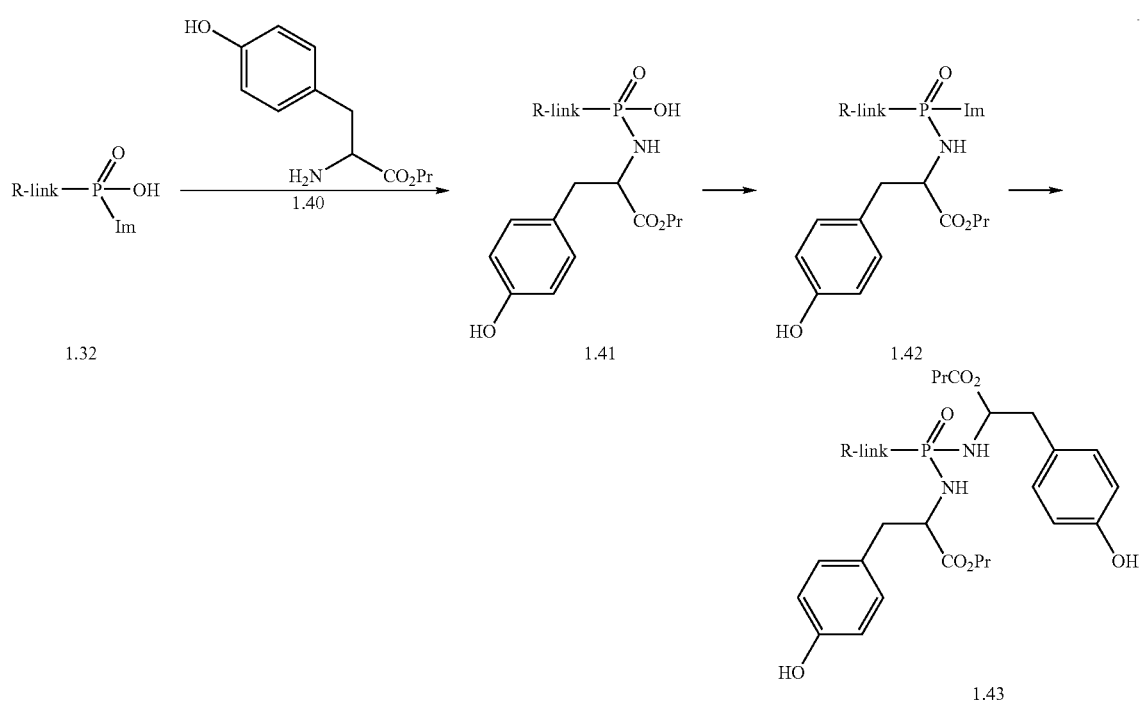

Examples of this method are shown in Scheme 2, Examples and 2 and 3. In the sequence shown in Example 2, a monobenzyl phosphonate 2.11 is transformed by reaction with ethyl alaninate, using one of the methods described above, into the monoamidate 2.12. The benzyl group is then removed by catalytic hydrogenation in ethyl acetate solution over a 5% palladium on carbon catalyst, to afford the phosphonic acid amidate 2.13. The product is then reacted in dichloromethane solution at ambient temperature with equimolar amounts of 1-(dimethylaminopropyl)-3-ethylcarbodiimide and trifluoroethanol 2.14, for example as described in Tet. Lett., 2001, 42, 8841, to yield the amidate ester 2.15.

In the sequence shown in Scheme 2, Example 3, the monoamidate 2.13 is coupled, in tetrahydrofuran solution at ambient temperature, with equimolar amounts of dicyclohexyl carbodiimide and 4-hydroxy-N-methylpiperidine 2.16, to produce the amidate ester product 2.17.

Using the above procedures, but employing, in place of the ethyl alaninate product 2.12 different monoacids 2.2, and in place of trifluoroethanol 2.14 or 4-hydroxy-N-methylpiperidine 2.16, different hydroxy compounds $R^3OH$, the corresponding products 2.3 are obtained.

Alternatively, the activated phosphonate ester 1.8 is reacted with ammonia to yield the amidate 2.4. The product is then reacted, as described in Scheme 1, with a haloester 2.5, in the presence of a base, to produce the amidate product 2.6. If appropriate, the nature of the $R^1$ group is changed, using the procedures described above, to give the product 2.3. The method is illustrated in Scheme 2, Example 4. In this sequence, the monophenyl phosphoryl chloride 2.18 is reacted, as described in Scheme 1, with ammonia, to yield the amino product 2.19. This material is then reacted in N-methylpyrrolidinone solution at 170° C. with butyl 2-bromo-3-phenylpropionate 2.20 and potassium carbonate, to afford the amidate product 2.21.

Using these procedures, but employing, in place of butyl 2-bromo-3-phenylpropionate 2.20, different haloesters 2.5, the corresponding products 2.6 are obtained.

The monoamidate products 2.3 are also prepared from the doubly activated phosphonate derivatives 1.7. In this procedure, examples of which are described in Synlett., 1998, 1, 73, the intermediate 1.7 is reacted with a limited amount of the aminoester 1.9 to give the mono-displacement product 1.11.

The latter compound is then reacted with the hydroxy compound $R^3OH$ in a polar organic solvent such as dimethylformamide, in the presence of a base such as diisopropylethylamine, to yield the monoamidate ester 2.3.

The method is illustrated in Scheme 2, Example 5. In this method, the phosphoryl dichloride 2.22 is reacted in dichloromethane solution with one molar equivalent of ethyl N-methyl tyrosinate 2.23 and dimethylaminopyridine, to generate the monoamidate 2.24. The product is then reacted with phenol 2.25 in dimethylformamide containing potassium carbonate, to yield the ester amidate product 2.26.

Using these procedures, but employing, in place of ethyl N-methyl tyrosinate 2.23 or phenol 2.25, the aminoesters 1.9 and/or the hydroxy compounds $R^3OH$, the corresponding products 2.3 are obtained.

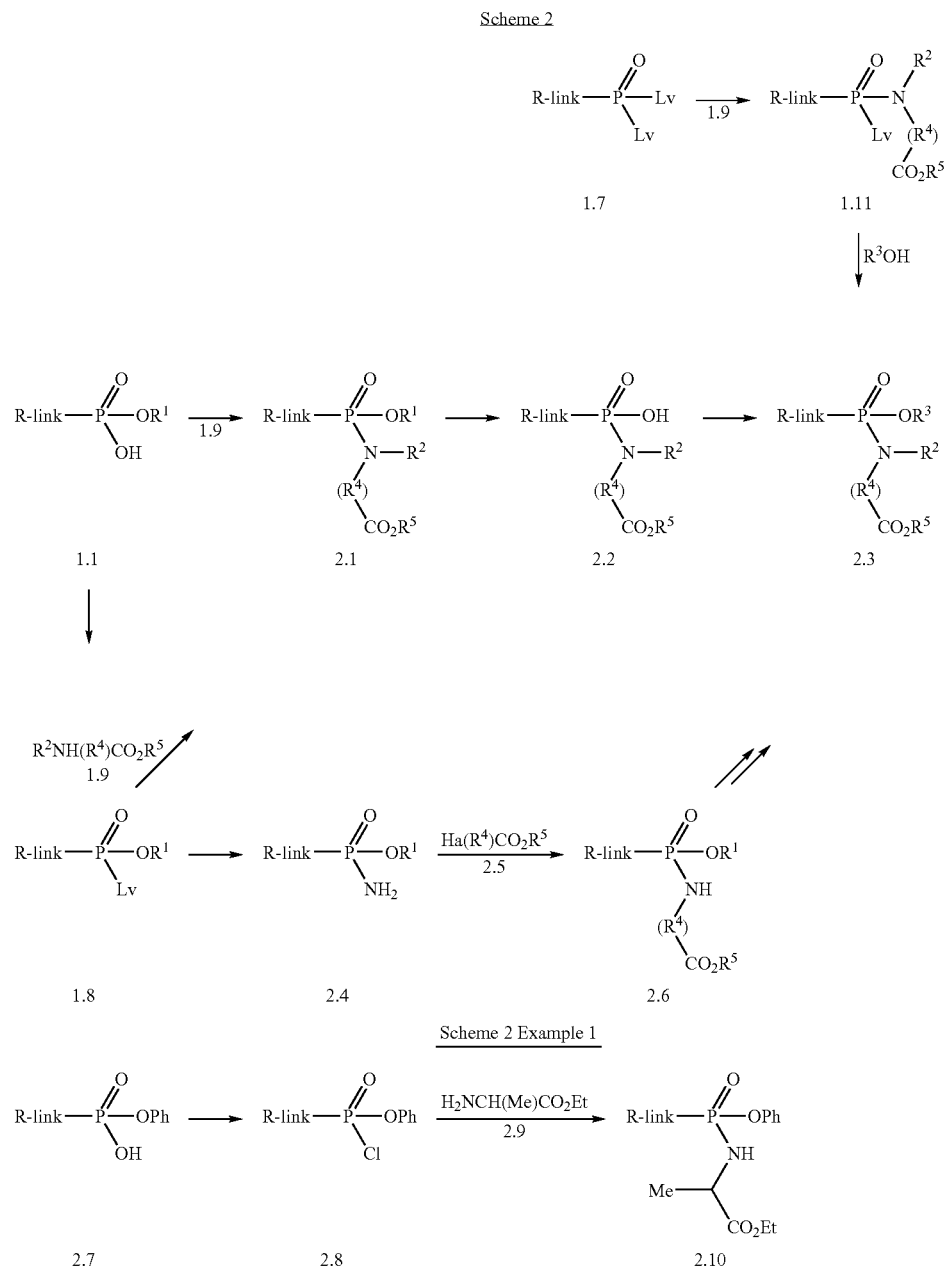

Scheme 2 Example 2

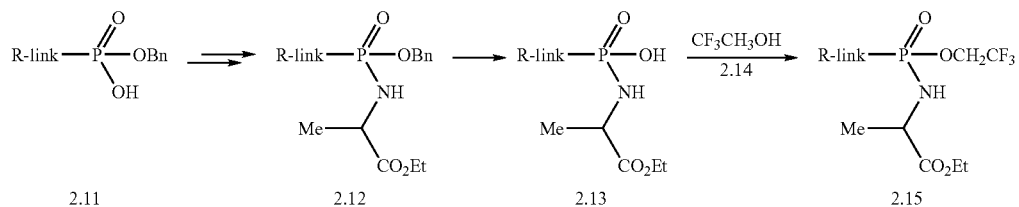

Scheme 2 Example 3

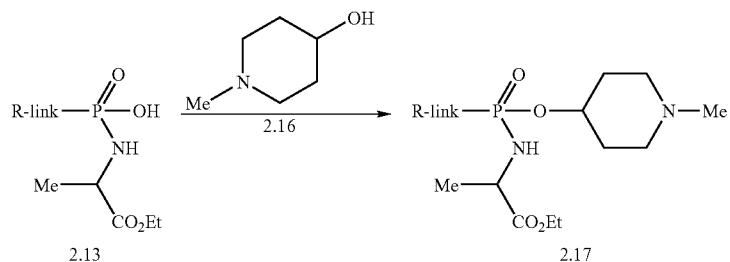

Scheme 2 Example 4

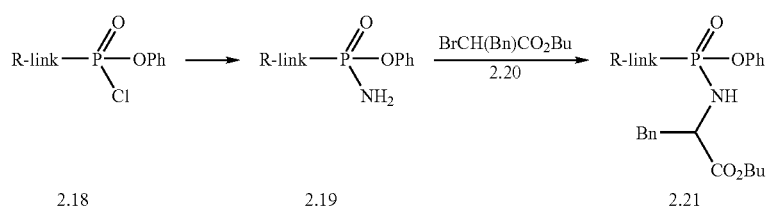

Scheme 2 Example 5

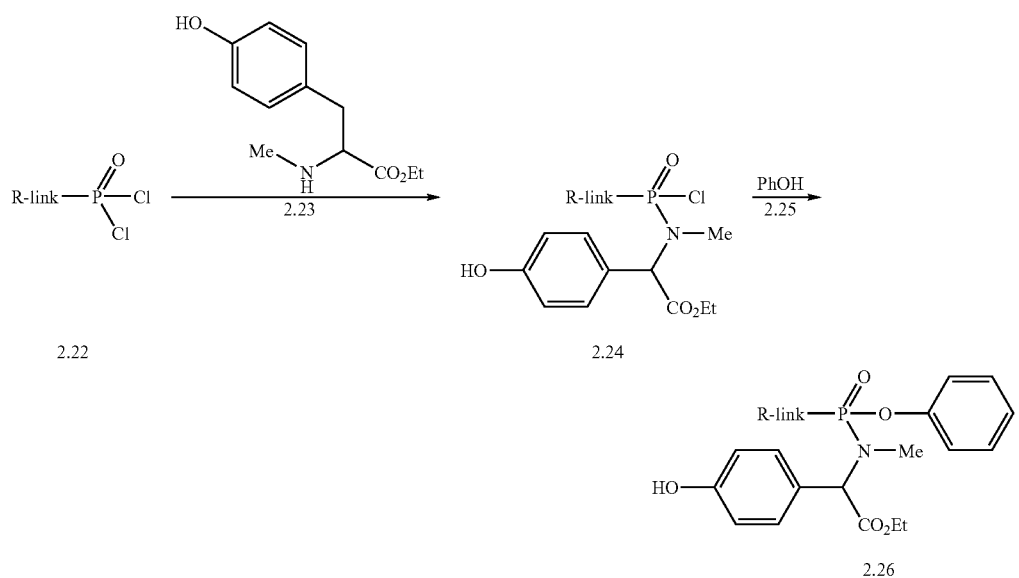

Scheme 3 illustrates methods for the preparation of carboalkoxy-substituted phosphonate diesters in which one of the ester groups incorporates a carboalkoxy substituent.

In one procedure, a phosphonate monoester 1.1, prepared as described above, is coupled, using one of the methods described above, with a hydroxyester 3.1, in which the groups $R^4$ and $R^5$ are as described in Scheme 1. For example, equimolar amounts of the reactants are coupled in the presence of a carbodiimide such as dicyclohexyl carbodiimide, as described in Aust. J. Chem., 1963, 609, optionally in the presence of dimethylaminopyridine, as described in Tet., 1999, 55, 12997. The reaction is conducted in an inert solvent at ambient temperature.

The procedure is illustrated in Scheme 3, Example 1. In this method, a monophenyl phosphonate 3.9 is coupled, in dichloromethane solution in the presence of dicyclohexyl carbodiimide, with ethyl 3-hydroxy-2-methylpropionate 3.10 to yield the phosphonate mixed diester 3.11.

Using this procedure, but employing, in place of ethyl 3-hydroxy-2-methylpropionate 3.10, different hydroxyesters 3.1, the corresponding products 3.2 are obtained.

The conversion of a phosphonate monoester 1.1 into a mixed diester 3.2 is also accomplished by means of a Mitsonobu coupling reaction with the hydroxyester 3.1, as described in Org. Lett., 2001, 643. In this method, the reactants 1.1 and 3.1 are combined in a polar solvent such as tetrahydrofuran, in the presence of a triarylphosphine and a dialkyl azodicarboxylate, to give the mixed diester 3.2. The $R^1$ substituent is varied by cleavage, using the methods described previously, to afford the monoacid product 3.3. The product is then coupled, for example using methods described above, with the hydroxy compound $R^3OH$, to give the diester product 3.4.

The procedure is illustrated in Scheme 3, Example 2. In this method, a monoallyl phosphonate 3.12 is coupled in tetrahydrofuran solution, in the presence of triphenylphosphine and diethylazodicarboxylate, with ethyl lactate 3.13 to give the mixed diester 3.14. The product is reacted with tris(triphenylphosphine) rhodium chloride (Wilkinson catalyst) in acetonitrile, as described previously, to remove the allyl group and produce the monoacid product 3.15. The latter compound is then coupled, in pyridine solution at ambient temperature, in the presence of dicyclohexyl carbodiimide, with one molar equivalent of 3-hydroxypyridine 3.16 to yield the mixed diester 3.17.

Using the above procedures, but employing, in place of the ethyl lactate 3.13 or 3-hydroxypyridine, a different hydroxyester 3.1 and/or a different hydroxy compound $R^3OH$, the corresponding products 3.4 are obtained.

The mixed diesters 3.2 are also obtained from the monoesters 1.1 via the intermediacy of the activated monoesters 3.5. In this procedure, the monoester 1.1 is converted into the activated compound 3.5 by reaction with, for example, phosphorus pentachloride, as described in J. Org. Chem., 2001, 66, 329, or with thionyl chloride or oxalyl chloride (Lv=Cl), or with triisopropylbenzenesulfonyl chloride in pyridine, as described in Nucleosides and Nucleotides, 2000, 19, 1885, or with carbonyl diimidazole, as described in J. Med. Chem., 2002, 45, 1284. The resultant activated monoester is then reacted with the hydroxyester 3.1, as described above, to yield the mixed diester 3.2.

The procedure is illustrated in Scheme 3, Example 3. In this sequence, a monophenyl phosphonate 3.9 is reacted, in acetonitrile solution at 70° C., with ten equivalents of thionyl chloride, so as to produce the phosphoryl chloride 3.19. The product is then reacted with ethyl 4-carbamoyl-2-hydroxybutyrate 3.20 in dichloromethane containing triethylamine, to give the mixed diester 3.21.

Using the above procedures, but employing, in place of ethyl 4-carbamoyl-2-hydroxybutyrate 3.20, different hydroxyesters 3.1, the corresponding products 3.2 are obtained.

The mixed phosphonate diesters are also obtained by an alternative route for incorporation of the $R^3O$ group into intermediates 3.3 in which the hydroxyester moiety is already incorporated. In this procedure, the monoacid intermediate 3.3 is converted into the activated derivative 3.6 in which Lv is a leaving group such as chloro, imidazole, and the like, as previously described. The activated intermediate is then reacted with the hydroxy compound $R^3OH$, in the presence of a base, to yield the mixed diester product 3.4.

The method is illustrated in Scheme 3, Example 4. In this sequence, the phosphonate monoacid 3.22 is reacted with trichloromethanesulfonyl chloride in tetrahydrofuran containing collidine, as described in J. Med. Chem., 1995, 38, 4648, to produce the trichloromethanesulfonyloxy product 3.23. This compound is reacted with 3-(morpholinomethyl) phenol 3.24 in dichloromethane containing triethylamine, to yield the mixed diester product 3.25.

Using the above procedures, but employing, in place of with 3-(morpholinomethyl)phenol 3.24, different carbinols $R^3OH$, the corresponding products 3.4 are obtained.

The phosphonate esters 3.4 are also obtained by means of alkylation reactions performed on the monoesters 1.1. The reaction between the monoacid 1.1 and the haloester 3.7 is performed in a polar solvent in the presence of a base such as diisopropylethylamine, as described in Anal. Chem., 1987, 59, 1056, or triethylamine, as described in J. Med. Chem., 1995, 38, 1372, or in a non-polar solvent such as benzene, in the presence of 18-crown-6, as described in Syn. Comm., 1995, 25, 3565.

The method is illustrated in Scheme 3, Example 5. In this procedure, the monoacid 3.26 is reacted with ethyl 2-bromo-3-phenylpropionate 3.27 and diisopropylethylamine in dimethylformamide at 80° C. to afford the mixed diester product 3.28.

Using the above procedure, but employing, in place of ethyl 2-bromo-3-phenylpropionate 3.27, different haloesters 3.7, the corresponding products 3.4 are obtained.

Scheme 3

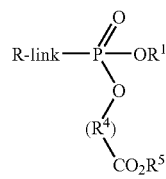

3.4

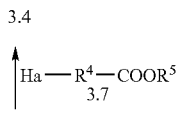

-continued
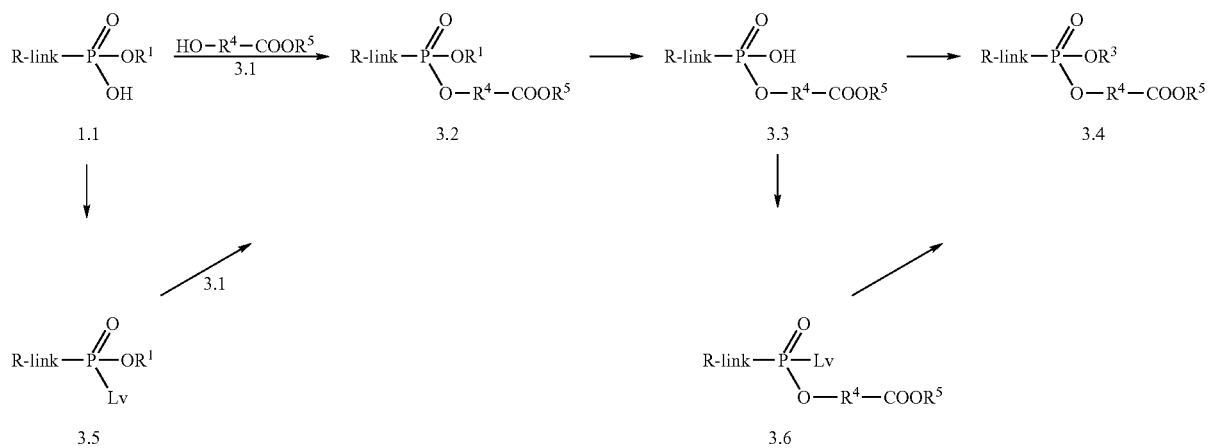
Scheme 3 Example 1
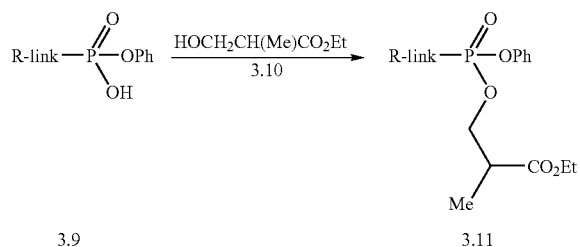
Scheme 3 Example 2
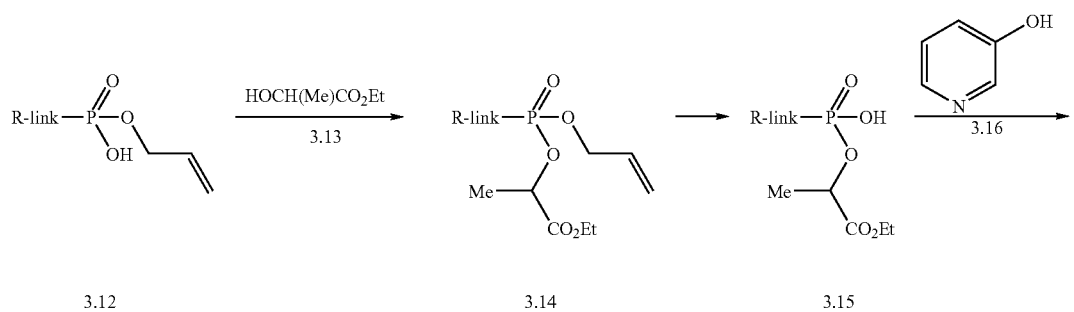
Scheme 3 Example 3
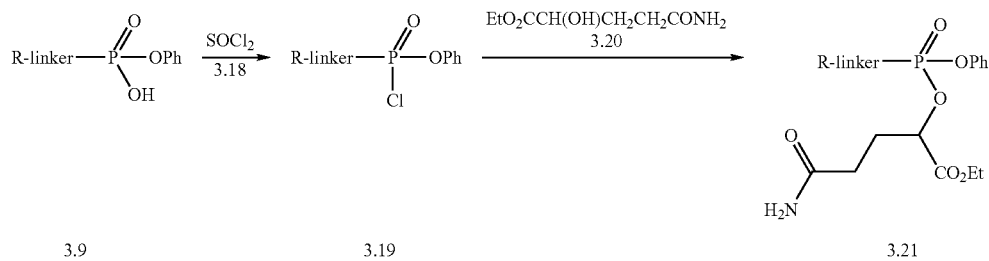

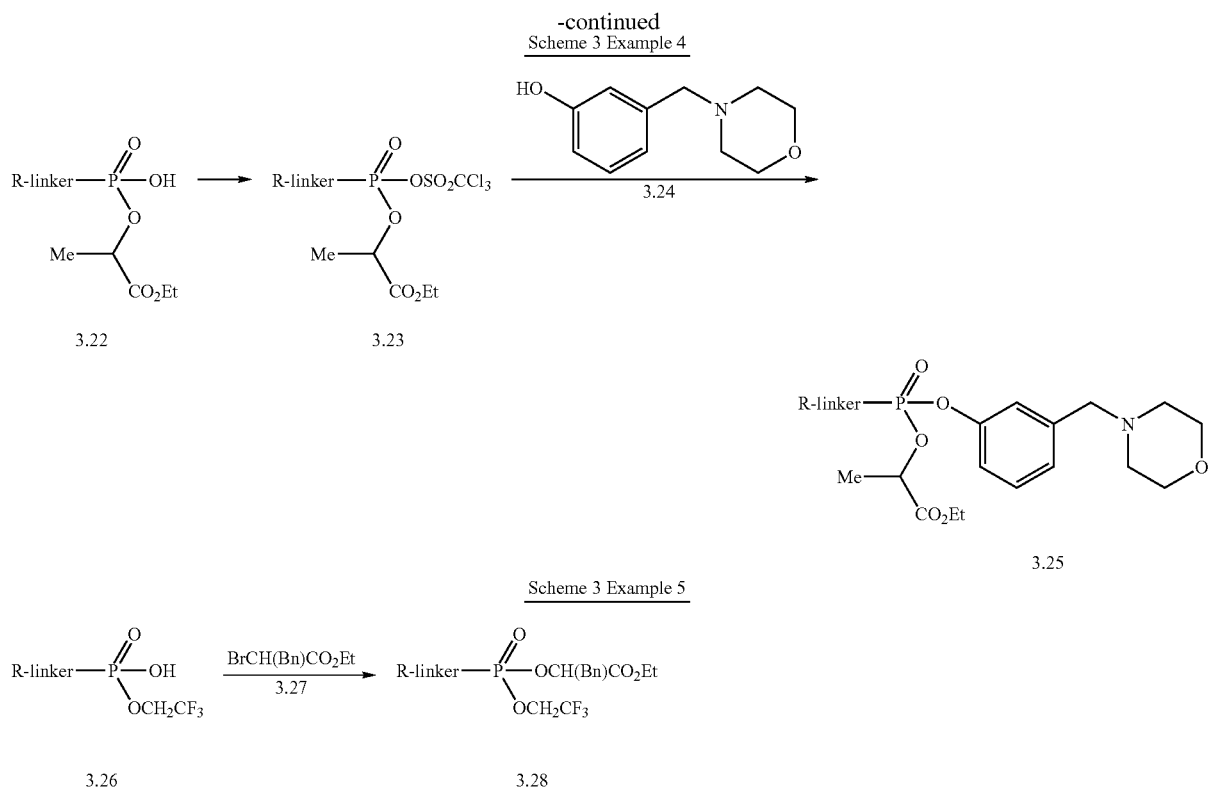

Scheme 4 illustrates methods for the preparation of phosphonate diesters in which both the ester substituents incorporate carboalkoxy groups.

The compounds are prepared directly or indirectly from the phosphonic acids 1.6. In one alternative, the phosphonic acid is coupled with the hydroxyester 4.2, using the conditions described previously in Schemes 1-3, such as coupling reactions using dicyclohexyl carbodiimide or similar reagents, or under the conditions of the Mitsonobu reaction, to afford the diester product 4.3 in which the ester substituents are identical.

This method is illustrated in Scheme 4, Example 1. In this procedure, the phosphonic acid 1.6 is reacted with three molar equivalents of butyl lactate 4.5 in the presence of Aldrithiol-2 and triphenyl phosphine in pyridine at ca. 70° C., to afford the diester 4.6.

Using the above procedure, but employing, in place of butyl lactate 4.5, different hydroxyesters 4.2, the corresponding products 4.3 are obtained.

Alternatively, the diesters 4.3 are obtained by alkylation of the phosphonic acid 1.6 with a haloester 4.1. The alkylation reaction is performed as described in Scheme 3 for the preparation of the esters 3.4.

This method is illustrated in Scheme 4, Example 2. In this procedure, the phosphonic acid 1.6 is reacted with excess ethyl 3-bromo-2-methylpropionate 4.7 and diisopropylethylamine in dimethylformamide at ca. 80° C., as described in Anal. Chem., 1987, 59, 1056, to produce the diester 4.8.

Using the above procedure, but employing, in place of ethyl 3-bromo-2-methylpropionate 4.7, different haloesters 4.1, the corresponding products 4.3 are obtained.

The diesters 4.3 are also obtained by displacement reactions of activated derivatives 1.7 of the phosphonic acid with the hydroxyesters 4.2. The displacement reaction is performed in a polar solvent in the presence of a suitable base, as described in Scheme 3. The displacement reaction is performed in the presence of an excess of the hydroxyester, to afford the diester product 4.3 in which the ester substituents are identical, or sequentially with limited amounts of different hydroxyesters, to prepare diesters 4.3 in which the ester substituents are different.

The methods are illustrated in Scheme 4, Examples 3 and 4. As shown in Example 3, the phosphoryl dichloride 2.22 is reacted with three molar equivalents of ethyl 3-hydroxy-2-(hydroxymethyl)propionate 4.9 in tetrahydrofuran containing potassium carbonate, to obtain the diester product 4.10.

Using the above procedure, but employing, in place of ethyl 3-hydroxy-2-(hydroxymethyl)propionate 4.9, different hydroxyesters 4.2, the corresponding products 4.3 are obtained.

Scheme 4, Example 4 depicts the displacement reaction between equimolar amounts of the phosphoryl dichloride 2.22 and ethyl 2-methyl-3-hydroxypropionate 4.11, to yield the monoester product 4.12. The reaction is conducted in acetonitrile at 70° C. in the presence of diisopropylethylamine. The product 4.12 is then reacted, under the same conditions, with one molar equivalent of ethyl lactate 4.13, to give the diester product 4.14. Using the above procedures, but employing, in place of ethyl 2-methyl-3-hydroxypropionate 4.11 and ethyl lactate 4.13, sequential reactions with different hydroxyesters 4.2, the corresponding products 4.3 are obtained.

Scheme 4
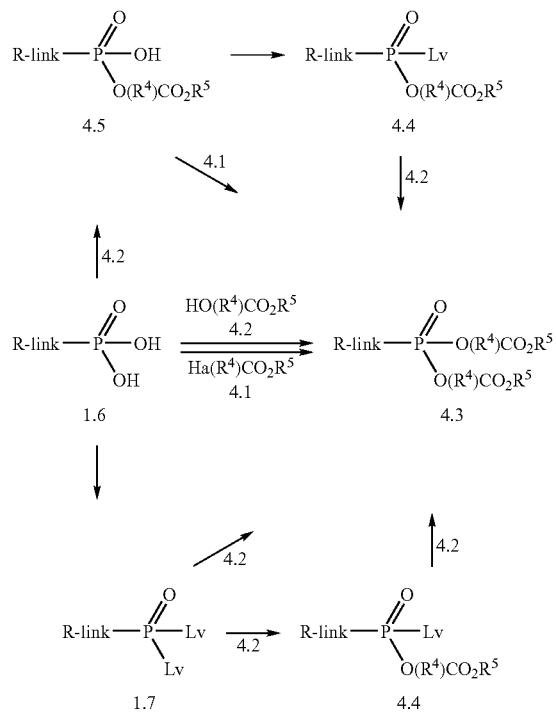
Scheme 4 Example 1
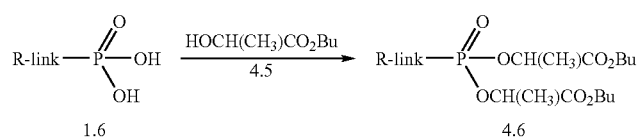
Scheme 4 Example 2
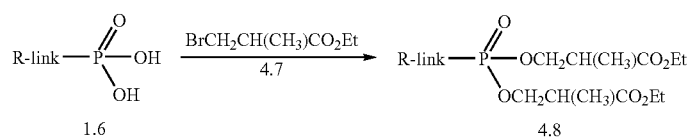
Scheme 4 Example 3
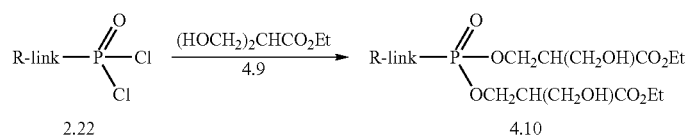
Scheme 4 Example 4
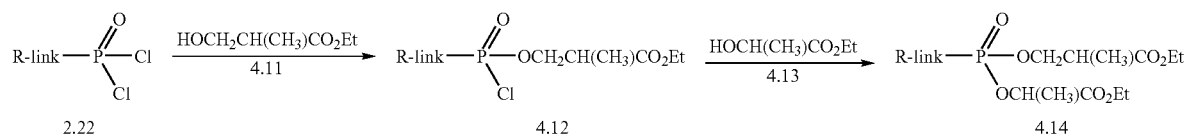
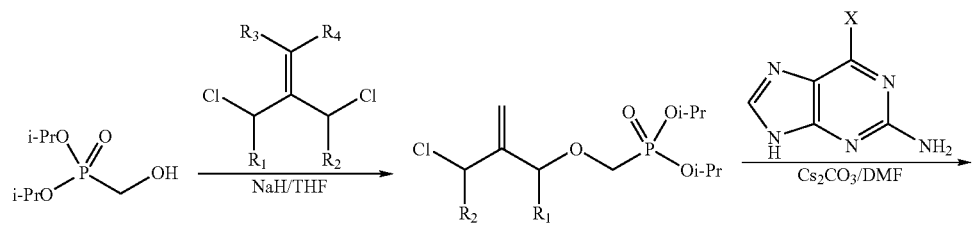

-continued
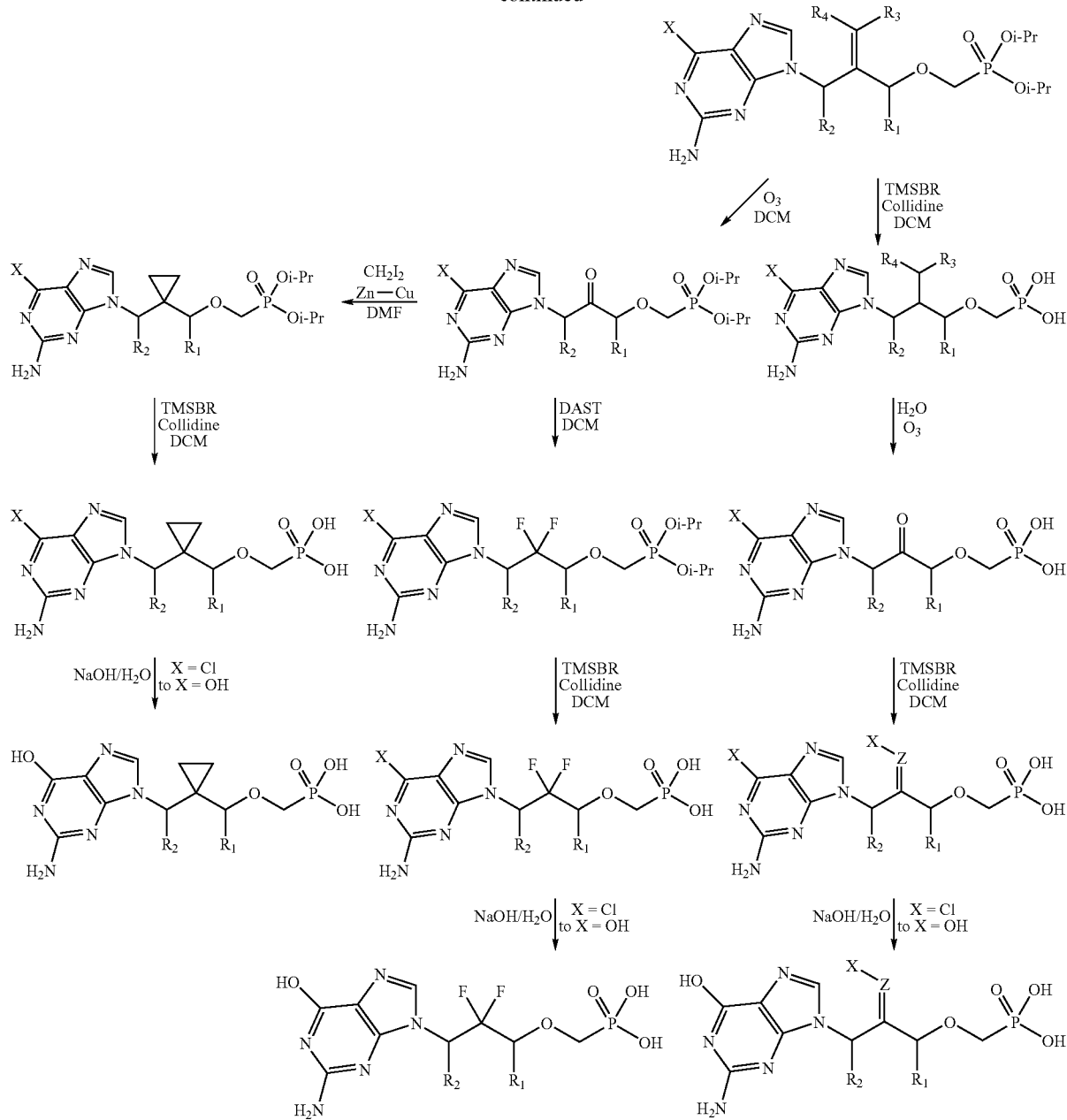
R$_1$, R$_2$, R$_3$, R$_4$ are independently H, Me
R$_1$ can also be CH=CH$_2$ in the cases where R$_3$ and R$_4$ are present
Stereoisomers are separated using chiral chromatography
-continued
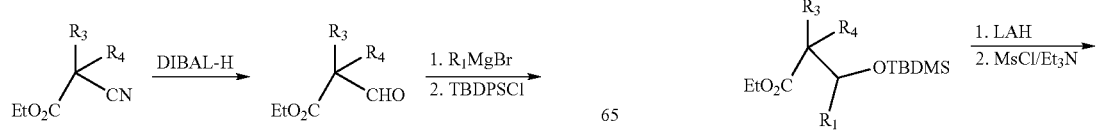

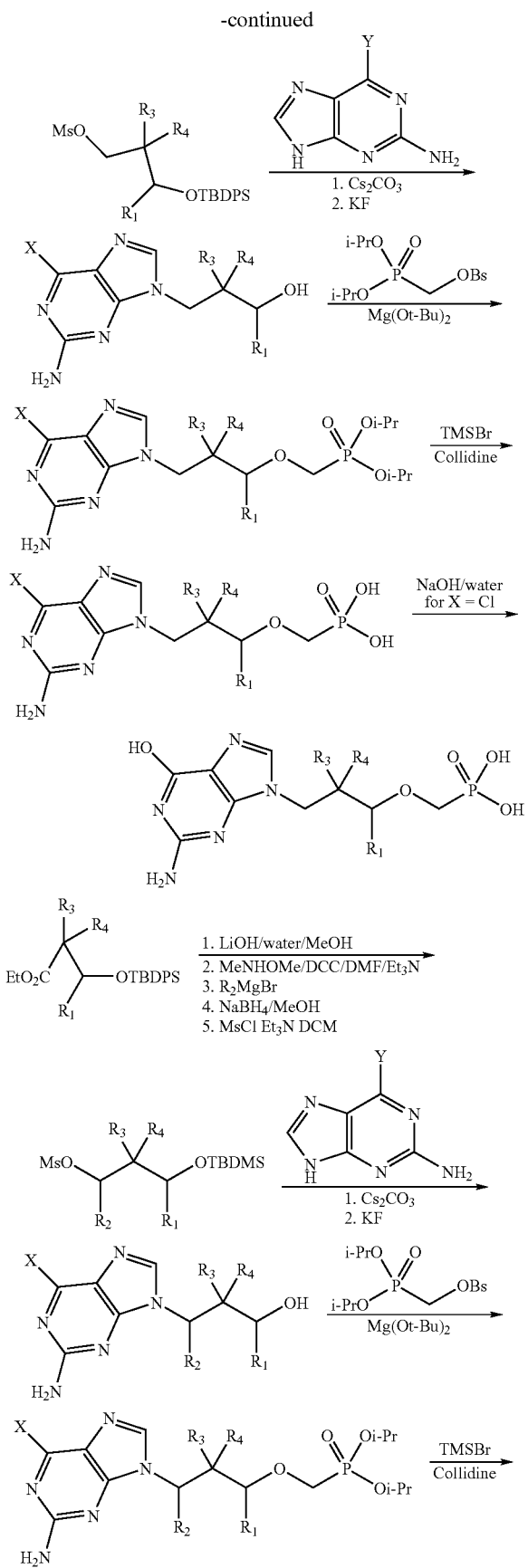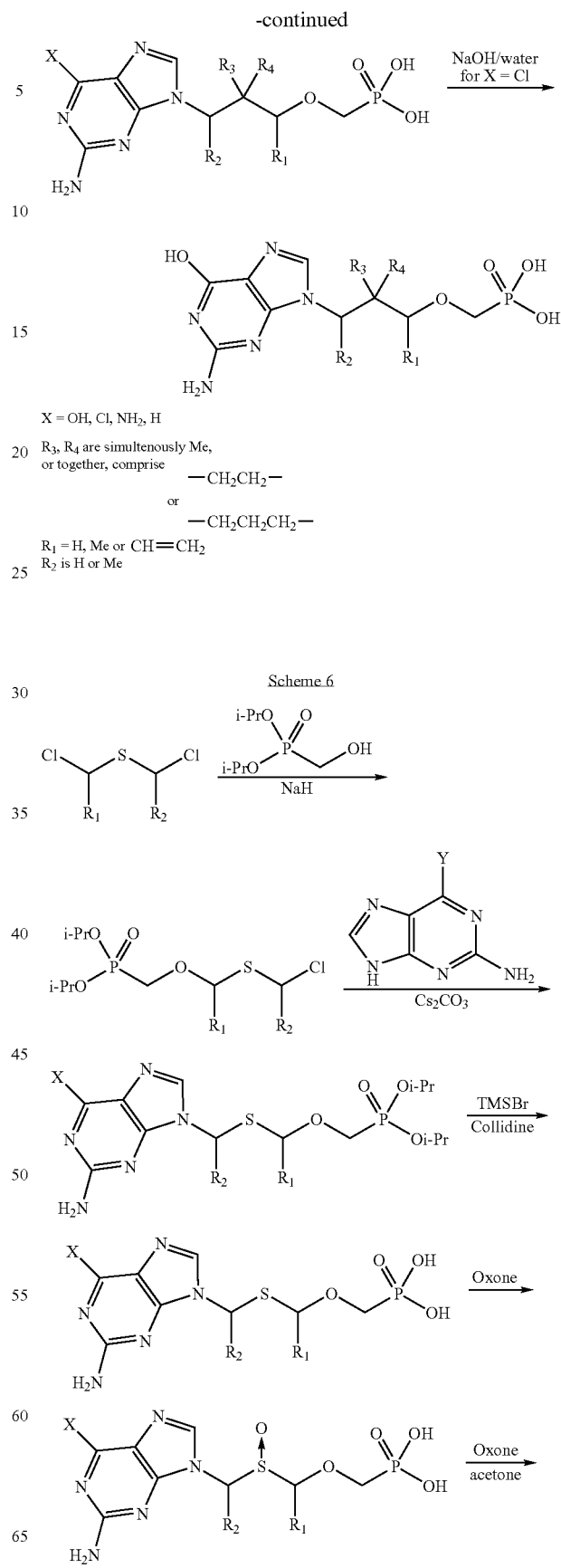

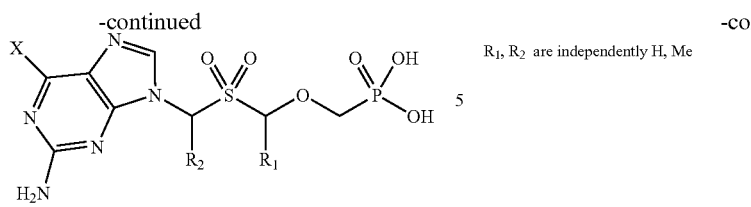
R<sub>1</sub>, R<sub>2</sub> are independently H, Me
Scheme 7
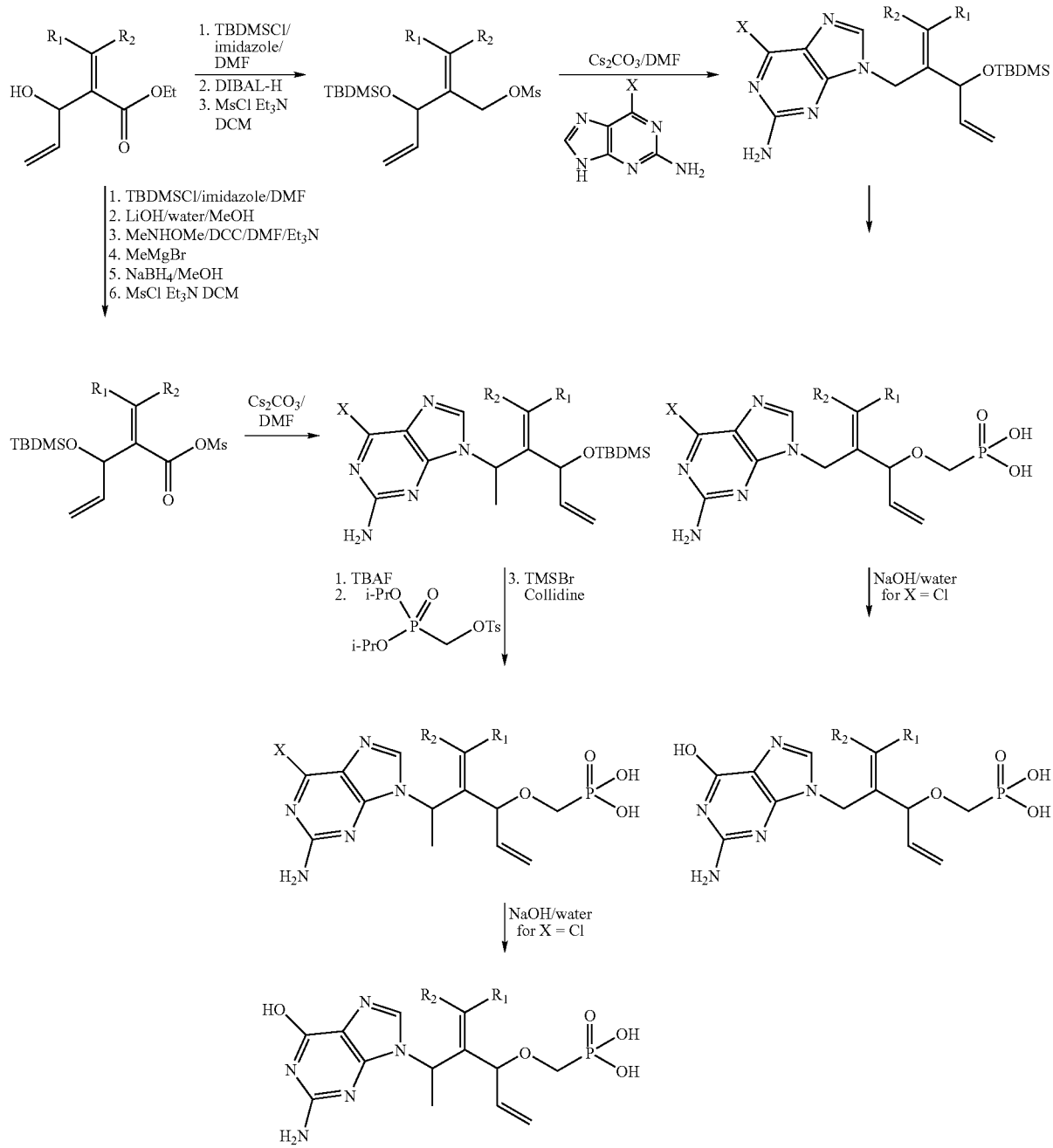
R<sub>1</sub>, R<sub>2</sub>, R<sub>3</sub>, R<sub>4</sub> are independently H, Me
Stereoisomers are separated using chiral chromatography Scheme 8
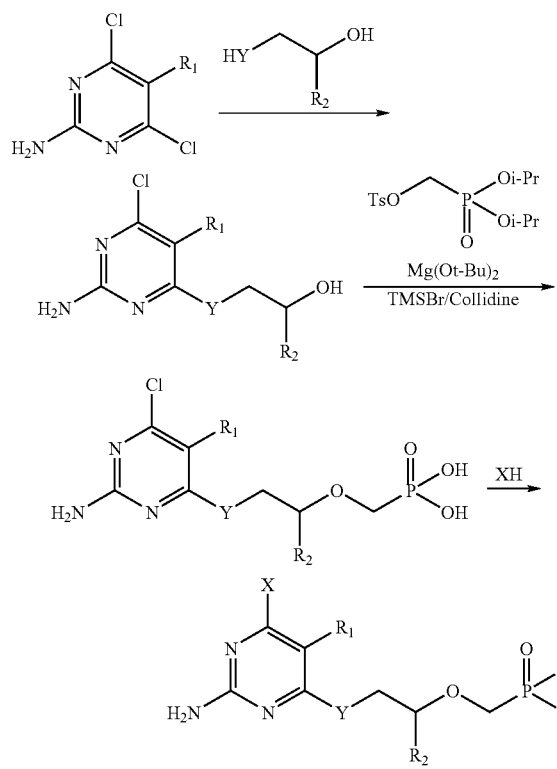
X = OH, OMe, SH, SMe, OCH₂CH₂CN, OCH₂CH₂SSMe
Y = O, NH, NMe, S, SO, SO₂
R₁ = H, Me, CH=CH₂, C(triplebond)CH
R₂ = H, Me, CH=CH₂, F R and S isomers
Scheme 9
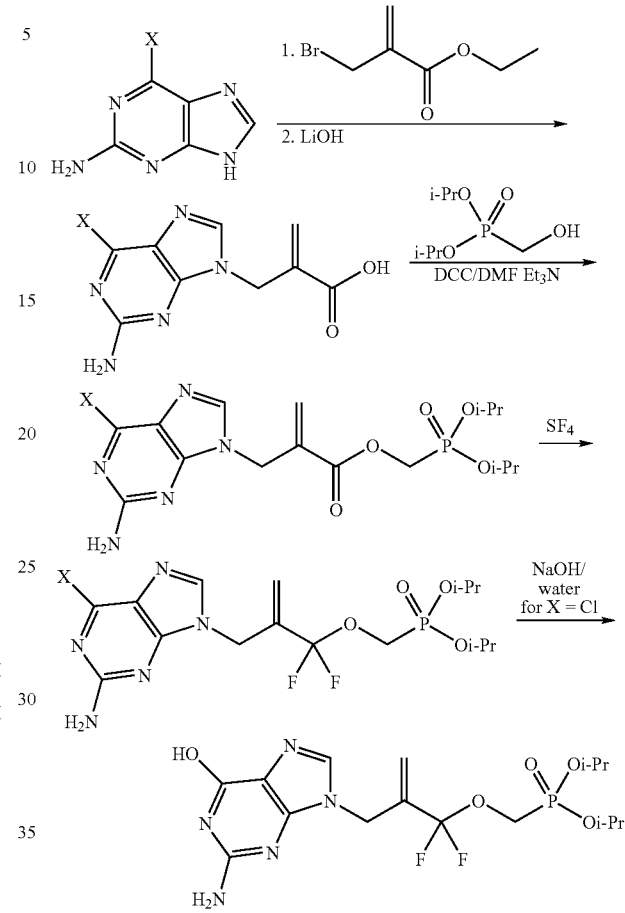
Scheme 10
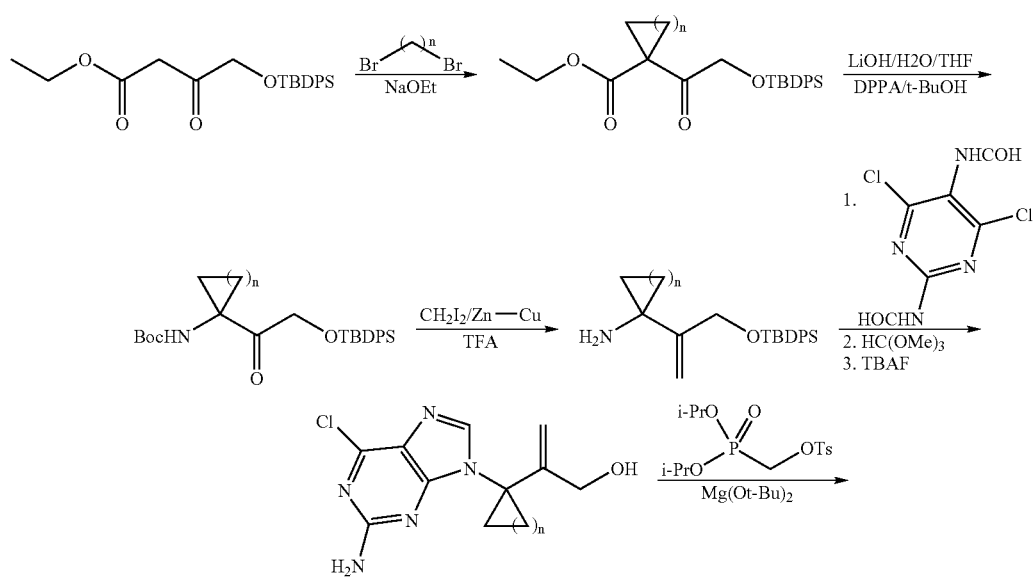

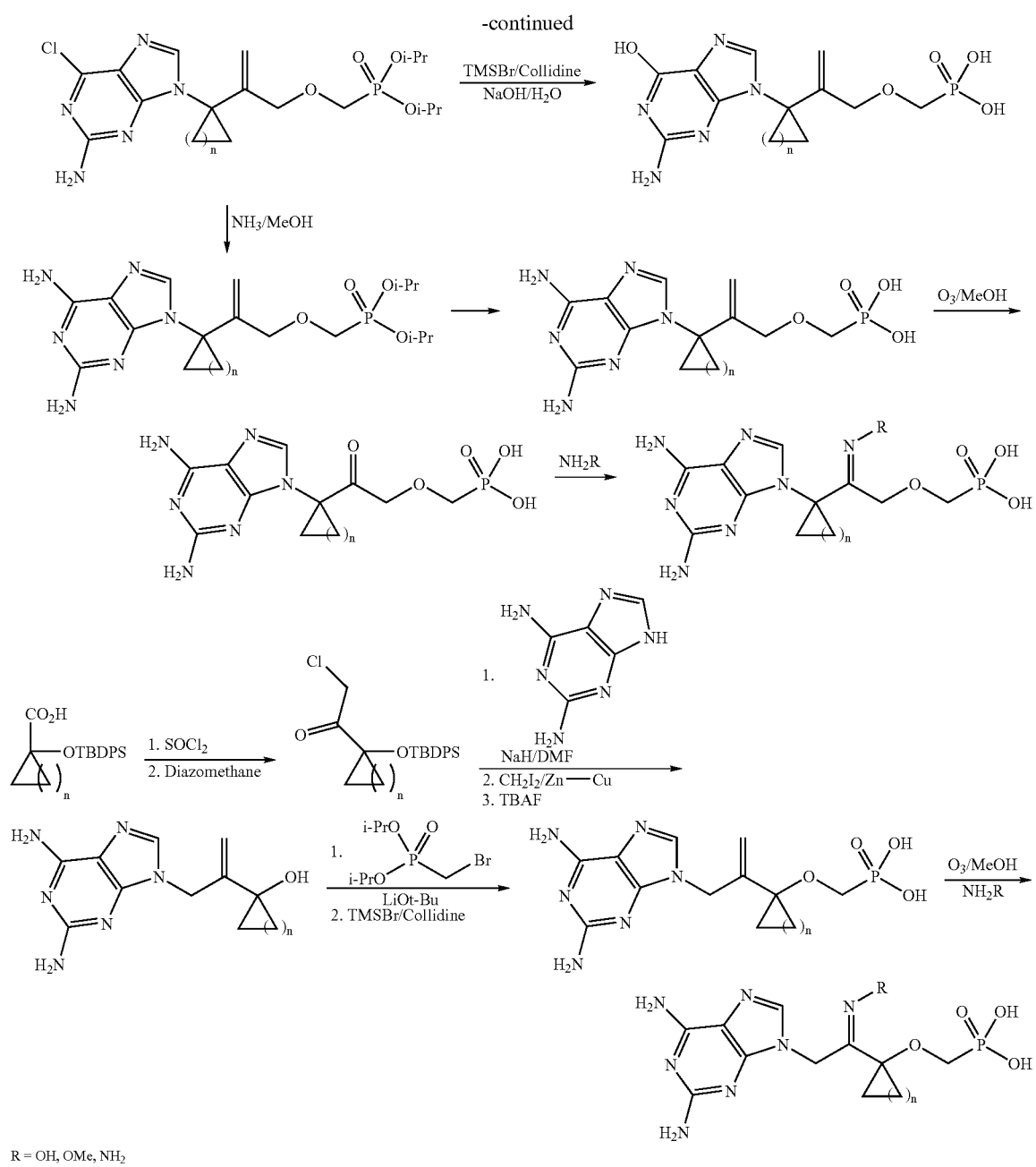
R = OH, OMe, NH$_2$
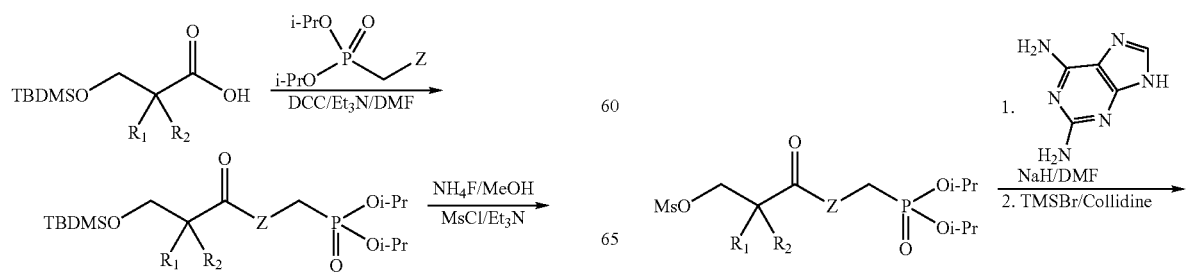
Scheme 11

-continued

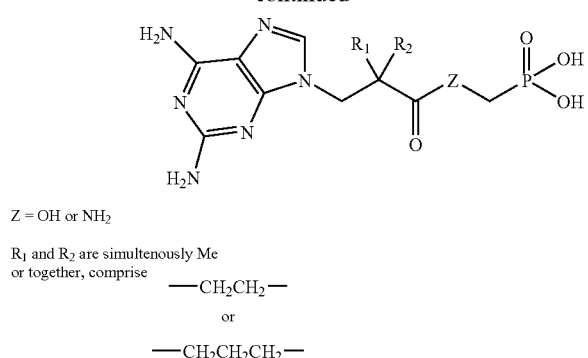

Z = OH or NH₂

R₁ and R₂ are simultenously Me
or together, comprise
—CH₂CH₂—
or
—CH₂CH₂CH₂—

Scheme 12
EXAMPLES: SECTION B

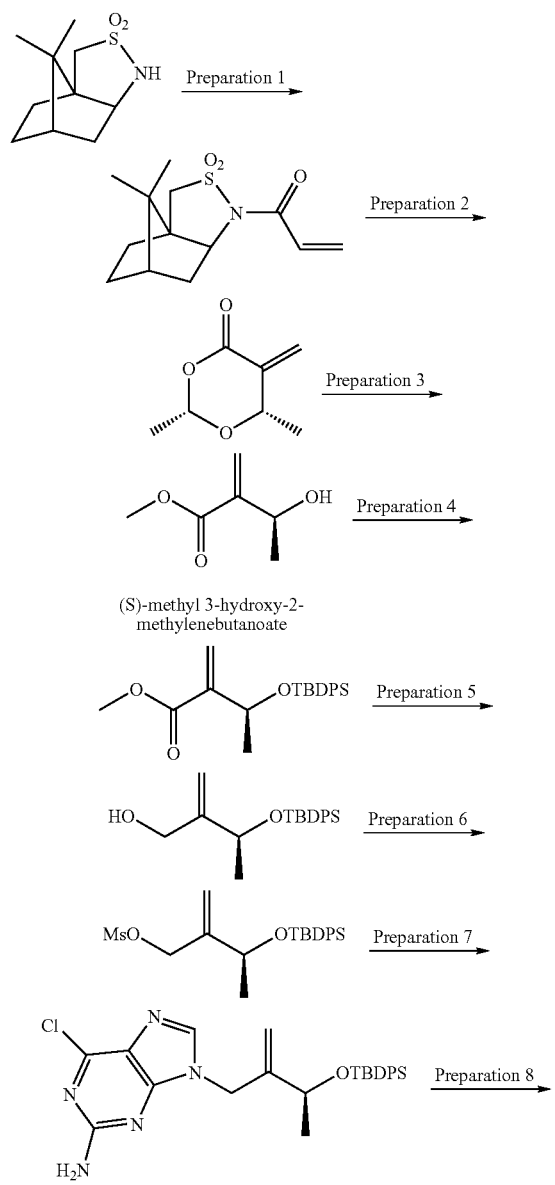

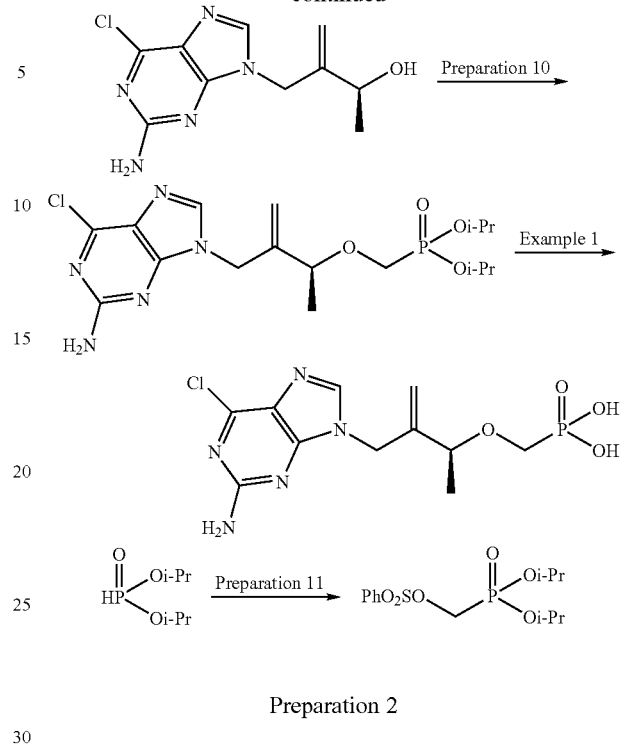

Preparation 2

Synthesis of SDS-1 S-(+)-N-Propenoylbornane-2,10-sultam

The acrylic acid (7.04 mL, 1.2 eq.) bought from Aldrich was dissolved in 120 ml of tetrahydrofuran (THF), 27.5 mL of triethyl amine (TEA) was added thereto and the resulting mixture was cooled to −20° C. To mixture 11.66 mL (1.2 eq.) of pivial chloride was added and stirred for 1 hour. To the reaction mixture add lithium chloride (3.7 g, 1.1 eq.) and bornane 2,10 sultam (17 g, 1 eq.), allow the mixture to warm to RT and stir another 4-6 hours. Reaction mixture was quenched with 10 mL 0.2 M hydrochloric acid (2 eq.). The mixture was reduced under vacuum to remove THF. Extract the aqueous mixture with ethyl acetate (EtOAc) washing the combined organic layers with saturated sodium bicarbonate 2× and brine 1×. Dry organic with sodium sulfate and concentrate in a large flask under reduced pressure to a dry solid. Dissolve the solid in minimum amount of toluene and add hexane until cloudy. Place mixture in freezer overnight. Filter solid rinsing with hexane. Re-concentrate the solution and repeat crystallization for second batch of crystals. Recovered 13.4 g (63% yield) of the title compound, both as a white solid. ¹H NMR(CDCl₃) δ 0.99 (s, 3H), 1.34 (s, 3H), 1.40 (m, 2H), 1.59 (s, 2H), 1.92 (m, 3H), 2.12 (m, 2H), 3.5 (m, 2H), 3.96 (m, 1H), 5.87 (m, 1H), 6.51 (m, 1H), 6.87 (m, 1H)

Preparation 2

Synthesis of SDS-2 (2S,6S)-2,6-dimethyl-5-methylene-1,3-dioxan-4-one

The compound prepared in Preparation 1 (13.4 g) was dissolved in 65 mL of dichloromethane (DCM). The resulting solution was cooled to 0° C. using chiller. Methyl acrylate (41.49 mL, 14.5 eq.) and DABCO (2.74 mg, 0.5 eq) was added to the cold mixture. The solution was stirred over the weekend at 0° C. The mixture was concentrated under reduced pressure and purified by flash column chromatography to provide 6 g (86% yield) of the title compound as a colorless oil. $^1$H NMR(CDCl$_3$) δ 1.48 (m, 6H), 4.64 (m, 1H), 5.50 (m, 1H), 5.59 (d, 1H), 6.49 (d, 1H); and ESI 142.8 (M+1)$^+$, C$_7$H$_{10}$O$_3$ Preparation 3

Synthesis of SDS-3 (S)-methyl 3-hydroxy-2-methylenebutanoate

The compound prepared in Preparation 2 (6 g) was dissolved in 200 mL methanol and 24 mL of TEA was added. The resulting mixture was warmed to 45° C. and stirred until done by TLC (about 10-30 minutes). The mixture was concentrated under vacuum and used crude in the next reaction. Recovered 5.3 g (100+% yield) of unpurified title compound as an oil. ESI 130.8 (M+1)$^+$, C$_6$H$_{10}$O$_3$ Preparation 4

Synthesis of SDS-4 (S)-methyl 3-(tert-butyldiphenylsilyloxy)-2-methylenebutanoate The compound prepared in Preparation 3 (5.3 g) was dissolved in 200 mL dimethyl foramide and cooled to 0° C. Imidazole (2.99 g, 1.1 eq.) was added and the mixture was allowed to stir for 10 minutes. Finally, TBDPSiCl (I 1.26 mL, 1.1 eq.) was slowly added and allowed to warm to RT stirring until done by TLC (about 2 hours). Partition the solution between ether and water. Extract 2× with ether, drying the organic layer with sodium sulfate and concentrating under vacuum. The residue was purified by flash column chromatography eluting with 40% DCM/Hexane. Recovered 6.3 g (43% yield) of the title compound as a colorless oil. ESI 391.1 (M+22)$^+$, C$_{22}$H$_{28}$O$_3$Si Preparation 5

Synthesis of SDS-5 (S)-3-(tert-butyldiphenylsilyloxy)-2-methylenebutan-1-ol

The compound prepared in Preparation 4 (6.3 g) was dissolved in 60 ml of DCM and cooled to −78° C. DiBAL (65 mL, 3.8 eq.) was slowly added to the mixture and stirred for 3-5 hours. The reaction was quench with addition of methanol and 50 mL of a saturated solution of Rochelle's salt was added and allowed to stir at RT for 30 min to an hour. Extract 2× with ether, dry with sodium sulfate, and concentrate under vacuum. Purify the residue by flash column chromatography eluting with 10% EtOAc/hexane. Recovered 2.7 g (yield 47%) of the title compound as a clear oil. $^1$H NMR(DMSO-d) δ 1.00 (s, 6H), 1.08 (d, 3H), 3.95 (d, 2H), 4.34 (m, 1H), 4.75 (t, 1H), 5.03 (2H), 7.44 (m, 6H), 7.60 (m, 4H)

Preparation 6

Synthesis of SDS-6 (S)-3-(tert-butyldiphenylsilyloxy)-2-methylenebutyl methanesulfonate The compound prepared in Preparation 5 (996 mg) was dissolved in 200 ml of DCM and 0.81 (2 eq.) TEA was added and the mixture was cooled to <0° C. (brine/ice). Mesyl chloride (0.23 mL, 1 eq.) was added to the mixture and allowed to stir until done by TLC (about 2 hours). Filter the mixture over a plug of silica gel eluting with DCM. Concentrate and use crude in the next reaction. Recovered 519 mg of the crude title compound as a clear oil. $^1$H NMR(DMSO-d) δ 1.00 (s, 6H), 1.12 (d, 3H), 3.14 (s, 3H), 4.38 (m, 1H), 4.74 (m, 2H), 5.21 (s, 1H), 5.28 (s, 1H), 7.44 (m, 6H), 7.60 (m, 4H)

Preparation 7

Synthesis of SDS-7 (R)-9-(3-(tert-butyldiphenylsilyloxy)-2-methylenebutyl)-6-chloro-9H-purin-2-amine 2-Amino-6-chloro purine (421.6 mg, 2 eq.) is suspended in 200 mL DMF followed by cesium carbonate (404 mg, 1 eq.) and the compound prepared in Preparation 6 (519 mg). The mixture is stirred at RT until done by TLC (2-4 hours). Partition between EtOAc and H$_2$O keeping the organic layer. Wash the organic layer 2× with H$_2$O, dry with sodium sulfate, and concentrate under vacuum. Purify residue by flash column chromatography using 50% EtOAc/hexane. Recovered 380 mg (62% yield) of the title compound as a clear, viscous oil. ESI 492.2 (M+1)$^+$, C$_{26}$H$_{30}$ClN$_5$OSi Preparation 8

Synthesis of SDS-8 (R)-3-((2-amino-6-chloro-9H-purin-9-yl)methyl)but-3-en-2-ol

The compound prepared in Preparation 7 (380 mg) was dissolved in 100 mL methanol and 533 mg (large excess) of ammonium fluoride was added. The flask was fitted with a condenser and heated to reflux (about 65° C.) overnight. The solution was diluted with ethyl acetate and filter over a short pad of silica gel. The pad was rinsed with ethyl acetate and a small amount of 5-10% methanol/ethyl acetate. The solution was concentrated to a white solid 75-90% pure. The title compound was used crude in the next reaction. ESI 254.1 (M+1)$^+$, C$_{10}$H$_{12}$ClN$_5$O Preparation 9

Synthesis of SDS-9 (diisopropoxyphosphoryl)methyl benzenesulfonate

A 1-liter round bottom flask containing a 25-mm egg-shaped stir bar is charged with 100 g of diisopropyl phosphite, 18.06 grams of paraformaldehyde, and 8.39 mL of triethyl amine. A 300-mm×12 bore Liedbig condenser is attached and cold water flow is established. The flask is placed into a pre-heated 130-deg. C oil bath and stirring is initiated. An exotherm is noticed within 5 minutes and the reaction is complete by NMR after 30 minutes (check for completeness by NMR before proceeding to the next step, excess phosphite will hinder final workup). 31P NMR was taken in CDCl$_3$ with a sample directly out of the reaction flask giving one major peak at δ 22.848 (starting material is δ 4.526). The mixture is cooled to RT and diluted with 600 mL of toluene and charged with 72.98 mL of benzene sulfonyl chloride. 117.47 mL of triethyl amine is added drop wise by addition funnel. An exotherm will be noticed and an ice bath should be kept near by to quench out of control exotherms. Reaction mixture was stirred for 1-2 hours at RT and monitored by 31 P NMR watching for appearance of δ 13.066). Upon completion, the mixture was diluted with 200-mL ether and filtered over a short pad of silica gel eluting further with 250 mL EtOAc. Mixture is concentrated until a small amount of toluene is left in flask (about 100 mL overall volume). Product can be crystallized by addition of 100 mL of EtOAc followed by addition of hexane until cloudy and place in freezer or can be rotated and allowed to cool on rotovap to quickly form small crystals.

Crystals were filtered and rinsed with hexane. Recovered the title compound as small white/clear needles 135 g first batch, 17 g from second crystallization in an over all 75% yield. ESI 336.8 (M+1)$^+$, $C_{13}H_{21}O_6PS$ Preparation 10

Synthesis of SDS-10 (R)-diisopropyl (3-((2-amino-6-chloro-9H-purin-9-yl)methyl)but-3-en-2-yloxy)methylphosphonate The compound prepared in Preparation 8 (300 mg) was dissolved in 200 mL DMF. Magnesium t-butoxide (200 mg, 2 eq.) and the compound prepared in Preparation 9 (595.6 mg, 1.5 eq.) were added to the mixture. The mixture was stirred at 70-75° C. until done by TLC (about 2 hours). The excess base was quenched with 10% acetic acid in water. Carefully extract 2× with EtOAc (make sure product removed), dry with sodium sulfate, and concentrate under vacuum. Purify the residue by flash column chromatography eluting with 0-10% methanol/EtOAc. Recovered 220 mg (43% yield) of the title compound as a clear, viscous oil. ESI 432.1 (M+1)$^+$, $C_{17}H_{27}ClN_5O_4P$ Example 1

Synthesis of SDS-11 (R)-(3-((2-amino-6-chloro-9H-purin-9-yl)methyl)but-3-en-2-yloxy)methylphosphonic acid The compound prepared in preparation 10 (220 mg) was dissolved in 100 mL of acetonitrile. 2,3,4-collidine (1.01 ml, 15 eq.) and trimethyl silyl bromide (TMSBr) (0.67 mL, 10 eq.) was added to the mixture and allowed to stir overnight. Concentrate the mixture under vacuum to remove excess HBr/TMSBr. Basify the residue with saturated sodium bicarbonate and extract 2× with ether. Concentrate the aqueous layer and acidify the residue to pH 5-6 with 10% acetic acid/H$_2$O and purify by reverse phase HPLC using a 2 inch phenomenex synerigi polar RP column with a 0-100% acetonitrile/H$_2$O gradient. Recovered 80 mg (45% yield) of the title compound as a white solid. $^1$H NMR(D$_2$O) δ 1.18 (d, 3H), 3.21 (m, 1H), 3.36 (m, 1H), 4.01 (m, 1H), 4.49 (s, 1H), 4.70 (m, 1H), 5.09 (s, 1H), 8.07 (s, 1H); $^{31}$P NMR(D$_2$O) δ 13.96; and ESI 346.3 (M−1)$^−$, $C_{11}H_{15}ClN_5O_4P$ Example 2a Synthesis of SDS-12 (R)-(3-((2-amino-6-oxo-1,6-dihydropurin-9-yl)methyl)but-3-en-2-yloxy)methylphosphonic acid The compound prepared in Example 1 (22 mg) was dissolved in 10 mL of 1 N freshly prepared sodium hydroxide in water. The solution was stirred at 60° C. until done by LC-MS (about 2 hours). The mixture was acidified to pH 5-6 with 10% acetic acid/H$_2$O and concentrated to a less than 5 mL. The solution was purified by reverse phase HPLC using a 2 inch phenomenex synerigi polar RP column with a 0-100% acetonitrile/H$_2$O gradient. Recovered about 5 mg of the title compound as a white solid. $^1$H NMR(D$_2$O) δ 1.19 (d, 3H), 3.34 (m, 1H), 3.46 (m, 1H), 4.02 (m, 1H), 4.51 (s, 1H), 4.60 (s, 2H), 5.09 (s, 1H), 7.70 (s, 1H); $^{31}$P NMR(D$_2$O) δ 15.77; and ESI 328.4 (M−1)$^−$, $C_{11}H_{16}N_5O_5P$ Example 2b Synthesis of SDS-13 (R)-(3-((2,6-diamino-9H-purin-9-yl)methyl)but-3-en-2-yloxy)methylphosphonic acid The compound prepared in Example 1 (15.5 mg) was dissolved in 5 ml of methanol in a 40 ml EPA vial and cooled to −78° C. Ammonia was bubbled in to the reaction doubling until the volume was doubled. The vial was placed in a Parr Bomb and sealed. The bomb was heated at 100° C. for 24 hours (pressure maxed out at 250 psi). The bomb was cooled and opened. The vial contained only solid which was dissolved in 10% acetic acid and water (to a pH of 5). The solution was purified by reverse phase HPLC using a 2 inch phenomenex synerigi polar RP column with a 0-100% acetonitrile/H$_2$O gradient. Recovered about 5 mg of the title compound as a white solid. $^1$H NMR(D$_2$O) δ 1.16 (d, 3H), 3.25 (m, 1H), 3.37 (m, 1H), 3.98 (m, 1H), 4.44 (s, 1H), 4.60 (s, 2H), 5.05 (s, 1H), 7.73 (s, 1H); $^{31}$P NMR(D$_2$O) δ 14.64; and ESI 327.4 (M−1)$^−$, $C_{11}H_{17}N_6O_4P$

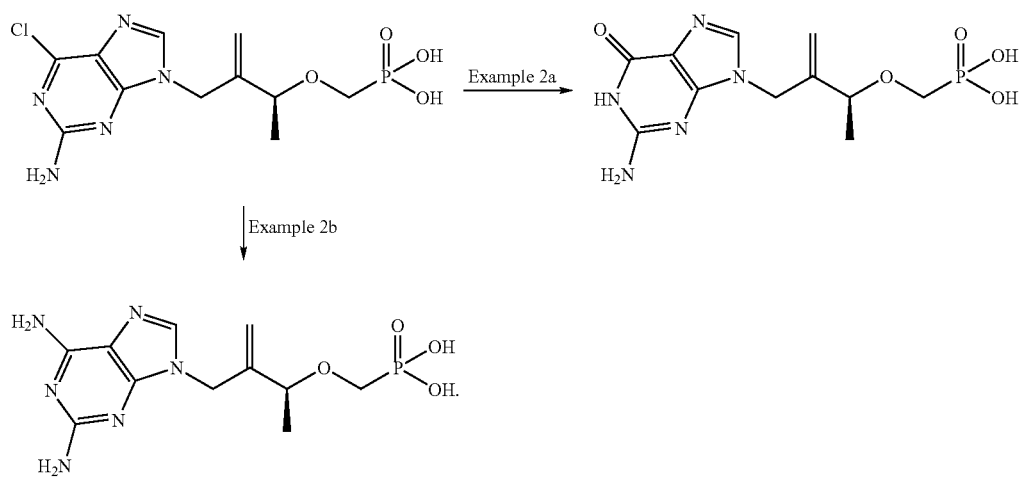

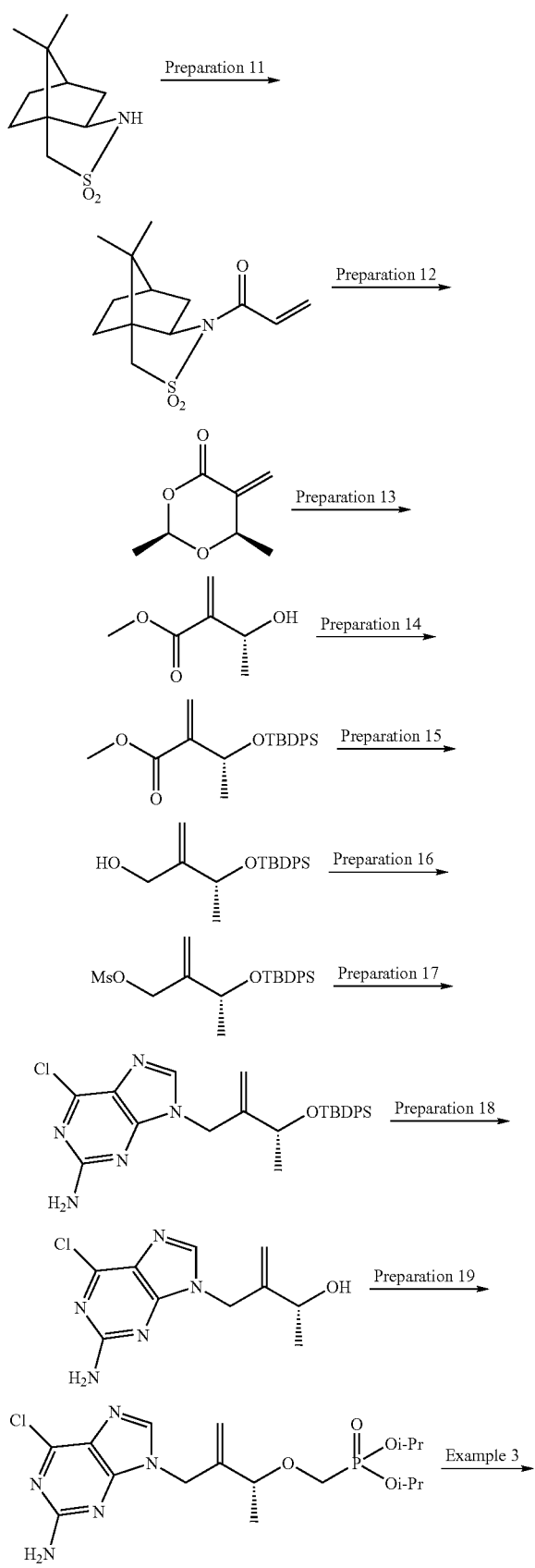

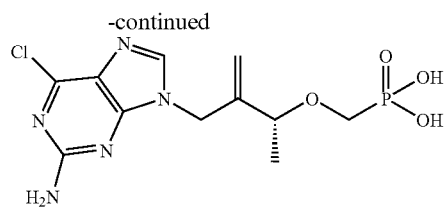

Preparation 11

Synthesis of SDS-14
R-(−)—N-Propenoylbornane-2,10-sultam

The title compound was prepared according to the same procedure as Preparation 1 to give 14 g (yield 56%) of the title compound as a white crystalline solid.

Preparation 12

Synthesis of SDS-15 (2R,6R)-2,6-dimethyl-5-methylene-1,3-dioxan-4-one

The compound prepared in Preparation 11 (14 g) was reacted according to the same procedure as Preparation 12 to give 3.6 g (49% yield) of title compound as a clear oil. ESI 142.8 (M+1)$^+$, $C_7H_{10}O_3$ Preparation 13

Synthesis of SDS-16 (R)-methyl 3-hydroxy-2-methylenebutanoate

The compound prepared in Preparation 12 (3.5 g) was reacted according to the same procedure as Preparation 3 to give 3.4 g of the title compound as a crude mixture. ESI 130.8 (M+1)$^+$, $C_6H_{10}O_3$ Preparation 14

Synthesis of SDS-17 (R)-methyl 3-(tert-butyldiphenylsilyloxy)-2-methylene butanoate The compound prepared in Preparation 16 (3.4 g) was reacted according to the same procedure as Preparation 4 to give 5.3 g (53% yield over two steps) of title compound as a clear oil. ESI 391.1 (M+22)$^+$, $C_{22}H_{28}O_3Si$ Preparation 15

Synthesis of SDS-18 (R)-3-(tert-butyldiphenylsilyloxy)-2-methylenebutan-1-ol

The compound prepared in Preparation 14 (5.3 g) was reacted according to the same procedure as Preparation 5 to give 2.3 g (47% yield) of title compound as a clear oil. $^1$H NMR(DMSO-d) δ 1.00 (s, 6H), 1.08 (d, 3H), 3.95 (d, 2H), 4.34 (m, 1H), 4.75 (t, 1H), 5.03 (2H), 7.44 (m, 6H), 7.60 (m, 4H)

Preparation 16

Synthesis of SDS-19 (R)-3-(tert-butyldiphenylsilyloxy)-2-methylenebutyl methanesulfonate The compound prepared in Preparation 15 (996 mg) was reacted according to the same procedure as Preparation 6 to give 1.139 g of title compound as a crude mixture.

Preparation 17

Synthesis of SDS-20 (S)-9-(3-(tert-butyldiphenylsilyloxy)-2-methylenebutyl)-6-chloro-9H-purin-2-amine The compound prepared in Preparation 16 (1.139 g) was reacted according to the same procedure as Preparation 7 to give 800 mg (60% yield) of title compound as a clear oil. ESI 492.2 (M+1)$^+$, $C_{26}H_{30}ClN_5OSi$

Preparation 18

Synthesis of SDS-21 (S)-3-((2-amino-6-chloro-9H-purin-9-yl)methyl)but-3-en-2-ol The compound prepared in Preparation 17 (700 mg) was reacted according to the same procedure as Preparation 8 to give 600 g of title compound as an approximately 80% pure crude mixture. ESI 254.1 (M+1)$^+$, $C_{10}H_{12}ClN_5O$

Preparation 19

Synthesis of SDS-22 (S)-diisopropyl (3-((2-amino-6-chloro-9H-purin-9-yl)methyl)but-3-en-2-yloxy)methylphosphonate The compound prepared in Preparation 18 (600 mg) was reacted according to the same procedure as Preparation 10 to give 240 mg (yield 39% two steps) of the title compound as clear oil. ESI 432.1 (M+1)$^+$, $C_{17}H_{27}ClN_5O_4P$

Example 3

Synthesis of SDS-23 (S)-(3-((2-amino-6-chloro-9H-purin-9-yl)methyl)but-3-en-2-yloxy)methylphosphonic acid The compound prepared in Preparation 19 (240 mg) was reacted according to the same procedure as Example 1 to give 120 mg (yield 62%) of title compound as a white solid. $^1$H NMR(D$_2$O) δ 1.18 (d, 3H), 3.21 (m, 1H), 3.35 (m, 1H), 4.01 (m, 1H), 4.49 (s, 1H), 4.70 (m, 1H), 5.09 (s, 1H), 8.07 (s, 1H); $^{31}$P NMR(D$_2$O) δ 13.78; and ESI 346.3 (M−1)$^-$, $C_{11}H_{15}ClN_5O_4P$

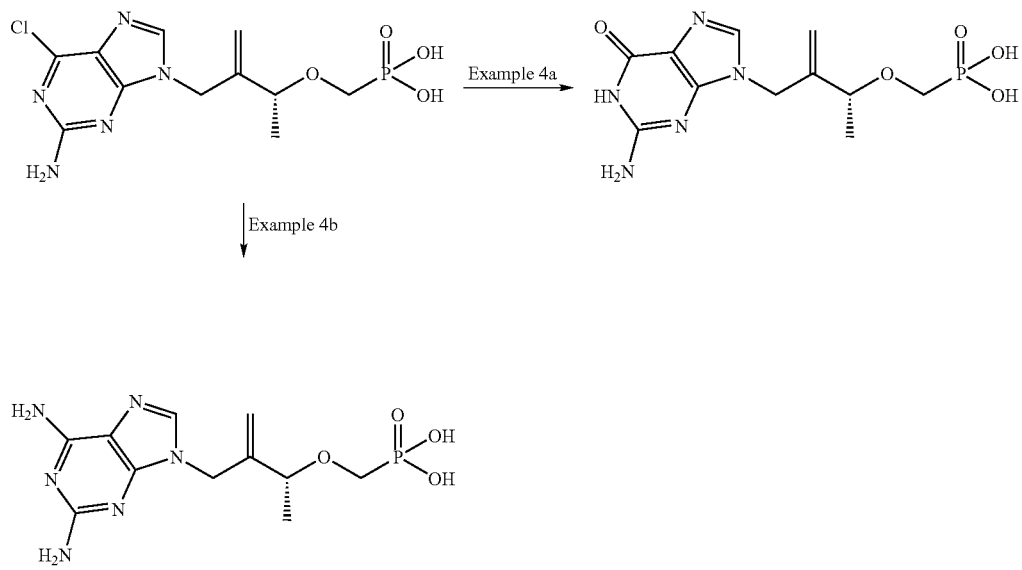

Example 4a

Synthesis of SDS-24 (S)-(3-((2-amino-6-oxo-1,6-dihydropurin-9-yl)methyl)but-3-en-2-yloxy)methylphosphonic acid The compound prepared in Example 3 (23.7 mg) was reacted according to the same procedure as Example 2a to give 3 mg (13% yield) of title compound as a white solid. $^1$H NMR(D$_2$O) δ 1.19 (d, 3H), 3.33 (m, 1H), 3.45 (m, 1H), 4.01 (m, 1H), 4.49 (s, 1H), 4.58 (s, 2H), 5.08 (s, 1H), 7.69 (s, 1H); $^{31}$P NMR(D$_2$O) δ 15.71; and ESI 328.4 (M−1)$^-$, $C_{11}H_{16}N_5O_5P$

Example 4b

Synthesis of SDS-25 (S)-(3-((2,6-diamino-9H-purin-9-yl)methyl)but-3-en-2-yloxy)methylphosphonic acid The compound prepared in Example 3 (22.5 mg) was reacted according to the same procedure as Example 2b to give 3 mg (14% yield) of the title compound as a white solid.

$^1$H NMR(D$_2$O) δ 1.17 (d, 3H), 3.23 (m, 1H), 3.36 (m, 1H), 3.98 (m, 1H), 4.42 (s, 1H), 4.58 (s, 2H), 5.04 (s, 1H), 7.72 (s, 1H); $^{31}$P NMR(D$_2$O) δ 14.41; and ESI 327.4 (M−1)$^-$, C11H17N6O4P

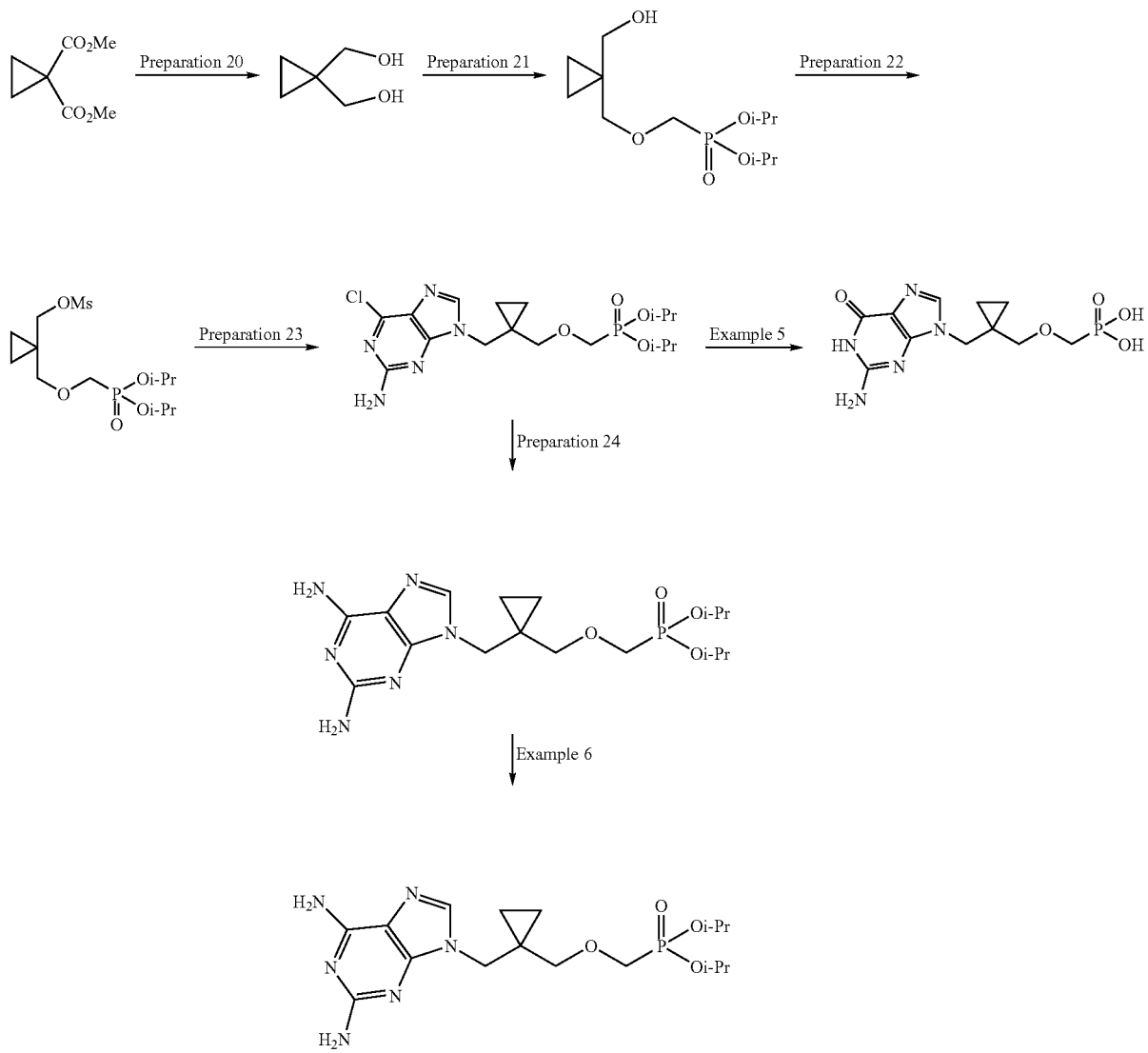

Preparation 20

Synthesis of SDS-26 2,2-cyclopropane-1,3-propanol

The title compound was prepared by dissolving dimethyl cyclopropane-1,1-dicarboxylate (10 g, 1 eq.) in 250 mL THF and cooling the mixture to 0° C. To the cooled and stirred mixture 126.5 (2 eq.) of lithium aluminum hydride (LAH) as a 1 M solution in THF was added. The mixture was heated at reflux for 16 hours. The mixture was cooled to 0° C. and quench with a small portion of H$_2$O followed by a small amount of 15% sodium hydroxide along with additional water and stirred three hours. Filter through glass sintered funnel, rinsing with THF. The solution was concentrated to a clear oil. The title compound was recovered in a 48% yield (3.095 g).

Preparation 21

Synthesis of SDS-27 diisopropyl ((1-(hydroxymethyl)cyclopropyl)methoxy) methylphosphonate The compound prepared in Preparation 20 (1.8 g) was reacted according to the same procedure as Preparation 10 to give 2 g of an approximate 50% yield of title compound as a crude mixture. ESI 281.1 (M+1)$^+$, $C_{12}H_{25}O_5P$ Preparation 22

Synthesis of SDS-28 (1-(((diisopropoxyphosphoryl)methoxy)methyl)cyclopropyl) methyl methanesulfonate The compound prepared in Preparation 21 (2 g crude) was reacted according to the same procedure as Preparation 6 to give 2 g of the title compound as a crude mixture. ESI 359.1 (M+1)$^+$, $C_{13}H_{27}O_7PS$ Preparation 23

Synthesis of SDS-29 diisopropyl ((1-((2-amino-6-chloro-9H-purin-9-yl)methyl) cyclopropyl)methoxy) methylphosphonate The title compound was prepared by cooling 50 mL NMP to 0° C. and slowly suspending 57 mg (2 eq.) sodium hydride followed by addition of 2-amino-6-chloropurine and stirring for 10-15 minutes. The compound prepared in Preparation 22 (267 mg) was added to the cooled, stirring solution. The mixture was then heated at 100° C. for 1 hour. The reaction was carefully quench with H$_2$O and acetic acid/H$_2$O, concentrated, diluted in DMF/H$_2$O and purified on the HPLC using a Phenomenex Synergi Polar RP column running a 0-100% acetonitrile/water over 20 minutes. Recovered 50 mg of the title compound as a clear oil. ESI 432.2 (M+1)$^+$, $C_{17}H_{27}ClN_5O_4P$ Example 5

Synthesis of SDS-30 ((1-((2-amino-6-oxo-1,6-dihydropurin-9-yl)methyl)cyclopropyl) methoxy)methylphosphonic acid The compound prepared in Preparation 23 (50 mg) was dissolved in 50 mL of acetonitrile. Trimethyl silyl bromide (TMSBr) (0.5 mL) was added to the mixture and allowed to stir overnight. Water was added to the mixture and stirred for another 2 hours. Basify the residue with saturated sodium bicarbonate. Concentrate and acidify the residue to pH 5-6 with 10% acetic acid/H$_2$O and purify by reverse phase HPLC using a 2 inch phenomenex synerigi polar RP column with a 0-20-100 acetonitrile/H$_2$O gradient each with 1% acetic acid, over 0-7-13-15 minutes (retention 14 minutes). Recovered 5 mg of the title compound as a white solid. ESI 330.2 (M−1)$^-$, $C_{11}H_{16}N_5O_5P$ Preparation 24

Synthesis of SDS-31 diisopropyl ((1-((2,6-diamino-9H-purin-9-yl)methyl) cyclopropyl)methoxy)methylphosphonate The compound prepared in Preparation 22 (109 mg) was reacted according to the same procedure as Preparation 23 (using 2,6-diaminopurine instead of 2-amino-6-chloropurine) to give 50 mg of the title compound as a mixture of mono and bis isopropyl phosphonate. ESI 371.2 (M+1)$^+$, C17H29N6O4P Example 6

Synthesis of SDS-32 ((1-((2,6-diamino-1,6-dihydropurin-9-yl)methyl)cyclopropyl) methoxy)methylphosphonic acid The compound prepared in Preparation 24 (50 mg) was reacted according to the same procedure as Example 1 to give about 2 mg of the title compound as a white solid. ESI 329.3 (M+1)$^-$, $C_{11}H_{17}N_6O_4P$

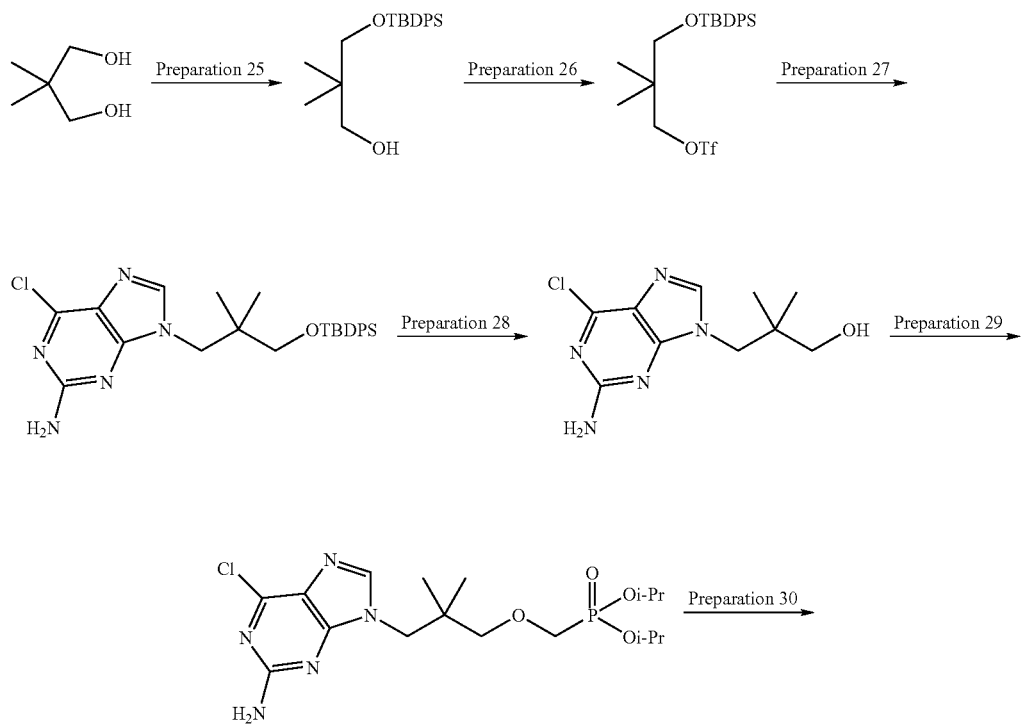

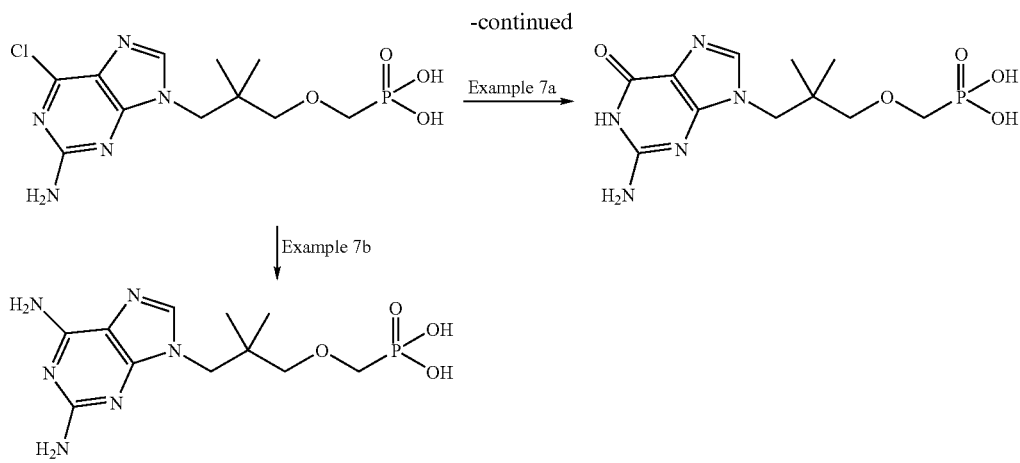

Preparation 25

Synthesis of SDS-33 3-(tert-butyldiphenylsilyloxy)-2,2-dimethylpropan-1-ol

The title compound was prepared using 2.09 g of 2,2-dimethylpropane-1,3-diol diol acquired from Aldrich According to the same procedure as Preparation 4 to give 1.5 g of the title compound as an clear oil. ESI 343.0 (M+1)$^+$, $C_{21}H_{30}O_2Si$

Preparation 26

10 Synthesis of SDS-34 3-(tert-butyldiphenylsilyloxy)-2,2-dimethylpropyl trifluoro methanesulfonate The compound prepared in Preparation 25 (1.5 g) was dissolved in 200 mL DCM. DMAP (1.605 g, 3 eq.) and triflic anhydride (1.48 mL, 1.3 eq.) were added to the solution and allowed to stir about 1 hour (until done by LC-MS). The solution was partitioned between EtOAc and H$_2$O and extracted with EtOAc. The organic layer was dried with sodium sulfate and filtered over a short pad of silica gel eluting with EtOAc. Recovered 6 g of the title compound as a crude, clear oil.

Preparation 27

Synthesis of SDS-35 9-(3-(tert-butyldiphenylsilyloxy)-2,2-dimethylpropyl)-6-chloro-9H-purin-2-amine The title compound was prepared by suspending 2-amino-6-chloropurine in NMP and cooling the mixture to 0° C. Sodium Hydride (600 mg) was added and allowed to stir 30 min. The compound prepared in Preparation 26 (6 g) was added and the mixture was warmed to RT and stirred for 2 hours. Partition the mixture between EtOAc and H$_2$O and extract 2× EtOAc, dry the organic layer with sodium sulfate and concentrate. Purify by flash column chromatography to give 1.9 g (30% yield) of the title compound as a clear oil. ESI 494.3 (M+1)$^+$, $C_{26}H_{32}ClN_5OSi$

Preparation 28

Synthesis of SDS-36 3-(2-amino-6-chloro-9H-purin-9-yl)-2,2-dimethylpropan-1-ol

The compound prepared in Preparation 27 (1.9 g) was reacted according to the same procedure as Preparation 8 to give about 500 mg of the title compound. ESI 256.1 (M+1)$^+$, $C_{10}H_{14}ClN_5O$

Preparation 29

Synthesis of SDS-37 diisopropyl (3-(2-amino-6-chloro-9H-purin-9-yl)-2,2-dimethyl propoxy)methylphosphonate The compound prepared in Preparation 28 (500 mg) was reacted according to the same procedure as Preparation 10 to give 220 mg of the title compound 70% pure. ESI 434.1 (M+1)$^+$, $C_{17}H_{29}ClN_5O_4P$

Preparation 30

Synthesis of SDS-38 (3-(2-amino-6-chloro-9H-purin-9-yl)-2,2-dimethylpropoxy) methylphosphonic acid The compound prepared in Preparation 29 (220 mg) was reacted according to the same procedure as Example 1 to give 80 mg of the title compound as a white solid. ESI 348.5 (M−1)$^-$, $C_{11}H_{17}ClN_5O_4P$

Example 7a

Synthesis of SDS-39 (3-(2-amino-6-oxo-1,6-dihydropurin-9-yl)-2,2-dimethylpropoxy) methylphosphonic acid The compound prepared in Preparation 30 (30 mg) was reacted according to the same procedure as Example 2a to give 1 mg of the title compound as a white solid. $^1$H NMR (D$_2$O) δ 0.71 (2, 6H), 3.06 (2, 2H), 3.35 (m, 2H), 3.81 (s, 2H), 7.71 (br s, 1H); and ESI 330.4 (M−1)$^-$, $C_{11}H_{18}N_5O_5P$

Example 7b
Synthesis of SDS-40 (3-(2,6-diamino-9H-purin-9-yl)-2,2-dimethylpropoxy) methylphosphonic acid
The compound prepared in Preparation 30 (39.2 mg) was reacted according to the same procedure as Example 2b to give 1 mg of the title compound as a white solid. $^1$H NMR ($D_2O$) δ 0.74 (s, 6H), 3.08 (s, 2H), 3.42 (br s, 2H), 3.84 (s, 2H), 7.75 (br s, 1H); and ESI 329.6 (M−1)$^-$, $C_{11}H_{19}N_6O_4P$
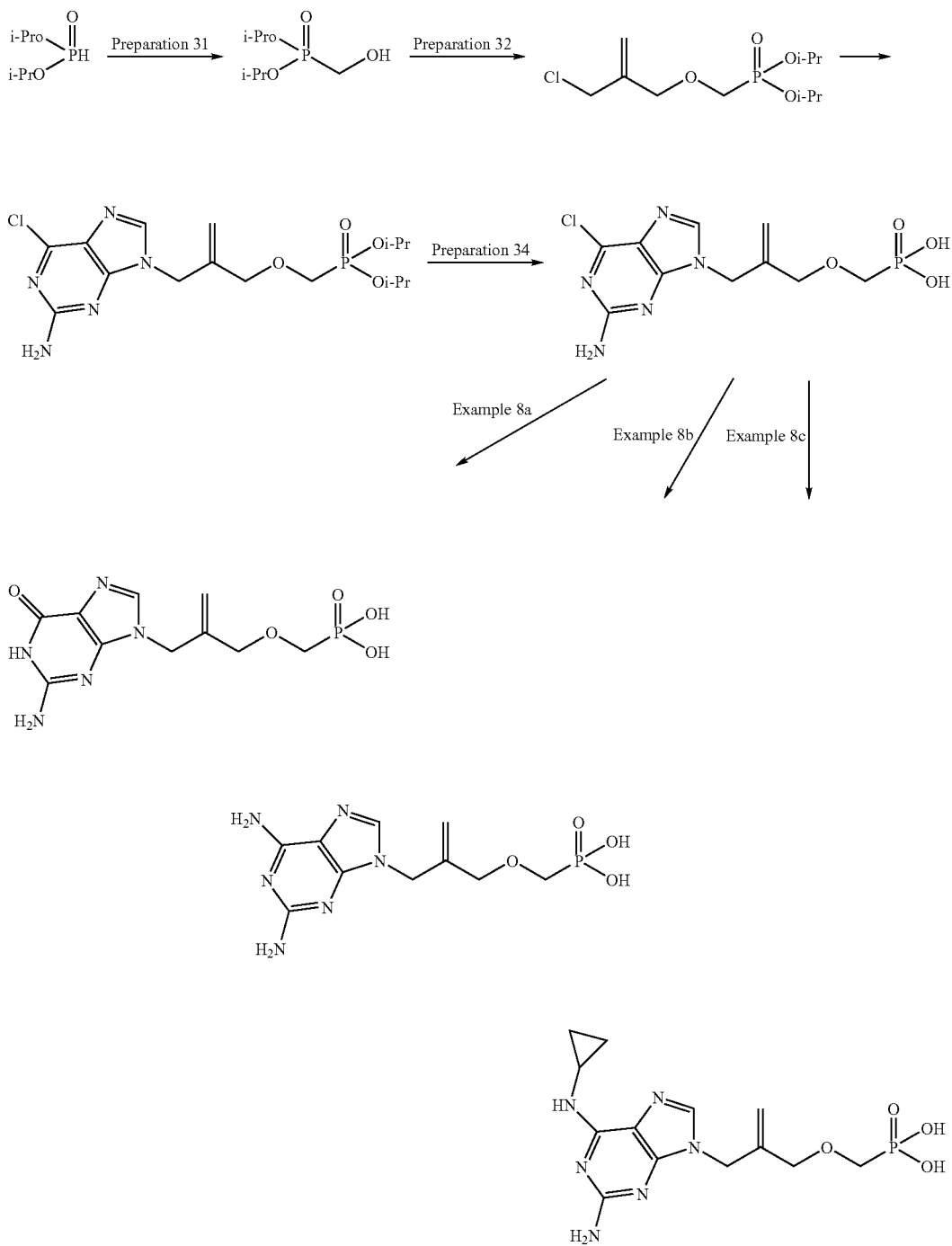

Preparation 31

Synthesis of diisopropyl hydroxymethylphosphonate

To a suspension of paraformaldehyde (3.4 g) in diisopropylphosponate (25 g) was added triethylamine (2 mL). The reactants were heated in a 130° oil bath with vigorous stirring for 4 h. The volatiles were removed on a rotavap and the residue was chromatographed on silica gel using ethyl acetate to afford 19.3 g of material. $^1$H NMR(DMSO-$d_6$) δ 1.23 (d, 12H), 3.62 (dd, 2H), 4.59 (m, 2H), 5.31 (m, 1H)

Preparation 32

Synthesis of diisopropyl chloromethylallyloxymethylphosphonate

A solution of the compound obtained in preparation 31 (6.92 g) in THF (100 mL) was cooled to −78° C. and sodium hydride (931.2 mg) was added in portions. The mixture was the slowly warmed to −20° C. and 2-chloromethyl-3-chloropropene was added. The reaction was stirred at room temperature for 6 h, partitioned between ethyl acetate and water, and the organic layer was evaporated. The residue was chromatographed on silica gel using ethyl acetate/hexanes 1:1 to afford 2.6 g of an oil. $^{31}$P NMR(CD$_3$CN) δ 19.03

Preparation 33

Synthesis of SDS-41 diisopropyl (2-((2-amino-6-chloro-9H-purin-9-yl)methyl) allyloxy)methylphosphonate The compound prepared in Preparation 32 was dissolved in 80 mL DMF. 2-Amino-6-chloro purine (10.3 g, 2.6 eq.) and potassium carbonate (8.5 g, 2.6 eq.) were added to the solution and stirred overnight at RT. Dilute mixture with EtOAc and filter to remove solid. Extract 2× EtOAc and water, wash organic 1× brine, dry sodium sulfate, and concentrate under vacuum. Purified by flash column chromatography (9:1 EtOAc/methanol) where 5-6 grams of compound prepared in Preparation 16 was recovered. The reaction was repeated with a bigger stir bar using recovered materials (8 g purine, 5-6 grams phosphonate) all dissolved in 80 mL DMF. Fresh potassium carbonate (6.5 g) was added and the suspension allowed to stir overnight. Reaction was worked up and purified same as first attempt. Recovered 3.4 g (32.6% yield from original reaction) of the title compound by crystallization with EtOAc/Hex.

Preparation 34

Synthesis of SDS-42 (2-((2-amino-6-chloro-9H-purin-9-yl)methyl)allyloxy) methylphosphonic acid The compound prepared in Preparation 33 (1.98 g) was dissolved in 25 mL acetonitrile. 2,3,4-collidine (9.4 mL, 15 eq.) and TMSBr (6.35 mL, 10 eq.) were added to the stirring mixture and stirred overnight. The mixture was concentrated to remove excess TMSBr and residual acid. A slight excess of sodium bicarbonate (5.6 g in 20 mL of water) was added. Extract 2,3,4-collidine 2× with ether. Acidify aqueous layer carefully with acidic resin to a low pH. Filter and concentrate. Recovered 1.53 g (96% yield) of the title compound as a white solid.

Example 8a

Synthesis of SDS-43 (2-((2-amino-6-oxo-1,6-dihydropurin-9-yl)methyl)allyloxy) methylphosphonic acid The compound prepared in Preparation 34 (212 mg) was reacted according to the same procedure as Example 2a to give the title compound as a white solid.

Example 8b

Synthesis of SDS-44 (2-((2,6-diamino-9H-purin-9-yl)methyl)allyloxy) methyl phosphonic acid The compound prepared in Preparation 34 (1.002 g) was reacted according to the same procedure as Example 2b to give 250 mg of title compound as a white solid. ESI 313.3 (M−1)$^-$, $C_{10}H_{15}N_6O_4P$

Example 8c

Synthesis of SDS-45 (2-((2-amino-6-(cyclopropylamino)-9H-purin-9-yl)methyl) allyloxy)methylphosphonic acid The compound prepared in Preparation 34 (50 mg) was dissolved in 2 mL water and 1.5 mL cyclopropyl amine. The mixture was stirred at 60° C. until done by LC-MS (1 hour). Acidify the solution to pH 5-6 with 10% AcOH/H$_2$O and purify by HPLC on a Phenomenex Synergi column with a 0-0-20-100% MeOH/H$_2$O 0-7-12-15 minute with a 20 mL/minute flow rate. Recovered 5 mg of the title compound as a white solid. ESI 353.4 (M−1)-, $C_{13}H_{19}N_6O_4P$

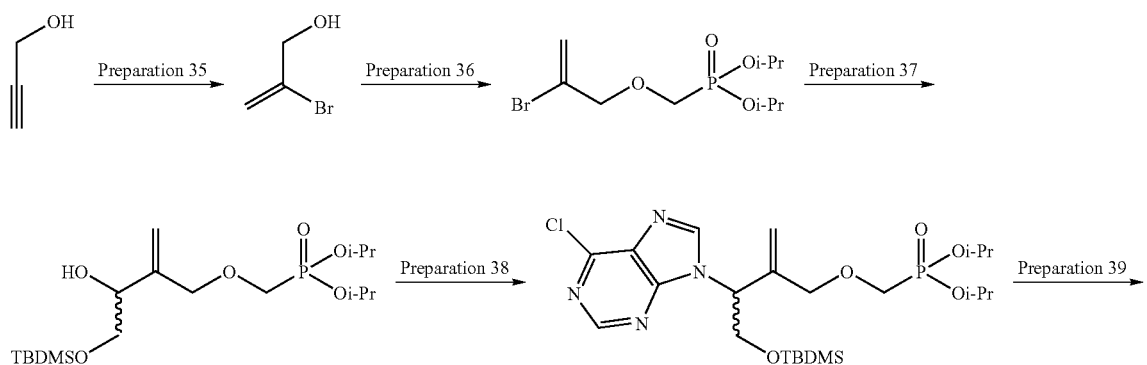

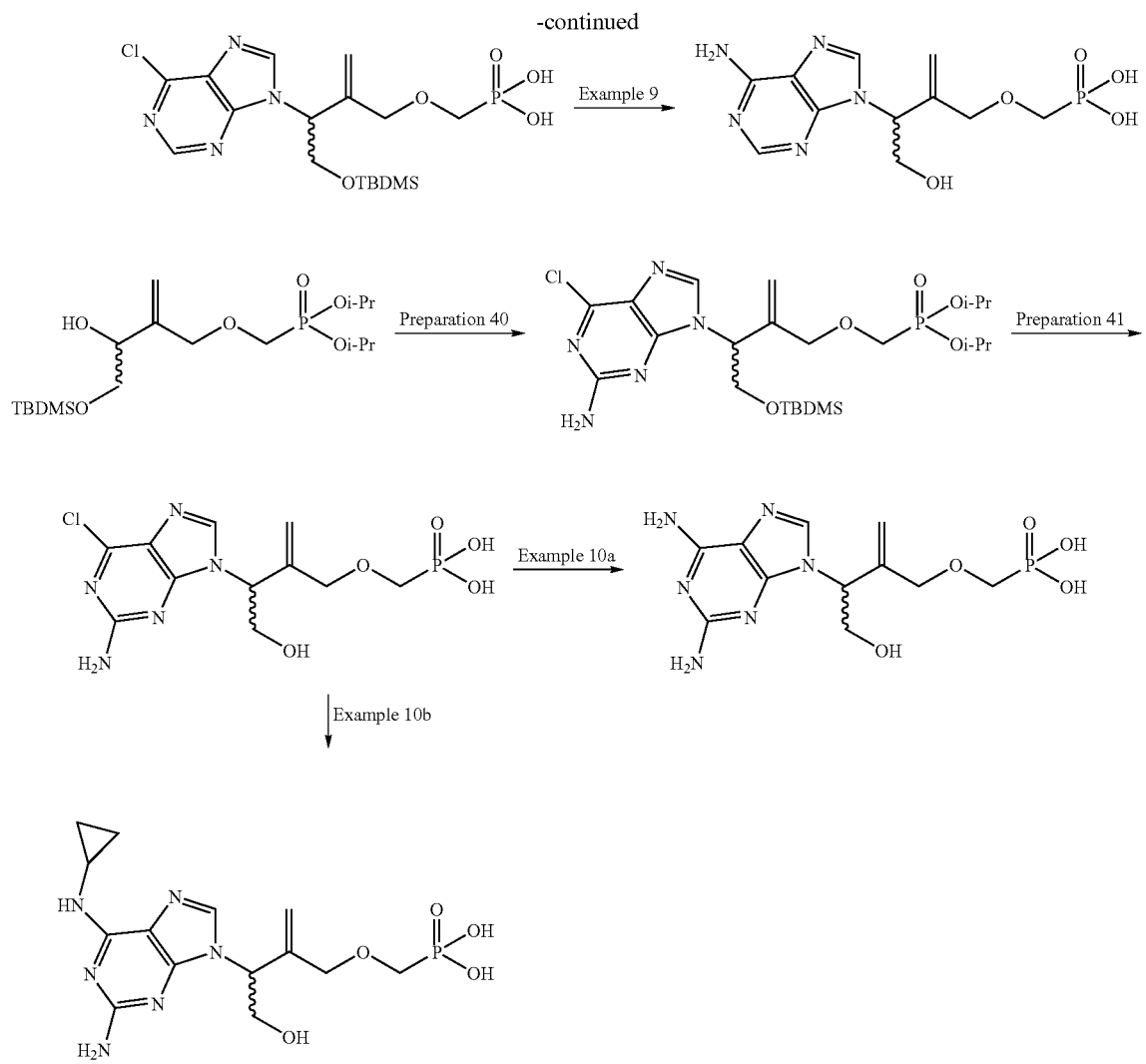

Preparation 35

Synthesis of SD S-46 2-bromoprop-2-en-1-ol

The title compound was made by suspending tetraethyl amino bromide (75 g, 1.1 eq.) in 400 mL DCM. The resulting suspension was cooled to 0° C. and gaseous HBr was bubbled into the reaction until most of the solid dissolved. Propargyl alcohol (19 mL, 1 eq.) was added and the mixture was heated at 40° C. for 4-5 hours or until done by TLC. The mixture was cooled to 0° C. and about 100 mL of ether was added. The crashed out salt was filtered off and the solution was concentrated. The brown oil was distilled to give 18.5 grams (from two batches) of the title compound as a slightly brown oil.

Preparation 36

Synthesis of SDS-47 diisopropyl (2-bromoallyloxy)methylphosphonate

The compound prepared in Preparation 35 (18.5 g) was reacted according to the same procedure as Preparation 10 to give 15 g of the title compound as a slightly yellow oil. ESI 316.9 (M+1)$^+$, $C_{10}H_{20}BrO_4P$

Preparation 37

Synthesis of SDS-48 diisopropyl (4-(tert-butyldimethylsilyloxy)-3-hydroxy-2-methylenebutoxy)methylphosphonate The compound prepared in Preparation 36 (2 g/reaction) was dissolved in 15 mL DMF in a 20 mL microwave vial. 2-(Tert-butyldimethylsilyloxy)acetaldehyde (0.595 mg, 0.5 eq.) and chromium chloride (1.093 g, 1.75 eq.) were quickly added to the solution followed by 32.9 mg (0.1 M %) nickel chloride. The vial was capped and heated in the microwave for a fixed hold time of 2 minutes at 110° C. The cooled solution was quenched with 2 mL of diamino ethane/water solution and stirred for 1 hour (solution turns purple). The mixture was filtered over celite and partitioned between EtOAc and H$_2$O, extracted 2× EtOAc, and dried with sodium sulfate. The solution was filtered over a short pad of silica gel and concentrated. Recovered 3 g (two reactions) of title compound as a crude yellow/green oil. ESI 411.2 (M+1)$^+$, $C_{18}H_{39}O_6PSi$

Preparation 38

Synthesis of SDS-49 diisopropyl (4-(tert-butyldimethylsilyloxy)-3-(6-chloro-9H-purin-9-yl)-2-methylenebutoxy)methylphosphonate The compound prepared in Preparation 37 (750 g) was dissolved in 40 mL dioxane. 6-Amino purine (562.5 g, 3 eq.) and triphenylphospine (954 g, 2 eq.) were added to the solution and 0.7 mL (2 eq.) DIAD was slowly added. The resulting mixture was covered with foil and allowed to stir 3 hours or until done by LC-MS. Partition the mixture in EtOAc and water and extract 2× EtOAc, dry sodium sulfate, and concentrate. Purify by HPLC using a Phenomenx Synergi column and a 0-100-100% MeOH/H$_2$O 0-20-25 minutes. Recovered 200 mg of the title compound as an clear oil. ESI 547.2 (M+1)$^+$, C$_{23}$H$_{40}$ClN$_4$O$_5$PSi

Preparation 39

Synthesis of SDS-50 (3-(6-chloro-9H-purin-9-yl)-4-hydroxy-2-methylenebutoxy) methylphosphonic acid The compound prepared in Preparation 38 (200 mg) was reacted according to the same procedure as Example 1 to give 400 mg of unpurified title compound and salt. ESI 461.3 (M−1)$^-$, C$_{17}$H$_{28}$ClN$_4$O$_5$PSi

Example 9

Synthesis of SDS-51 (3-(6-amino-9H-purin-9-yl)-4-hydroxy-2-methylenebutoxy) methylphosphonic acid The compound prepared in Preparation 39 (200 mg, including salt) was dissolved in 1.5 mL ethanol and 0.5 mL ammonium hydroxide in a 5 mL microwave vial. The mixture was microwaved at 160° C. for 45 minutes. The solution was acidified with 1 N hydrochloric acid and heated at 60° C. for 1 hour. The solution was reduced to less than 5 mL and purified by HPLC using a Phenomenx Synergi column 0-0-20-100% MeOH/H$_2$O 0-7-12-15 minutes at 20 mL a minute. Recovered 5 mg of the title compound as a white solid. ESI 328.4 (M−1)$^-$, C$_{11}$H$_{16}$N$_5$O$_5$P

Preparation 40

Synthesis of SDS-52 diisopropyl (3-(2-amino-6-chloro-9H-purin-9-yl)-4-(tert-butyl dimethylsilyloxy)-2-methylenebutoxy)methylphosphonate The compound prepared in Preparation 37 (750 mg) was reacted according the same procedure as Preparation 4 (using 2-amino-6-chloropurine instead of 6-chloropurine) to give 300 mg of the title compound as a clear oil. ESI 562.3 (M+1)$^+$, C23H41ClN5O5PSi

Preparation 41

Synthesis of SDS-53 (3-(2-amino-6-chloro-9H-purin-9-yl)-4-(tert-butyldimethyl silyloxy)-2-methylenebutoxy)methylphosphonic acid The compound prepared in Preparation 40 (300 mg) was reacted according to the same procedure as Preparation Example 1 to give about 200 mg of unpurified title compound and salt. ESI 476.3 (M−1)$^-$, C$_{17}$H$_{29}$ClN$_5$O$_5$PSi

Example 10a

Synthesis of SDS-54 (3-(2,6-diamino-9H-purin-9-yl)-4-hydroxy-2-methylenebutoxy) methylphosphonic acid The compound prepared in Preparation 41 (100 mg, including salt) was reacted according to Example 9 to give 5 mg of the title compound as a white solid. ESI 343.4 (M−1)$^-$, C$_{11}$H$_{17}$N$_6$O$_5$P

Example 10b

Synthesis of SDS-55 (3-(2-amino-6-(cyclopropylamino)-9H-purin-9-yl)-4-hydroxy-2-methylenebutoxy)methylphosphonic acid The compound prepared in Preparation 41 (100 mg, including salt) was dissolved in 2 mL water and 1.5 mL cyclopropyl amine and heated to 60° C. for 1 hour (or until done by LC-MS). The solution was acidified with 1 N hydrochloric acid and stirred for another hour at 60° C. and concentrated to less than 5 mL. The solution was purified by HPLC using a Phenomenx Synergi column 0- 0-20-100% MeOH/H$_2$O for 0-7-12-15 minutes at a 20 mL/minute flow rate. Recovered 5 mg of the title compound as a white solid. ESI 383.4 (M−1)$^-$, C$_{14}$H$_{21}$N$_6$O$_5$P

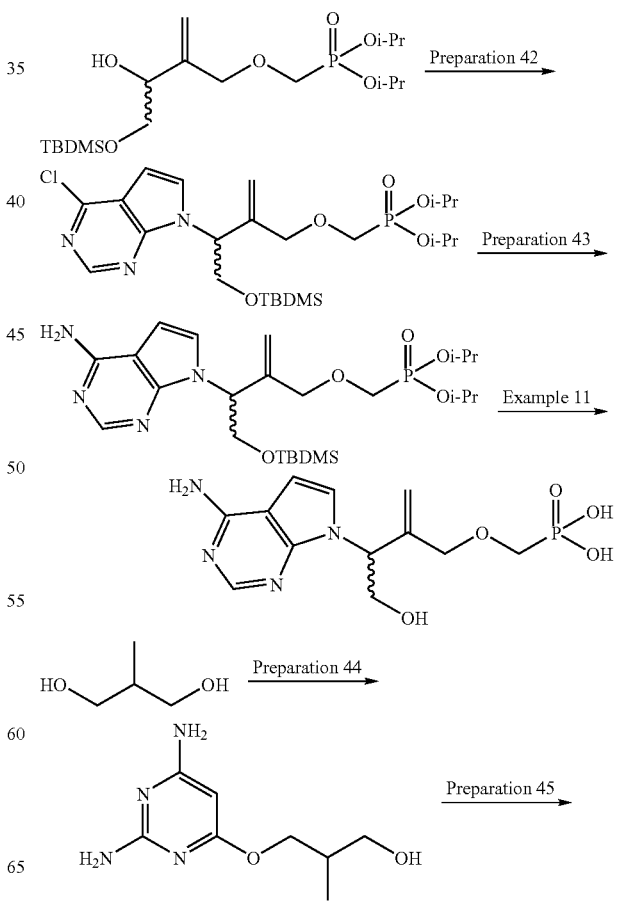

-continued

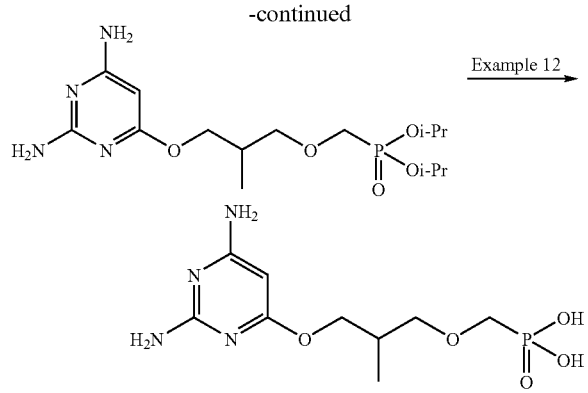

Preparation 42

Synthesis of SDS-56 diisopropyl (4-(tert-butyldimethylsilyloxy)-3-(4-chloro-7H-pyrrolo[2,3-d]pyrimidin-7-yl)-2-methylenebutoxy)methylphosphonate The compound prepared in Preparation 37 (300 mg) was reacted according the same procedure as Preparation 4 (using 6-chloro-7-deazapurine instead of 6-chloropurine) to about 200 mg of title compound including an unknown amount of triphenyl phosphine oxide. ESI 546.3 (M+1)$^+$, C24H41ClN3O5PSi

Preparation 43

Synthesis of SDS-57 diisopropyl (3-(4-amino-7H-pyrrolo[2,3-d]pyrimidin-7-yl)-4-(tert-butyldimethylsilyloxy)-2-methylenebutoxy)methylphosphonate The compound prepared in Preparation 42 (200 mg, estimated) was dissolved in 1.5 mL ethanol and 0.5 mL ammonium hydroxide in a 5 mL microwave vial. The mixture was microwaved at 160° C. for 45 minutes. The solution was injected directly on HPLC using synergi column using 0-100-100% MeOH/H$_2$O for 0-15-20 minutes at 20 mL a minute flow rate. Recovered 40 mg of the title compound. ESI 527.3 (M+1)$^+$, C24H43N4O5PSi

Example 11

Synthesis of SDS-58 (3-(4-amino-7H-pyrrolo[2,3-d]pyrimidin-7-yl)-4-hydroxy-2-methylenebutoxy)methylphosphonic acid The compound prepared in Preparation 43 (40 mg) was dissolved in 10 mL acetonitrile. 2,3,4-collidine (0.75 mL) and TMSr (0.2 mL) were added and stirred overnight. The solution was concentrated, basified with sodium bicarbonate and washed 2× ether. The aqueous solution was acidified with 10% AcOH/H$_2$O and reduced, heating at 55° C., under vacuum to a volume of 3 mL. The solution was injected directly on HPLC using synergi column using 0-100-100% MeOH/H$_2$O for 0-15-20 minutes at 20 mL a minute flow rate. Recovered 5 mg of the title compound. $^1$H NMR(D$_2$O) δ 3.35 (m, 2H), 3.82 (m, 2H), 4.09 (d, 2H), 5.08 (s, 1H), 5.30 (m, 2H), 6.66 (d, 1H), 7.31 (d, 1H), 8.06 (s, 1H); $^{31}$P NMR(D$_2$O) δ 15.75; and ESI 327.4 (M−1)$^-$, C12H17N4O5P

Preparation 44

Synthesis of SDS-59 3-(2,6-diaminopyrimidin-4-yloxy)-2-methylpropan-1-ol

The title compound was prepared by adding 3, 5 mm glass beads into a 40 mL EPA vial. 2-Methylpropane-1,3-diol (560 mg, 3+eq.), t-butyl alcohol (4 mL), 6-chloro pyrimidine-2,4-diamine (220 mg, 1 eq.), and sodium t-butoxide (264.9 mg, 2 eq.) were added to the vial and shook to break loose caked particles and places in a reaction block heated to 100° C. and shaken overnight. Concentrate mixture and purify by flash column chromatography eluting with 100% EtOAc and ramping up to 15% methanol/EtOAc. The title compound was isolated as an oil. ESI 198.1 (M+1)$^+$, C8H14N4O2

Preparation 45

Synthesis of SDS-60 diisopropyl (3-(2,6-diaminopyrimidin-4-yloxy)-2-methyl propoxy)methylphosphonate The compound prepared in Preparation 44 was reacted according to the same procedure as Preparation 10 to give 19.8 mg of the title compound as an oil. ESI 397.3 (M+21)$^+$, C15H29N4O5P

Example 12

Synthesis of SDS-61 (3-(2,6-diaminopyrimidin-4-yloxy)-2-methylpropoxy) methylphosphonic acid The compound prepared in preparation 45 (19.8 mg) was dissolved in 2 mL of DCM. 2,3,4-collidine (0.18 ml, 15 eq.) and trimethyl silyl bromide (TMSBr) (0.08 mL, 10 eq.) were added to the mixture and allowed to stir overnight. Concentrate the mixture under vacuum to remove excess HBr/TMSBr. Basify the residue with saturated sodium bicarbonate and extract 2× with ether. Concentrate the aqueous layer and acidify the residue to pH 5-6 with 10% acetic acid/H$_2$O and purify by reverse phase HPLC using a 2 inch phenomenex synerigi polar RP column with a 0-100% acetonitrile/H$_2$O gradient. Recovered 5.3 mg of the title compound as a white solid. $^1$H NMR(D$_2$O) δ 0.83 (d, 3H), 1.09 (m, 1H), 2.09 (m, 2H), 3.43 (m, 2H), 3.88 (m, 1H), 3.96 (m, 1H); and $^{31}$P NMR(D$_2$O) δ 15.90

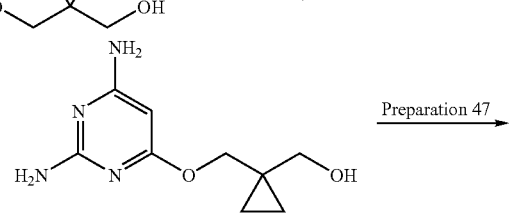

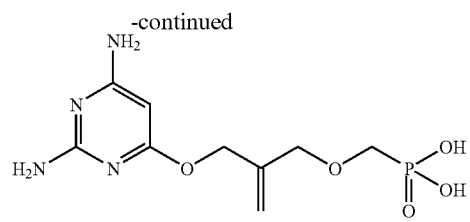

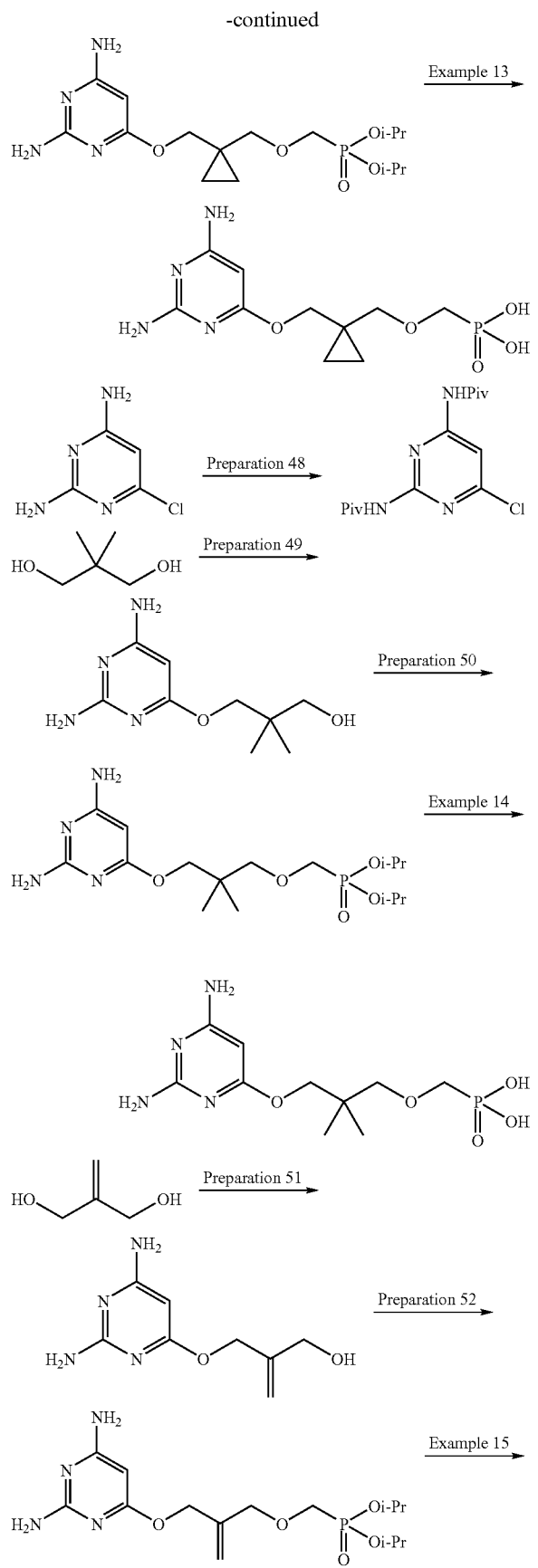

Preparation 46

Synthesis of SDS-62 (1-((2,6-diaminopyrimidin-4-yloxy)methyl)cyclopropyl) methanol The compound prepared in Preparation 20 (431 mg) was reacted according to the same procedure as Preparation 44 to give 100+mg of the title compound as viscous oil. ESI 212.05 $(M+2)^+$, $C_9H_{14}N_4O_2$

Preparation 47

Synthesis of SDS-63 diisopropyl ((1-((2,6-diaminopyrimidin-4-yloxy)methyl) cyclopropyl)methoxy) methylphosphonate The compound prepared in Preparation 46 (100+mg) was reacted according to the same procedure as Preparation 10 to give about 100 mg of the title compound as an oil. ESI 389.7 $(M+1)^+$, $C_{16}H_{29}N_4O_5P$

Example 13

Synthesis of SDS-64 ((1-((2,6-diaminopyrimidin-4-yloxy)methyl)cyclopropyl) methoxy)methylphosphonic acid The compound prepared in Preparation 47 (100 mg) was reacted according to the same procedure as Example 12 to give 60 mg (14% yield 3 steps) of the title compound as a white solid. ESI 303.3 $(M-1)^-$, $C_{10}H_{17}N_4O_5P$

Preparation 48

Synthesis of SDS-65 6-chloro-2,4-dipivalamidopyrimidine

The title compound was made by suspending 2,4-diamino-6-chloropyrimidine (5 g, 1 eq.) in 50 mL DCM. Pivaloyl chloride (6.5 mL, 2.2 eq.) and DMAP (9.7 g, 2.3 eq.) were added to the reaction was stirred for 30 minutes. The reaction was quench with water and the organic layer was washed with citric acid 2×, saturated sodium bicarbonate IX, and brine IX. The organic layer was dried and concentrated to give the title compound as a semi-solid with a nearly quantitative yield.

Preparation 49

Synthesis of SDS-66 3-(2,6-diaminopyrimidin-4-yloxy)-2,2-dimethylpropan-1-ol

The compound prepared in Preparation 48 (300 mg) was reacted according to the same procedure as Preparation 44 (using 2,2-dimethylpropane-1,3-diol instead of 2-methylpropane-1,3-diol) to give 67 mg of the title compound as viscous oil.

115

Preparation 50

Synthesis of SDS-67 diisopropyl (3-(2,6-diaminopyrimidin-4-yloxy)-2,2-dimethylpropoxy)methylphosphonate The compound prepared in Preparation 49 (67 mg) was reacted according to the same procedure as Preparation 10 to give about 59.1 mg of the title compound as an oil.

Example 14

Synthesis of SDS-68 (3-(2,6-diaminopyrimidin-4-yloxy)-2,2-dimethylpropoxy) methylphosphonic acid The compound prepared in Preparation 50 (59.1 mg) was reacted according to the same procedure as Example 12 to give 20 mg (6.8% yield 3 steps) of the title compound as a white solid. ESI 305.3 (M−1)⁻, $C_{10}H_{19}N_4O_5P$

Preparation 51

Synthesis of SDS-69 2-((2,6-diaminopyrimidin-4-yloxy)methyl)prop-2-en-1-ol

The title compound was made by reacting 400 mg of 2-methylenepropane-1,3-diol according to the same procedure as Preparation 44 to give approximately 100 mg of the title compound as viscous oil. ESI 197.1 (M+1)⁺, $C_8H_{12}N_4O_2$

Preparation 52

Synthesis of SDS-70 diisopropyl (2-((2,6-diaminopyrimidin-4-yloxy)methyl) allyloxy)methylphosphonate The compound prepared in Preparation 51 (100 mg) was reacted according to the same procedure as Preparation 10 to give approximately 50 mg of title compound as an oil.

Example 15

Synthesis of SDS-71 (2-((2,6-diaminopyrimidin-4-yloxy)methyl)allyloxy) methylphosphonic acid The compound prepared in Preparation 52 (50 mg) was reacted according to the same procedure as Example 12 to give 30 mg (7.5% yield 3 steps) of the title compound as a solid. ESI 289.4 (M−1)⁻, $C_9H_{15}N_4O_5P$

116

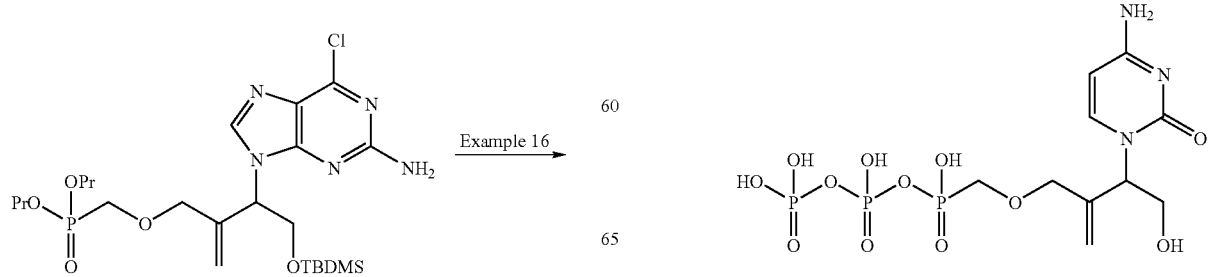

Example 16

[3-(2-Amino-6-oxo-1,6-dihydro-purin-9-yl)-4-hydroxy-2-methylene-butoxymethyl]-phosphonic acid phosphonic acid To a solution of the compound obtained by preparation 41 (51 mg, 0.091 mmol) in acetonitrile (0.91 mL) was added 2,6-lutidine (78 mg, 0.726 mmol) followed by trimethylsilyl iodide (145 mg, 0.726 mmol) at room temperature. After stirring for 1 h, triethylamine (73 mg, 0.726 mmol) and MeOH (1 mL) were added. Solvents were evaporated to give the crude product XX as a white solid. The crude product was treated with a solution of tetrabutylammonium fluoride (0.832 mL of a 1M solution in THF, 0.083 mmol) for 1 h at room temperature. After removal of solvents, the residue was suspended in 1M aqueous HCl (2 mL) and heated to 85° C. for 1.5 h. After cooling to room temperature, the reaction mixture was neutralized with 1 M aqueous $NH_4OH$. After removal of solvent, the crude product was purified by HPLC to provide the desired phosphonate acid XX: $^1H$ NMR ($D_2O$, 300 MHz) δ 8.89 (s, 1H), 5.42 (s, 1H), 5.23 (m, 1H), 5.15 (s, 1H), 4.20-3.96 (m, 4H), 3.55-3.40 (m, 2H); $^{31}P$ NMR ($D_2O$, 300 MHz) δ 16.88 (s); LCMS found 346.1 ($M^++H$, $C_{11}H_{16}N_5O_6P$ requires 346.08).

Example 17

[3-(2-Amino-6-oxo-1,6-dihydro-purin-9-yl)-4-hydroxy-2-methylene-butoxymethyl]-phosphonic acid diphosphophosphonate To the compound obtained Example 16 (7.5 mg, 0.02 mol) in DMSO (0.5 mL) was added tributylamine (10 µL, 0.04 mmol) followed by carbonyldiimidazole (18 mg, 0.11 mmol). Reaction was stirred at room temperature for 1.5 h at which point MeOH (10 µL) was added and stirred for an additional 30 min. Tributyl ammonium pyrophosphate (54 mg, 0.1 mmol) in DMF (500 µL) was added the reaction mixture and stirred for 1 h. After the solvents were evaporated in vacuo, the crude product was purified by ion exchange HPLC (0-60% TEAB) to provide the diphosphophosphonate: LCMS found 505.2 ($M^+H$, $C_{11}H_{18}N_5O_{12}P_3$ requires 505.2).

Preparation 53

[3-(4-Benzoylamino-2-oxo-2H-pyrimidin-1-yl)-4-(tert-butyl-dimethyl-silanyloxy)-2-methylene-butoxymethyl]-phosphonic acid diisopropyl ester To the compound obtained by preparation 37 (151 mg, 0.368 mmol) in anhydrous dioxane (6.1 mL) was added N-benzoylcytosine (158 mg, 0.736 mmol) and triphenylphosphine (193 mg, 0.736 mmol). Diisopropylazodicarboxylate (142 µL, 0.736 mmol) was added dropwise to the reaction mixture at room temperature. After stirring for 6 h, the mixture was filtered and washed with $Et_2O$. After removal of solvent, the crude product was purified by column chromatography on silica (2% MeOH in $CH_2Cl_2$) to provide the title compound: $^1H$ NMR ($CDCl_3$, 300 MHz) δ 9.72 (br s, 1H), 8.44 (d, 1H), 7.98 (m, 4H), 5.72 (t, 1H), 5.42 (s, 1H), 5.22 (s, 1H), 4.75 (m, 1H), 4.47 (m, 1H), 4.27 (dd, 2H), 3.58-3.91 (m, 4H), 1.32 (m, 6H), 1.18 (m, 6H), 0.85 (s, 9H), 0.08 (s, 3H), 0.05 (s, 3H); $^{31}P$ NMR ($CDCl_3$, 300 MHz) δ 19.45 (s); LCMS found 608.4 ($M^++H$, $C_{29}H_{46}N_3O_7PSi$ requires 608.3).

Preparation 54

[3-(4-Amino-2-oxo-2H-pyrimidin-1-yl)-4-(tert-butyl-dimethyl-silanyloxy)-2-methylene-butoxymethyl]-phosphonic acid diisopropyl ester The compound obtained by preparation 53 (102 mg, 0.17 mmol) was dissolved in $THF/MeOH/H_2O$ (3:1:1, 1.7 mL) and treated with 1N aqueous NaOH (420 JIL). The reaction mixture was heated to 30° C. for 3 h at which time the reaction was neutralized with 1N aqueous HCl. After removal of solvent, the crude product was purified by column chromatography on silica (3% MeOH in $CH_2Cl_2$) to provide the title compound: $^1H$ NMR ($CDCl_3$, 300 MHz) δ 7.98 (d, 1H), 6.01 (d, 1H), 5.53 (m, 1H), 5.19 (s, 1H), 4.79 (m, 2H), 4.25 (dd, 2H), 4.03 (dd, 1H), 3.86 (m, 2H), 3.60 (dd, 2H), 1.34-1.37 (m, 12H), 0.86 (s, 9H), 0.07 (s, 3H), 0.05 (s, 3H); $^{31}P$ NMR ($CDCl_3$, 300 MHz) δ 20.49 (s); LCMS found 504.3 ($M^++H$, $C_{22}H_{42}N_3O_6PSi$ requires 504.3).

Example 18

[3-(4-Amino-2-oxo-2H-pyrimidin-1-yl)-4-hydroxy-2-methylene-butoxymethyl]-phosphonic acid The compound obtained by preparation 54 (8 mg, 0.0161 mmol) in acetonitrile (0.16 mL) was treated with 2,6-lutidine (15 µL, 0.127 mmol) followed by iodotrimethylsilylane (18 µL, 0.127 mmol) at room temperature. After stirring for 45 min, triethylamine (18 µL, 0.127 mmol) and MeOH (20 µL) were added. Solvents were evaporated to give the crude diacid as a white solid. The crude product was treated with a solution of tetrabutylammonium fluoride (0.16 mL of a 1M solution in THF, 0.016 mmol) for 0.5 h at 35° C. After removal of solvent, the crude product was purified by HPLC to provide the desired phosphonic acid: $^1H$ NMR ($CD_3OD$, 300 MHz) δ 7.88 (d, 1H), 6.39 (d, 1H), 5.80 (m, 1H), 5.36 (m, 2H), 4.22 (m, 2H), 3.60-3.89 (m, 4H); $^{31}P$ NMR ($CD_3OD$, 300 MHz) δ 18.14 (s); LCMS found 306.1 ($M^++H$, $C_{10}H_{16}N_3O_6P$ requires 306.1).

Example 19

[3-(4-Amino-2-oxo-2H-pyrimidin-1-$Y^1$)-4-hydroxy-2-methylene-butoxymethyl]-phosphonic acid diphosphophosphonate To phosphonic diacid XX (3.6 mg, 0.01 mmol) in DMSO (250 µL) was added tributylamine (5 µL, 0.02 mmol) followed by carbonyldiimidazole (9 mg, 0.05 mmol). Reaction was stirred at room temperature for 1.5 h at which point MeOH (5 µL) was added and stirred for an additional 30 min. Tributyl ammonium pyrophosphate (27 mg, 0.05 mmol) in DMF (250 µL) was added and the reaction mixture stirred for 1 h. After the solvents were evaporated in vacuo, the crude product was purified by ion exchange HPLC (0-60% TEAB) to provide the diphosphophosphonate as the bistriethylammonium salt: $^1H$ NMR ($D_2O$, 300 MHz) δ 8.55 (s, 1H), 7.67 (m, 1H), 7.34 (s, 1H), 6.27 (m, 1H), 5.65 (m, 1H), 5.28 (d, 2H), 4.11 (m, 2H), 3.65-3.81 (m, 3H), 3.48 (q, 2H), 3.06 (q, 2H), 1.22 (t, 3H), 1.14 (t, 3H).

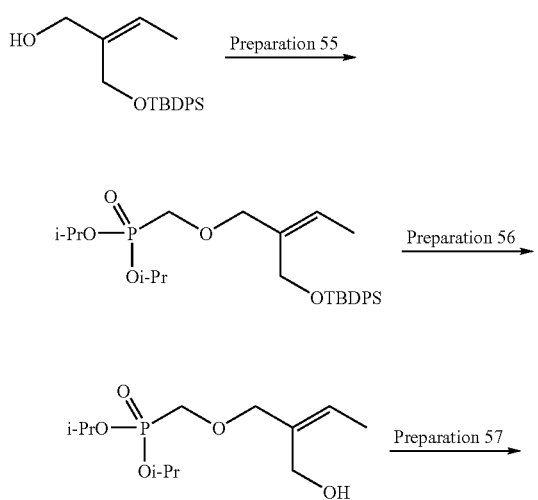

Preparation 55

[2-(tert-Butyl-diphenyl-silanyloxymethyl)-but-2-enyloxymethyl]-phosphonic acid diisopropyl ester To a stirred solution of 2-(tert-Butyl-diphenyl-silanyloxymethyl)-but-2-en-1-ol (see: J. Org. Chem. 58, 2151-2161, 1993), (660 mg (1.94 mmol)) in anhydrous DMF was added Magnesium t-butoxide 660 mg (3.88 mmol) followed by isopropylphosphonate tosylate 1.2 g (2.91 mmol). The reaction was stirred under Ar at 70° C. for 16 h, until the reaction was complete by TLC. Solvents were removed in vacuo and the residue (yellow gum) resuspended in EtOAc. Saturated NH$_4$Cl— was added and the reaction extracted with EtOAc (2×40 mL). The combined organic layers were washed with brine, dried over sodium sulfate, filtered and concentrated in vacuo. Flash chromatography (gradient elution, hexanes/ethyl acetate, 9:1 to 2:3) yielded the title compound 674 mg (1.3 mmol; 67% yield).

$^1$H MNR(300 MHz, CDCl$_3$) δ 7.7 (m, 4H), 7.4 (m, 6H), 5.6 (m, 1H), 4.75 (m, 2H), 4.3 (s, 2H), 4.2 (s, 2H), 3.6 (d, 2H), 1.5 (m, 3H), 1.2 (m, 12H), 1.0 (m, 9H); $^-$P NMR δ20.25.

Preparation 56

(2-Hydroxymethyl-but-2-enyloxymethyl)-phosphonic acid dipropyl ester

To a stirred solution of compound obtained by preparation 56 (137 mg (0.26 mmol)) in THF (5 mL) was added 0.4 mL of TBAF (1.0 M in THF) at 0° C. and stirred under Ar. The mixture was stirred for 3 h until the reaction showed completion. The solvents were removed in vacuo and the reaction was purified by flash chromatography (gradient elution, hexanes/ethyl acetate, 2:3 to 0:1 to 5% MeOH/CH$_2$Cl$_2$). The title alcohol 66.7 mg (0.24 mmol; 92%) was isolated. $^1$H MNR (300 MHz, CDCl$_3$) δ 5.6 (m, 1H), 3.6-3.8 (m, 2H), 4.25 (s, 2H), 4.1 (s, 2H), 3.7 (d, 2H), 2.62 (br. s, 1H), 1.7 (m, 3H), 1.3 (m, 12H); $^-$P NMR δ20.44

Preparation 57

[2-(2-Amino-6-chloro-purin-9-ylmethyl)-but-2-enyloxymethyl]-phosphonic acid

To a stirred solution of the compound obtained by preparation 56 in dioxane was added triphenylphosphine and 6-chloro-2-aminopurine. DIAD was added dropwise. The reaction was protected from light and stirred under Ar for 18 h at ambient temperature. The resulting solid was filtered off and the filterate concentrated in vacuo. The resulting oil was triturated with hexanes. Flash chromatography purification (gradient elution 100% CH$_2$Cl$_2$ to 5% MeOH/CH$_2$Cl$_2$) provided the Cl-purine compound This compound was subsequently dissolved in MeCN (2 mL) and 2,6-lutidine (0.28 mL, 2.4 mmol) was added. The reaction was cooled to 0° C. and stirred under Ar. To this solution was added TMSBr dropwise and the reaction left to stir for 36 h until the reaction showed completion. The reaction was cooled to −78° C. and quenched with MeOH followed by ammonium hydroxide. The solvents were removed in vacuo and the residue purified by C18 column using H$_2$O as eluent. The diacid was isolated as its ammonium salt 16.6 mg (0.05 mmol; 20% in 2 steps). m/z (M+H)+348.01.

Example 20

[2-(2,6-Diamino-purin-9-ylmethyl)-but-2-enyloxymethyl]-phosphonic acid

A methanolic solution (5 mL) of compound obtained by preparation 57 (16.6 mg; 0.05 mmol) was cooled to −78° C. in a high pressure tube. Ammonia gas (5 mL) was bubbled into the tube and subsequently placed in a bomb and heated at 100° C. to 150 psi for 96 h. The reaction was concentrated and purified by HPLC using a polar RP column (H$_2$O to 5% MeCN over 30 min). The final product was isolated in as its ammonium salt, 4 mg as a white powder. $^1$H MNR (300 MHz, D$_2$O) δ 7.7 (s, 1H), 5.8-5.9 m, 1H), 4.6 (s, 2H), 3.78 (s, 2H), 3.3 (d, 2H), 1.65 (m, 3H); $^{31}$P NMR δ15.94; m/z 329.13.

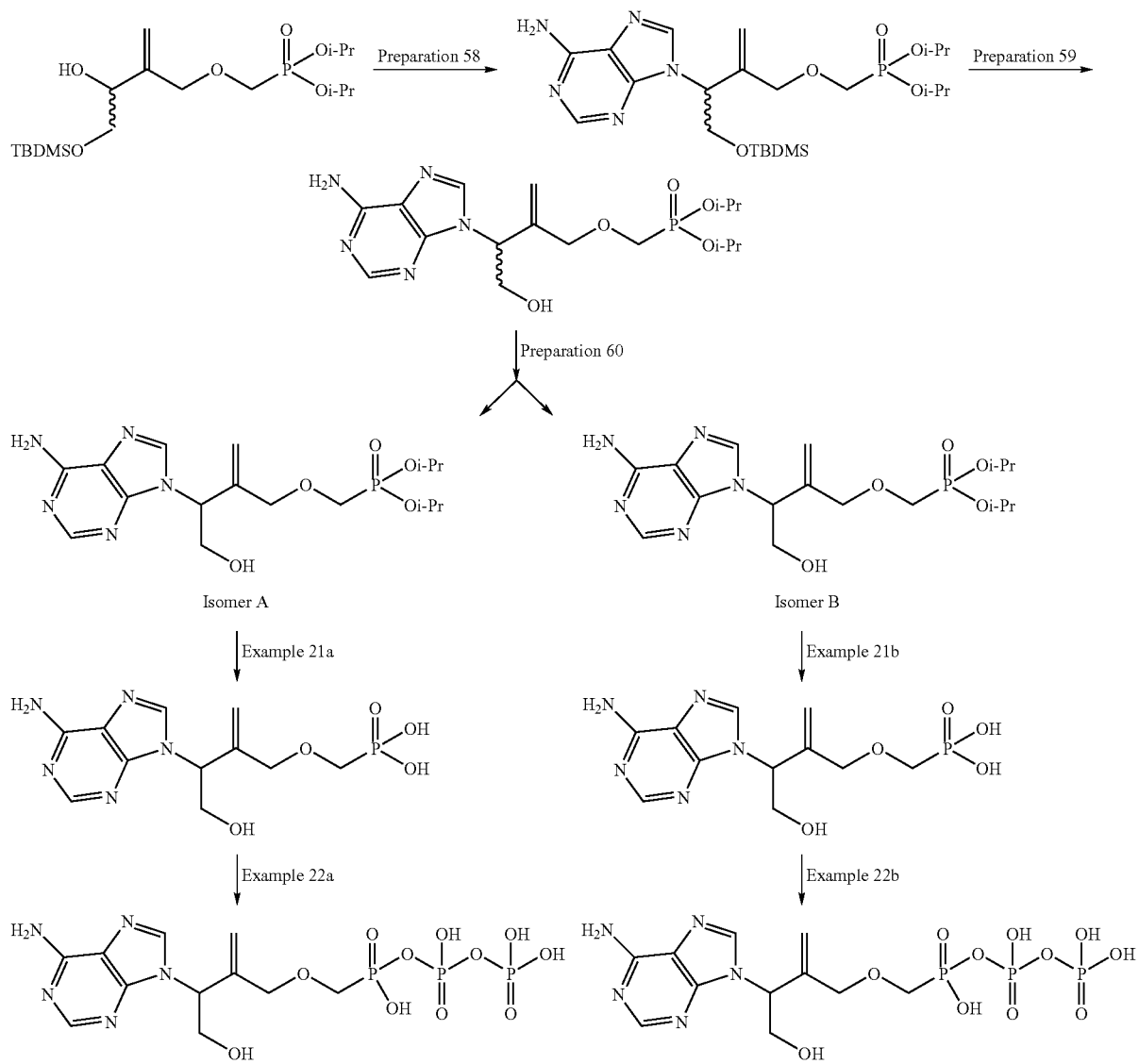

Preparation 58

Synthesis of SDS-72 diisopropyl (3-(6-amino-9H-purin-9-yl)-4-(tert-butyldimethylsilyloxy)-2-methylenebutoxy)methylphosphonate The compound prepared in Preparation 37 (2.08 mg) was reacted according the same procedure as Preparation 4 (using 6-aminopurine instead of 6-chloropurine) to give 580 mg of the title compound. ESI 562.3 (M+1)$^+$, $C_{23}H_{41}ClN_5O_5PSi$

Preparation 59

Synthesis of SDS-73 diisopropyl (3-(6-amino-9H-purin-9-yl)-4-hydroxy-2-methylenebutoxy)methylphosphonate The compound prepared in Preparation 58 (580 mg) was dissolved in methanol and 10% AcOH/water heated at 60° C. until most of the TBS was removed (5 hours). Concentrate to 30 mL and lyophilize to remove all water. ESI 414.2 (M+1)$^+$, $C_{17}H_{28}N_5O_5P$

Preparation 60

Synthesis of SDS-74 and SDS-75 diisopropyl (3-(6-amino-9H-purin-9-yl)-4-hydroxy-2-methylenebutoxy)methylphosphonate The compound prepared in Preparation 59 (390 mg) was dissolved in 20% ethanol/heptane at a concentration of roughly 10 mg/mL. The solution was purified 3-4 mL an injection on a Daicel Chemical Industries 2 cm φ×25 cm AS-H chiral column run 20% ethanol/heptane at 5 mL/minute. Recovered 120 mg of SDS-XX (peak one, retention time 36.5 minutes) and 130 mg of SDS7XX (peak two, retention time 40.5 minutes). ESI 414.2 (M+1)$^+$, $C_{17}H_{28}N_5O_5P$

Example 21a

Synthesis of SDS-76 (3-(6-amino-9H-purin-9-yl)-4-hydroxy-2-methylenebutoxy)methylphosphonic acid The compound prepared in Preparation 60 (120 mg SDS-74) was reacted according to the same procedure as Preparation 4 to give 46 mg of the title compound. ESI 328.4 (M−1)⁻, $C_{11}H_{16}N_5O_5P$

Example 21b

Synthesis of SDS-77 (3-(6-amino-9H-purin-9-yl)-4-hydroxy-2-methylenebutoxy)methylphosphonic acid The compound prepared in Preparation 60 (130 mg SDS-75) was reacted according to the same procedure as Preparation 4 to give 26 mg of the title compound. ESI 328.4 (M−1)⁻, $C_{11}H16N_5O_5P$

Example 22a

Synthesis of SDS-78 (3-(6-amino-9H-purin-9-yl)-4-hydroxy-2-methylenebutoxy)methylphosphonic acid diphosphphonate The compound prepared in Example 21a (10 mg) was dissolved in 1 mL DMF. CDI (24.3 mg) and imidazole (20.4 mg) were added to the mixture and stirred until done by LC-MS (<10 minutes, mass of 378). The CDI was quenched with 0.2 mL MeOH and stirred for 30 minutes. Pyrophosphate (71 mg in 1 mL of DMF) was added and stirred overnight. The mixture was concentrated under vacuum and dissolved in water. The solution was purified by ion exchange HPLC using a Phenomenex Luna 5 μNH₂ 100 A 250×30 cm column running a 0- 0-80% 50 mM TEAB/1M TEAB in water from 0-5-25 minutes. Recovered 5 mg of the title compound with a retention time of 21.5 minutes. ³¹P NMR(D₂O) δ 22.78, 8.56, 8.30

Example 22b

Synthesis of SDS-79 (3-(6-amino-9H-purin-9-yl)-4-hydroxy-2-methylenebutoxy)methylphosphonic acid diphosphphonate The compound prepared in Example 21b (10 mg) was reacted according to the same procedure as Example 22a to give 2 mg of the title compound. ³¹P NMR(D₂O) δ 22.90, 8.33, 8.25

I claim:

1. A compound having the formula:

wherein:
$X^1$ is selected from the group consisting of:

$X^2$ is selected from the group consisting of O, NR and S;
$Y^1$ is independently O, S, NR, or N—NR₂;
$Y^2$ is independently O, NR, N—NR₂, —S(O)$_{M2}$—, or —S(O)$_{M2}$—S(O)$_{M2}$—;
$Y^3$ and Z are independently selected from the group consisting of H, OH, OR, NR₂, CN, NO₂, F, Cl, Br, and I;
$R^x$ is independently H, $W^3$, a protecting group, or the formula:

M1a, M1c, and M1d are independently 0 or 1;
M12c is 0, 1, 2, 3, 4, 5, 6, 7, 8, 9, 10, 11 or 12;
$R^y$ is independently H, $W^3$, or a protecting group;
M2 is 0, 1 or 2;
$R^1, R^2, R^4, R^6, R^7$, and $R^8$ are independently selected from the group consisting of H, F, Cl, Br, I, OH, —C(=Y¹)R, —C(=Y¹)OR, —C(=Y¹)N(R)₂, —N(R)₂, —SR, —S(O)R, —S(O)₂R, —S(O)(OR$^x$), —S(O)₂(OR$^x$), —OC(=Y¹)OR$^x$, —OC(=Y¹)OR$^x$, —OC(=Y¹)(N(R$^x$)₂), —SC(=Y¹)R$^x$, —SC(=Y¹)OR$^x$, —SC(=Y¹)(N(R$^x$)₂), —N(R$^x$)C(=Y¹)OR$^x$, —N(R$^x$)C(=Y¹)OR$^x$, —N(R$^x$)C(=Y¹)N(R$^x$)₂, amino (—NH₂), alkylamino, dialkylamino, C₁-C₈ alkyl, C₁-C₈ alkylsulfonate, C₁-C₈ alkylamino, alkylsulfone (—SO₂R), arylsulfone (—SO₂Ar), arylsulfoxide (—SOAr), arylthio (—SAr), sulfonamide (—SO₂NR₂), alkylsulfoxide (—SOR), ester (—C(=O)OR), amido (—C(=O)NR₂), nitrile (—CN), azido (—N₃), nitro (—NO₂), C₁-C₈ alkoxy (—OR), C₁-C₈ alkyl, C₁-C₈ substituted alkyl, C₂-C₈ alkenyl, C₂-C₈ substituted alkenyl, C₂-C₈ alkynyl, C₂-C₈ substituted alkynyl, C₆-C₂₀ aryl, C₆-C₂₀ substituted aryl, C₂-C₂₀ heteroaryl, C₂-C₂₀ substituted heteroaryl, polyethyleneoxy, and $W^3$; or
when taken together, two of $R^1, R^2, R^4, R^6, R^7$, and $R^8$ form a carbocyclic ring of 3 to 7 carbon atoms;
$R^3$ is hydroxyalkyl;
$R^5$ is C₁-C₈ substituted alkyl;
R is selected from the group consisting of C₁-C₈ alkyl, C₁-C₈ substituted alkyl, C₂-C₈ alkenyl, C₂-C₈ substituted alkenyl, C₂-C₈ alkynyl, C₂-C₈ substituted alkynyl, C₆-C₂₀ aryl, C₆-C₂₀ substituted aryl, C₂-C₂₀ heteroaryl, and C₂-C₂₀ substituted heteroaryl;
$W^3$ is $W^4$ or $W^5$;
$W^4$ is R, —C(Y¹)R, —C(Y¹)W⁵, —SO₂R, or —SO₂W⁵;

W⁵ is carbocycle or heterocycle wherein W⁵ is independently substituted with 0 to 3 R groups; and NUCLEOBASE is selected from the group consisting of adenine, guanine, 2-aminopurine, 2-amino-6-chloropurine, 2,6-diaminopurine, hypoxanthine, isoguanine, 6-thioguanine, O⁶-methylguanine, and N⁶-methyladenine or a pharmaceutically acceptable salt thereof.

2. The compound or salt of claim 1, wherein $R^3$ is hydroxymethyl or hydroxyethyl.

3. The compound or salt of claim 1, wherein $R^5$ is hydroxyethyl.

4. The compound or salt of claim 1 having the formula:

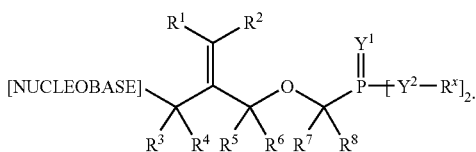

5. A compound selected from the group consisting of:

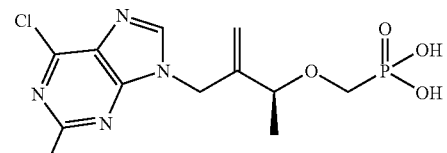

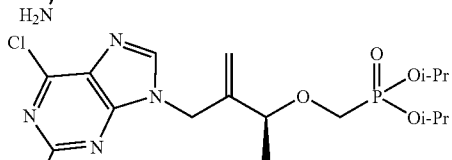

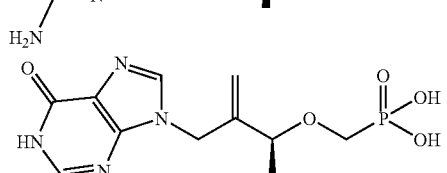

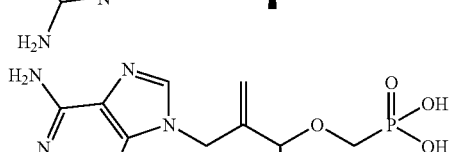

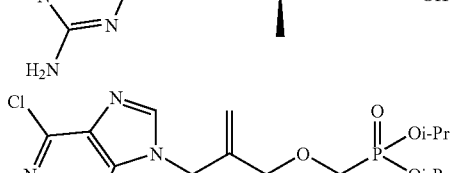

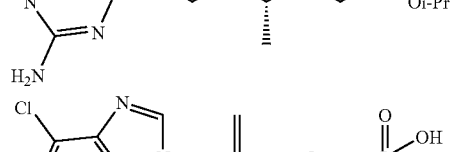

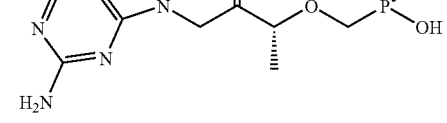

-continued

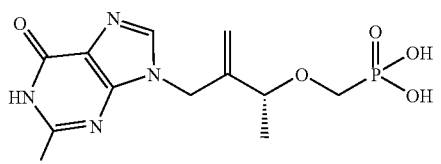

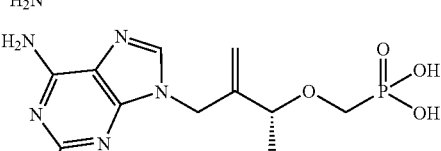

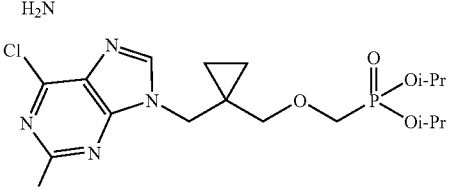

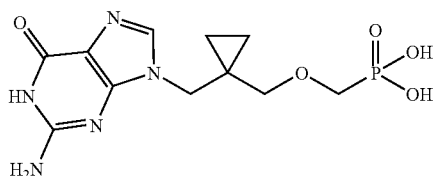

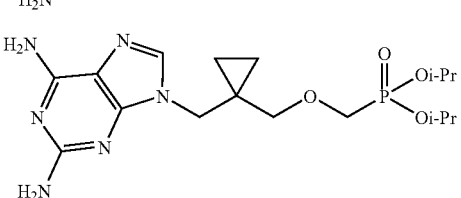

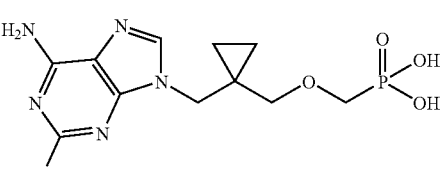

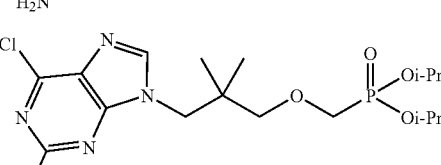

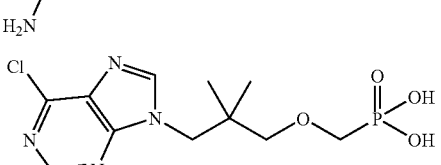

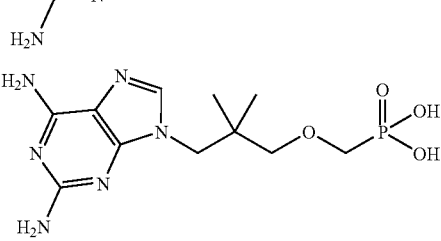

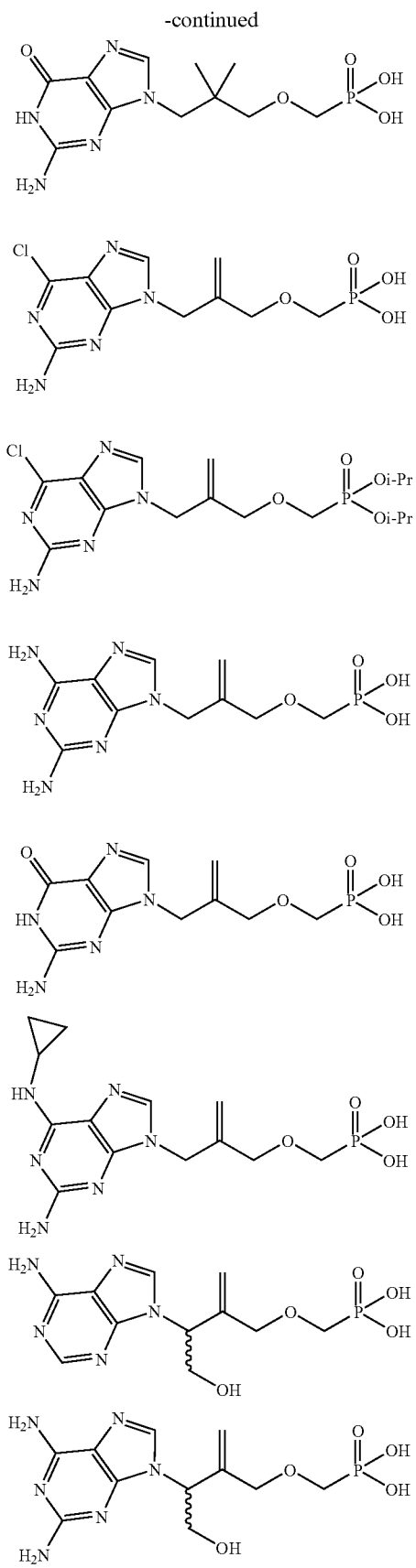
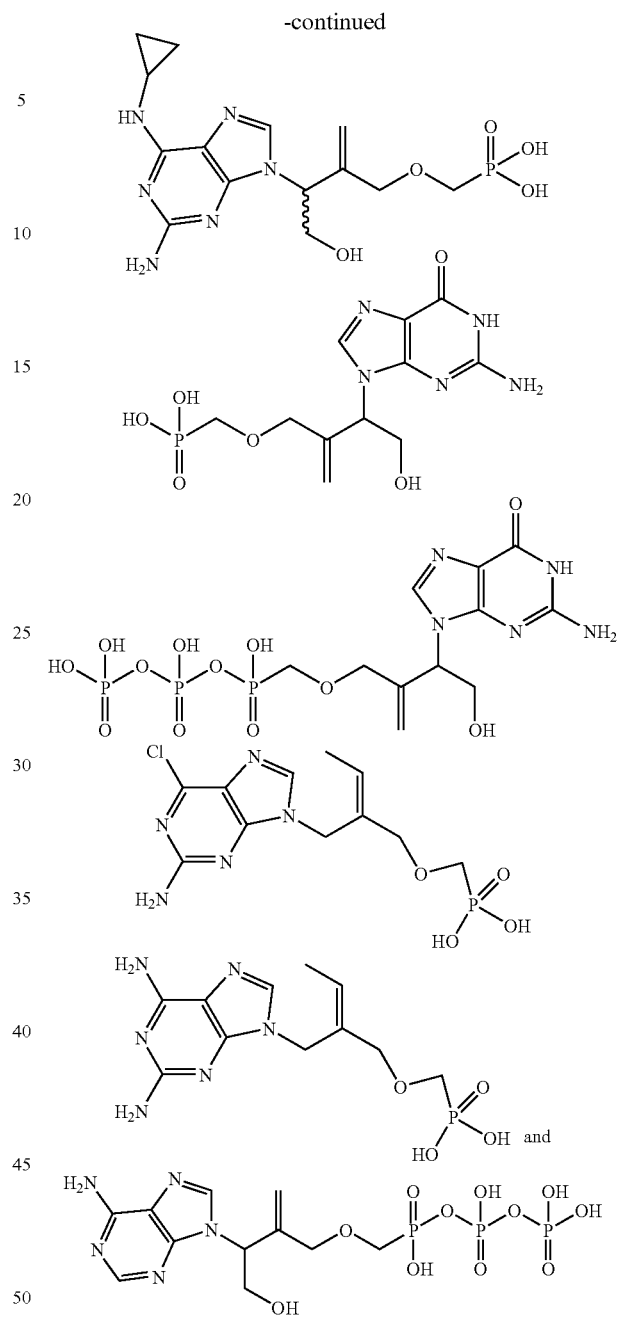

or a pharmaceutically acceptable salt thereof.

6. A pharmaceutical composition comprising an effective amount of the compound or salt of claim 1, and a pharmaceutically acceptable diluent, carrier or excipient.

7. A pharmaceutical composition comprising an effective amount of the compound or salt of claim 5, or and a pharmaceutically acceptable diluent, carrier or excipient.

8. A method for the treatment of the symptoms or effects of HIV infection in an animal, comprising administering to said animal the pharmaceutical composition of claim 6.

9. A method for the treatment of the symptoms or effects of HIV infection in an animal, comprising administering to said animal the pharmaceutical composition of claim 7.

* * * * *